US012758656B2

(12) United States Patent
Chen et al.

(10) Patent No.: US 12,758,656 B2
(45) Date of Patent: Oct. 13, 2026

(54) LINKER PEPTIDE, FVIII PROTEIN OR VARIANT THEREOF CONTAINING LINKER PEPTIDE, AND USE THEREOF

(71) Applicant: SHENZHEN SYNO MINICIRCLE BIOTECHNOLOGY CO., LTD., Shenzhen (CN)

(72) Inventors: Ping Chen, Shenzhen (CN); Jie Liu, Shenzhen (CN); Xiaohu Hou, Shenzhen (CN); Guochuang Chen, Shenzhen (CN); Zhiying Chen, Shenzhen (CN)

(73) Assignee: SHENZHEN SYNO MINICIRCLE BIOTECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/880,434

(22) PCT Filed: Jun. 30, 2023

(86) PCT No.: PCT/CN2023/104477
§ 371 (c)(1),
(2) Date: Jul. 1, 2025

(87) PCT Pub. No.: WO2024/007978
PCT Pub. Date: Jan. 11, 2024

(65) Prior Publication Data

US 2025/0325706 A1 Oct. 23, 2025

(30) Foreign Application Priority Data

Jul. 7, 2022 (CN) ........................ 202210823387.5

(51) Int. Cl.

| | |
|---|---|
| ***A61K 48/00*** | (2006.01) |
| ***A61K 38/00*** | (2006.01) |
| ***A61P 7/04*** | (2006.01) |
| ***C07K 14/755*** | (2006.01) |
| ***C12N 15/85*** | (2006.01) |

(52) U.S. Cl.
CPC ............ *A61K 48/0058* (2013.01); *A61P 7/04* (2018.01); *C07K 14/755* (2013.01); *C12N 15/85* (2013.01); *A61K 38/00* (2013.01); *C07K 2319/31* (2013.01); *C12N 2800/107* (2013.01)

(58) Field of Classification Search
CPC .. A61K 48/0058; A61K 38/00; A61K 48/005; A61P 7/04; C07K 14/755; C07K 2319/31; C07K 2319/00; C12N 15/85; C12N 2800/107; C12N 2800/22
See application file for complete search history.

(56) References Cited

U.S. PATENT DOCUMENTS

| | | | | |
|---|---|---|---|---|
| 9,447,168 | B2 | 9/2016 | Nathwani et al. | |
| 10,124,041 | B2 | 11/2018 | Nathwani et al. | |
| 10,792,336 | B2 | 10/2020 | Nathwani et al. | |
| 11,014,975 | B2 | 5/2021 | Sabatino et al. | |
| 11,419,920 | B2 | 8/2022 | Nathwani et al. | |
| 2015/0158930 | A1* | 6/2015 | Nathwani | A61K 38/37 435/254.2 |
| 2017/0049859 | A1 | 2/2017 | Nathwani et al. | |
| 2017/0233456 | A1 | 8/2017 | Sabatino et al. | |
| 2018/0311317 | A1 | 11/2018 | Nathwani et al. | |
| 2020/0390866 | A1 | 12/2020 | Nathwani et al. | |
| 2022/0033475 | A1 | 2/2022 | Arruda et al. | |
| 2023/0241180 | A1 | 8/2023 | Nathwani et al. | |

FOREIGN PATENT DOCUMENTS

| | | | |
|---|---|---|---|
| AU | 2013276247 | A1 | 1/2015 |
| AU | 2013276247 | B2 | 3/2017 |
| AU | 2015301598 | A1 | 3/2017 |
| AU | 2015301598 | B2 | 7/2020 |
| AU | 2019366942 | A1 | 6/2021 |
| BR | 112017002781 | A2 | 12/2017 |
| CA | 2 875 449 | A1 | 12/2013 |
| CA | 2 958 141 | A1 | 2/2016 |
| CA | 3 115 535 | A1 | 4/2020 |
| CN | 104292341 | A | 1/2015 |
| CN | 107427557 | A | 12/2017 |
| CN | 108795986 | A | 11/2018 |
| CN | 110684798 | A | 1/2020 |
| CN | 112575034 | A | 3/2021 |
| CN | 113248594 | A | 8/2021 |
| CN | 113301911 | A | 8/2021 |
| EP | 3 180 022 | A2 | 6/2017 |
| EP | 2 859 016 | B1 | 8/2017 |

(Continued)

OTHER PUBLICATIONS

Mancuso, M. E. et al. "Fc-fusion technology and recombinant FVIII and FIX in the management of the hemophilias," Drug Design, Development and Therapy, vol. 8, 2014, pp. 365-371.
Gruppo, R. et al. "Perioperative haemostasis with full-length, PEGylated, recombinant factor VIII with extended half-life (rurioctocog alfa pegol) in patients with haemophilia A: Final results of a multicentre, single-arm phase III trial," Haemophilia, Sep. 7, 2018, pp. 773-781.

(Continued)

*Primary Examiner* — Iqbal H Chowdhury

(74) *Attorney, Agent, or Firm* — OPENPTO US LLC; Yuhao Liang

(57) ABSTRACT

A connecting peptide, a coagulation factor 8 protein containing the connecting peptide or a variant thereof and uses thereof, and belongs to the field of gene defect treatment drugs. The connecting peptide can improve the expression level, activity and therapeutic effect of coagulation factor eight protein or its variants using microcircle DNA as a carrier, and also has good secondary administration therapeutic effect, and has good safety and can be used in long-term expression in vivo and other advantages.

3 Claims, 13 Drawing Sheets

Specification includes a Sequence Listing.

(56) References Cited

FOREIGN PATENT DOCUMENTS

| | | | | |
|---|---|---|---|---|
| EP | 3 180 022 | A4 | | 2/2019 |
| EP | 3 870 206 | A2 | | 9/2021 |
| EP | 3 870 206 | A4 | | 4/2023 |
| ES | 2 640 586 | T3 | | 11/2017 |
| JP | 2015-521465 | A | | 7/2015 |
| JP | 2018-506261 | A | | 3/2018 |
| JP | 6473416 | B2 | | 2/2019 |
| JP | 2021-3120 | A | | 1/2021 |
| JP | 2022-512787 | A | | 2/2022 |
| JP | 7237903 | B2 | | 3/2023 |
| KR | 10-2017-0084012 | A | | 7/2017 |
| SA | 517380883 | B1 | | 12/2021 |
| SG | 11201701033 | | | 3/2017 |
| WO | 2013/186563 | A2 | | 12/2013 |
| WO | 2013/186563 | A3 | | 12/2013 |
| WO | 2016/025764 | A2 | | 2/2016 |
| WO | 2016/025764 | A3 | | 4/2016 |
| WO | WO2019/161310 | A1 | * | 8/2019 |
| WO | 2019/228527 | A1 | | 12/2019 |
| WO | 2020/086686 | A2 | | 4/2020 |
| WO | 2020/086686 | A3 | | 5/2020 |
| WO | 2021/042944 | A1 | | 3/2021 |
| ZA | 201701039 | B | | 8/2021 |

OTHER PUBLICATIONS

Konkle, B. A. et al. "BIVV001 Fusion Protein as Factor VIII Replacement Therapy for Hemophilia A," New England Journal of Medicine, vol. 383, No. 11, Sep. 10, 2020, pp. 1018-1027.

Batty, P. et al. "Hemophilia Gene Therapy: Approaching the First Licensed Product," HemaSphere, vol. 5, No. 3, Nov. 2, 2020, pp. 1-8.

Oct. 8, 2018 Supplementary European Search Report issued in European Patent Application No. EP 15 83 2128.

Miao, H. Z. et al. "Bioengineering of coagulation factor VIII for improved secretion," Hemostasis, Thrombosis, and Vascular Biology, vol. 103, No. 9, May 1, 2004, pp. 3412-3419.

Toole, J. T. et al. "A large region (=95kDa) of human factor VIII is dispensable for in vitro procoagulant activity," Proc. Natl. Acad. Sci. USA, vol. 83, Aug. 1986, pp. 5939-5942.

Mcintosh, J. et al. "Therapeutic levels of FVIII following a single peripheral vein administration of rAAV vector encoding a novel human factor VIII variant," Blood, vol. 121, No. 17, Apr. 25, 2013, pp. 3335-3344.

Lynch, C. M. et al. "Sequences in the Coding Region of Clotting Factor VIII Act as Dominant Inhibitors of RNA Accumulation and Protein Production," Human Gene Therapy, vol. 4, 1993, pp. 259-272.

Thim, L. et al. "Purification and characterization of a new recombinant factor VIII (N8)," Haemophilia, vol. 16, 2010, pp. 349-359.

Karlin, S. et al. "Methods for assessing the statistical significance of molecular sequence features by using general scoring schemes," Proc. Natl. Acad. Sci. USA, vol. 87, Mar. 1990, pp. 2264-2268.

Karlin, S. et al. "Applications and statistics for multiple high-scoring segments in molecular sequences," Proc. Natl. Acad. Sci. USA, vol. 90, Jun. 1993, pp. 5873-5877.

Altschul, S. F. et al. "Basic Local Alignment Search Tool," J. Mol. Biol. vol. 215, 1990, pp. 403-410.

Chen, C. et al. "Roles of Phytanoyl-CoA a-Hydroxylase in Mediating the Expression of Human Coagulation Factor VIII*," The Journal of Biological Chemistry, vol. 276, No. 49, 2001, pp. 46340-46346.

Mcdonough, M. A. et al. "Structure of Human Phytanoyl-CoA 2-Hydroxylase Identifies Molecular Mechanisms of Refsum Disease*," The Journal of Biological Chemistry, vol. 280, No. 49, Dec 9, 2005, pp. 41101-41110.

Kaufman, R. J. et al. "Biosynthesis, assembly and secretion of coagulation factor VIII," Blood Coagulation and Fibrinolysis, vol. 8, Suppl. 2, 1997, pp. S3-S14.

Dec. 20, 2023 International Search Report issued in International Patent Application No. PCT/CN2023/104477.

Oct. 20, 2023 Written Opinion of the International Searching Authority issued in International Patent Application No. PCT/CN2023/104477.

Sambrook, J. et al. "Molecular Cloning: A Laboratory Manual," 3rd Edition, 2001.

* cited by examiner

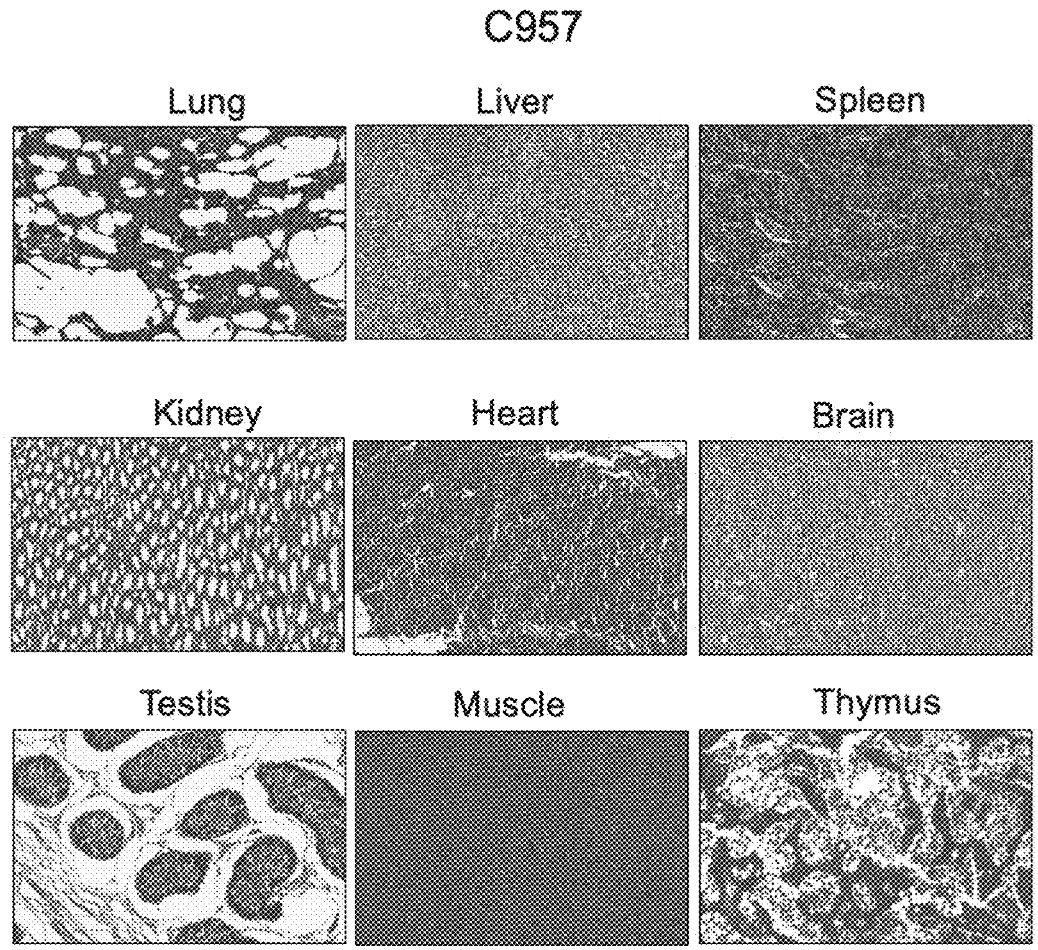

- Lung: No obvious abnormality in the tissue structure of alveoli and bronchi. No inflammatory cell infiltration, no degeneration or necrosis.
- Liver: Normal tissue architecture, clear hepatic plate structure. No inflammatory cell infiltration, no degeneration or necrosis.
- Spleen: Normal splenic tissue structure. No inflammatory cell infiltration, no degeneration or necrosis.
- Kidney: Normal tissue structure of glomeruli and renal tubules. No inflammatory cell infiltration, degeneration or necrosis.
- Heart: Normal cardiac tissue structure. No inflammatory cell infiltration, degeneration or necrosis.
- Brain: Normal brain tissue structure. No inflammatory cell infiltration, degeneration or necrosis.
- Testis: No obvious abnormality in the testicular tissue. Spermatocytes at various stages and spermatids are visible within the seminiferous tubules. No degeneration or necrosis, no inflammatory cell infiltration.
- Muscle: Muscle cells are arranged in parallel with clear nuclei. No degeneration or necrosis, no inflammatory cell infiltration.
- Thymus: Normal thymic tissue structure. No inflammatory cell infiltration, degeneration or necrosis.

FIG. 21A

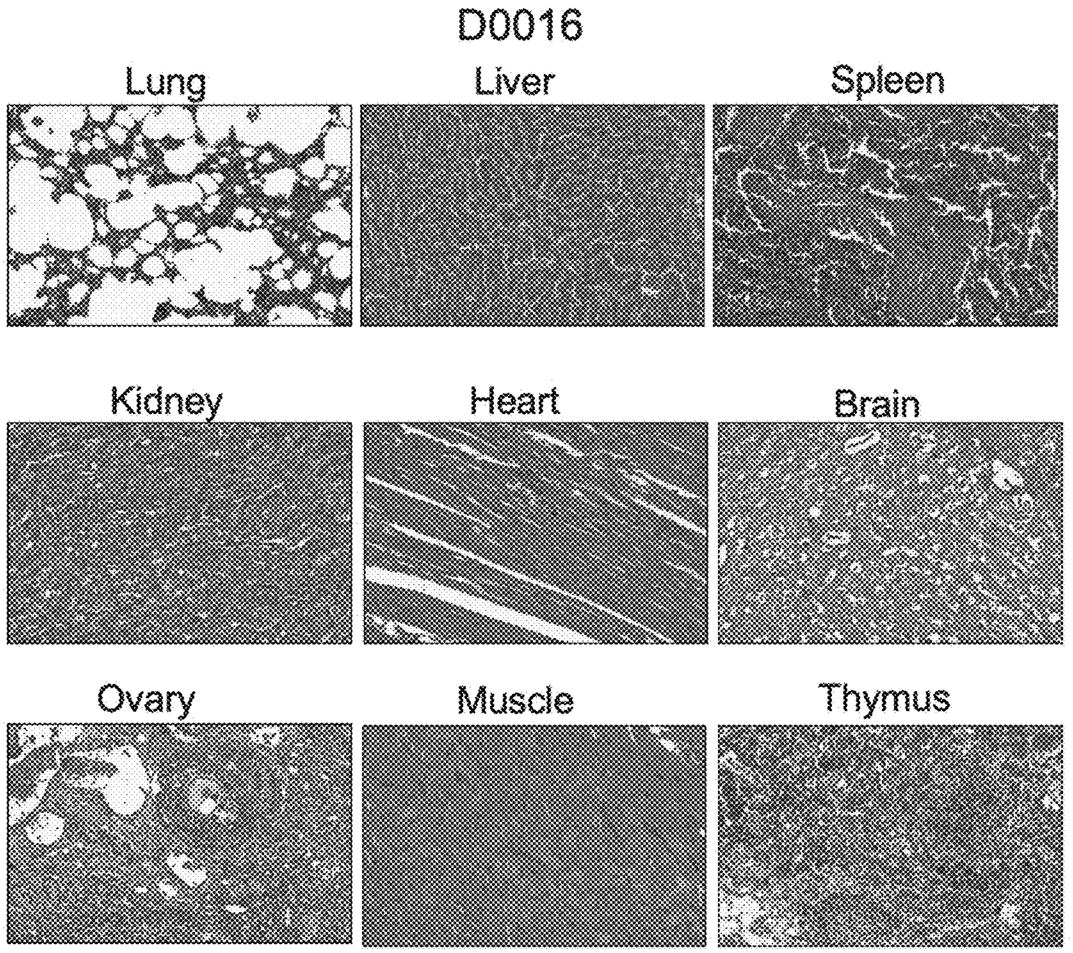

- Lung: No obvious abnormality in the tissue structure of alveoli and bronchi. No inflammatory cell infiltration, no degeneration or necrosis.
- Liver: Normal tissue architecture, no hepatic plate structure. No inflammatory cell infiltration, no degeneration or necrosis.
- Spleen: Normal splenic tissue structure. No inflammatory cell infiltration, no degeneration or necrosis.
- Kidney: Normal tissue structure of glomeruli and renal tubules. No inflammatory cell infiltration, degeneration or necrosis.
- Heart: Normal cardiac tissue structure. No inflammatory cell infiltration, degeneration or necrosis.
- Brain: Normal brain tissue structure. No inflammatory cell infiltration, degeneration or necrosis.
- Ovary: No obvious abnormality in the oocytes. No degeneration or necrosis, no inflammatory cell infiltration.
- Muscle: Muscle cells are arranged in parallel with clear nuclei. No degeneration or necrosis, no inflammatory cell infiltration.
- Thymus: Normal thymic tissue structure. No inflammatory cell infiltration, degeneration or necrosis.

FIG. 21B

SEQUENCE LISTING

```
Sequence total quantity: 62
SEQ ID NO: 1            moltype = AA  length = 72
FEATURE                 Location/Qualifiers
source                  1..72
                        mol_type = protein
                        organism = synthetic construct
SEQUENCE: 1
SFSQNSRHPS TRQKQFNATN VSNNSNTSND SNVSNKTSNN SNATNKTNNT NDSTNRTNQT  60
NTSPPVLKRH QR                                                      72

SEQ ID NO: 2            moltype = AA  length = 74
FEATURE                 Location/Qualifiers
source                  1..74
                        mol_type = protein
                        organism = synthetic construct
SEQUENCE: 2
SFSQNSRHPS TRQKQFNATN VSNNSNTSND SNVSNKTSNN SNATNKTNNT NDSTNRTNQT  60
NTSQQNFVTQ RSKR                                                    74

SEQ ID NO: 3            moltype = DNA  length = 216
FEATURE                 Location/Qualifiers
source                  1..216
                        mol_type = other DNA
                        organism = synthetic construct
SEQUENCE: 3
agcttcagcc agaatagcag acaccctagc accagacaga aacagtttaa tgccactaat  60
gtgagcaaca acagcaacac cagcaatgac agcaatgtgt ctaacaagac atctaacaac  120
agcaatgcca caaacaagac caacaacaca aatgatagca caaacaggac caaccagacc  180
aataccagcc cccctgtgct gaagagacat cagagg                            216

SEQ ID NO: 4            moltype = DNA  length = 222
FEATURE                 Location/Qualifiers
source                  1..222
                        mol_type = other DNA
                        organism = synthetic construct
SEQUENCE: 4
agcttcagcc agaattctag acaccctagc accagacaga aacagtttaa tgccactaat  60
gtgtctaaca acagcaacac cagcaatgac agcaatgtgt ctaacaagac atctaacaac  120
agcaacgcca caaacaagac caacaacaca aatgatagca caaaccggac caaccagacc  180
aataccagcc agcagaactt cgtgacccag agaagtaaga ga                     222

SEQ ID NO: 5            moltype = AA  length = 1496
```

```
FEATURE                Location/Qualifiers
source                 1..1496
                       mol_type = protein
                       organism = synthetic construct
SEQUENCE: 5
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSPPVLKRH QREITRTTLQ SDQEEIDYDD TISVEMKKED  840
FDIYDEDENQ SPRSFQKKTR HYFIAAVERL WDYGMSSSPH VLRNRAQSGS VPQFKKVVFQ  900
EFTDGSFTQP LYRGELNEHL GLLGPYIRAE VEDNIMVTFR NQASRPYSFY SSLISYEEDQ  960
RQGAEPRKNF VKPNETKTYF WKVQHHMAPT KDEFDCKAWA YFSDVDLEKD VHSGLIGPLL  1020
VCHTNTLNPA HGRQVTVQEF ALFFTIFDET KSWYFTENME RNCRAPCNIQ MEDPTFKENY  1080
RFHAINGYIM DTLPGLVMAQ DQRIRWYLLS MGSNENIHSI HFSGHVFTVR KKEEYKMALY  1140
NLYPGVFETV EMLPSKAGIW RVECLIGEHL HAGMSTLFLV YSNKCQTPLG MASGHIRDFQ  1200
ITASGQYGQW APKLARLHYS GSINAWSTKE PFSWIKVDLL APMIIHGIKT QGARQKFSSL  1260
YISQFIIMYS LDGKKWQTYR GNSTGTLMVF FGNVDSSGIK HNIFNPPIIA RYIRLHPTHY  1320
SIRSTLRMEL MGCDLNSCSM PLGMESKAIS DAQITASSYF TNMFATWSPS KARLHLQGRS  1380
NAWRPQVNNP KEWLQVDFQK TMKVTGVTTQ GVKSLLTSMY VKEFLISSSQ DGHQWTLFFQ  1440
NGKVKVFQGN QDSFTPVVNS LDPPLLTRYL RIHPQSWVHQ IALRMEVLGC EAQDLY       1496

SEQ ID NO: 6           moltype = AA  length = 1498
FEATURE                Location/Qualifiers
source                 1..1498
                       mol_type = protein
                       organism = synthetic construct
SEQUENCE: 6
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSQQNFVTQ RSKREITRTT LQSDQEEIDY DDTISVEMKK  840
EDFDIYDEDE NQSPRSFQKK TRHYFIAAVE RLWDYGMSSS PHVLRNRAQS GSVPQFKKVV  900
FQEFTDGSFT QPLYRGELNE HLGLLGPYIR AEVEDNIMVT FRNQASRPYS FYSSLISYEE  960
DQRQGAEPRK NFVKPNETKT YFWKVQHHMA PTKDEFDCKA WAYFSDVDLE KDVHSGLIGP  1020
LLVCHTNTLN PAHGRQVTVQ EFALFFTIFD ETKSWYFTEN MERNCRAPCN IQMEDPTFKE  1080
NYRFHAINGY IMDTLPGLVM AQDQRIRWYL LSMGSNENIH SIHFSGHVFT VRKKEEYKMA  1140
LYNLYPGVFE TVEMLPSKAG IWRVECLIGE HLHAGMSTLF LVYSNKCQTP LGMASGHIRD  1200
FQITASGQYG QWAPKLARLH YSGSINAWST KEPFSWIKVD LLAPMIIHGI KTQGARQKFS  1260
SLYISQFIIM YSLDGKKWQT YRGNSTGTLM VFFGNVDSSG IKHNIFNPPI IARYIRLHPT  1320
HYSIRSTLRM ELMGCDLNSC SMPLGMESKA ISDAQITASS YFTNMFATWS PSKARLHLQG  1380
RSNAWRPQVN NPKEWLQVDF QKTMKVTGVT TQGVKSLLTS MYVKEFLISS SQDGHQWTLF  1440
FQNGKVKVFQ GNQDSFTPVV NSLDPPLLTR YLRIHPQSWV HQIALRMEVL GCEAQDLY    1498

SEQ ID NO: 7           moltype = DNA  length = 4491
FEATURE                Location/Qualifiers
source                 1..4491
                       mol_type = other DNA
                       organism = synthetic construct
SEQUENCE: 7
gccaccagga ggtactacct gggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag ggggctgagt atgatgacca gactagccag  360
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg ggctctgct ggtgtgtaga  540
gagggcagcc tggctaagga gaagacccag accctgcata agttcatcct gctgtttgct  600
```

```
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatagcag acaccctagc accagacaga aacagtttaa tgccactaat  2280
gtgagcaaca acagcaacac cagcaatgac agcaatgtgt ctaacaagac atctaacaac  2340
agcaatgcca caaacaagac caacaacaca aatgatagca caaacaggac caaccagacc  2400
aataccagcc cccctgtgct gaagagacat cagagggaga tcaccaggac taccctgcag  2460
tctgatcagg aggagattga ctatgatgac acaatctctg tggagatgaa gaaggaggat  2520
tttgacatct atgatgagga tgagaaccag agccccagat cttttcagaa gaagaccaga  2580
cactacttca ttgctgctgt ggagaggctg tgggactatg gcatgagcag cagccctcat  2640
gtgctgagga acagggccca gtctggctct gtgccccagt tcaagaaggt ggtgttccag  2700
gagtttactg atggcagctt cacccagccc ctgtacagag gggagctgaa tgagcacctg  2760
ggcctgctgg gcccttatat cagggctgag gtggaggata acattatggt gactttcagg  2820
aaccaggcct ctaggcccta cagcttctat agcagcctga tctcttatga ggaggatcag  2880
aggcaggggg ctgagcccag aaagaacttt gtgaagccta atgagactaa gacctacttc  2940
tggaaggtcc agcaccacat ggcccccacc aaggatgagt ttgattgcaa ggcctgggcc  3000
tatttctctg atgtggacct ggagaaggat gtccattctg gcctgattgg ccctctgctg  3060
gtgtgccaca ctaacactct gaatcctgcc catggcaggc aggtgactgt ccaggagttt  3120
gccctgttct tcactatctt tgatgagacc aagagctggt actttactga gaacatggag  3180
agaaactgca gggctccttg caatatccag atggaggacc ccaccttcaa ggagaactac  3240
aggtttcatg ccatcaatgg gtacatcatg gacaccctgc ctggcctggt gatggctcag  3300
gaccagagaa tcagatggta tctgctgagc atgggcagca atgagaatat ccacagcatc  3360
cacttctctg gacatgtgtt cactgtgagg aagaaggagg agtacaagat ggctctgtat  3420
aatctgtacc ctggagtgtt tgaaactgtg gagatgctgc cttctaaggc tggcatctgg  3480
agggtggagt gcctgattgg ggagcacctg catgctggca tgagcaccct gttcctggtg  3540
tacagcaaca agtgtcagac cccccctgggc atggcctctg gacacatcag ggacttccag  3600
atcacagcct ctggccagta tggccagtgg gcccccaagc tggccaggct gcattattct  3660
ggcagcatca atgcctggtc taccaaggag ccctttagct ggatcaaggt ggacctgctg  3720
gcccccatga ttatccatgg catcaagacc cagggggcca ggcagaagtt ctctagcctg  3780
tacatcagcc agttcatcat catgtactct ctggatggca agaagtggca gacctacagg  3840
ggcaacagca ctggcacact gatggtgttc tttggcaatg tggacagctc tggcatcaag  3900
cacaacatct tcaatccccc cattatcgct aggtatatta ggctgcatcc cacccactac  3960
agcatcagat ctaccctgag aatggagctg atgggctgtg acctgaactc ttgcagcatg  4020
cccctgggca tggagtctaa ggccatctct gatgcccaga ttactgccag cagctacttc  4080
accaatatgt ttgccacctg gagcccttct aaggccaggc tgcatctgca ggggaggagc  4140
aatgcctgga ggcctcaggt gaacaaccct aaggagtggc tgcaggtgga tttccagaag  4200
accatgaagg tgactggagt gaccacccag ggagtcaaga gcctgctgac cagcatgtat  4260
gtgaaggagt ttctgatcag ctctagccag gatggccacc agtggactct gttctttcag  4320
aatgggaagg tgaaggtgtt tcagggcaat caggactctt tcacccctgt ggtgaacagc  4380
ctggaccccc ccctgctgac cagatacctg agaatccacc cccagagctg ggtgcaccag  4440
atcgccctga ggatggaggt gctgggctgt gaggctcagg atctgtactg a           4491
```

```
SEQ ID NO: 8            moltype = DNA  length = 4497
FEATURE                 Location/Qualifiers
source                  1..4497
                        mol_type = other DNA
                        organism = synthetic construct
SEQUENCE: 8
gccaccagga ggtactacct gggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag ggggctgagt atgatgacca gactagccag  360
agggagaagg aggatgacaa ggtgtttcct ggaggcagcc acacctatgt gtggcaggtg  420
```

-continued

```
ctgaaggaga atggccccat ggcctctgac cccctgtgcc tgacctacag ctacctgagc  480
catgtggatc tggtgaagga cctgaactct ggcctgattg gggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaattctag acaccctagc accagacaga aacagtttaa tgccactaat  2280
gtgtctaaca acagcaacac cagcaatgac agcaatgtgt ctaacaagac atctaacaac  2340
agcaacgcca caaacaagac caacaacaca aatgatagca caaaccggac caaccagacc  2400
aataccagcc agcagaactt cgtgacccag agaagtaaga gagagatcac caggactacc  2460
ctgcagtctg atcaggagga gattgactat gatgacacaa tctctgtgga gatgaagaag  2520
gaggattttg acatctatga tgaggatgag aaccagagcc ccagatcttt tcagaagaag  2580
accagacact acttcattgc tgctgtggag aggctgtggg actatggcat gagcagcagc  2640
cctcatgtgc tgaggaacag ggcccagtct ggctctgtgc cccagttcaa gaaggtggtg  2700
ttccaggagt ttactgatgg cagcttcacc cagcccctgt acagagggga gctgaatgag  2760
cacctgggcc tgctgggccc ttatatcagg gctgaggtgg aggataacat tatggtgact  2820
ttcaggaacc aggcctctag gccctacagc ttctatagca gcctgatctc ttatgaggag  2880
gatcagaggc agggggctga gcccagaaag aactttgtga agcctaatga gactaagacc  2940
tacttctgga aggtccagca ccacatggcc cccaccaagg atgagtttga ttgcaaggcc  3000
tgggcctatt tctctgatgt ggacctggag aaggatgtcc attctggcct gattggccct  3060
ctgctggtgt gccacactaa cactctgaat cctgcccatg gcaggcaggt gactgtccag  3120
gagtttgccc tgttcttcac tatctttgat gagaccaaga gctggtactt tactgagaac  3180
atggagagaa actgcagggc tccttgcaat atccagatgg aggaccccac cttcaaggag  3240
aactacaggt ttcatgccat caatgggtac atcatggaca ccctgcctgg cctggtgatg  3300
gctcaggacc agagaatcag atggtatctg ctgagcatgg gcagcaatga gaatatccac  3360
agcatccact tctctggaca tgtgttcact gtgaggaaga aggaggagta caagatggct  3420
ctgtataatc tgtaccctgg agtgtttgaa actgtggaga tgctgccttc taaggctggc  3480
atctggaggg tggagtgcct gattggggag cacctgcatg ctggcatgag caccctgttc  3540
ctggtgtaca gcaacaagtg tcagaccccc ctgggcatgg cctctggaca catcagggac  3600
ttccagatca cagcctctgg ccagtatggc cagtgggccc ccaagctggc caggctgcat  3660
tattctggca gcatcaatgc ctggtctacc aaggagccct ttagctggat caaggtggac  3720
ctgctggccc ccatgattat ccatggcatc aagacccagg gggccaggca gaagttctct  3780
agcctgtaca tcagccagtt catcatcatg tactctctgg atggcaagaa gtggcagacc  3840
tacaggggca acagcactgg cacactgatg gtgttctttg gcaatgtgga cagctctggc  3900
atcaagcaca acatcttcaa tccccccatt atcgctaggt atattaggct gcatcccacc  3960
cactacagca tcagatctac cctgagaatg gagctgatgg gctgtgacct gaactcttgc  4020
agcatgcccc tgggcatgga gtctaaggcc atctctgatg cccagattac tgccagcagc  4080
tacttcacca atatgtttgc cacctggagc ccttctaagg ccaggctgca tctgcagggg  4140
aggagcaatg cctggaggcc tcaggtgaac aaccctaagg agtggctgca ggtggatttc  4200
cagaagacca tgaaggtgac tggagtgacc acccagggag tcaagagcct gctgaccagc  4260
atgtatgtga aggagtttct gatcagctct agccaggatg gccaccagtg gactctgttc  4320
tttcagaatg ggaaggtgaa ggtgtttcag ggcaatcagg actctttcac ccctgtggtg  4380
aacagcctgg acccccccct gctgaccaga tacctgagaa tccaccccca gagctgggtg  4440
caccagatcg ccctgaggat ggaggtgctg ggctgtgagg ctcaggatct gtactga     4497
```

```
SEQ ID NO: 9           moltype = AA  length = 31
FEATURE                Location/Qualifiers
source                 1..31
                       mol_type = protein
                       organism = synthetic construct
SEQUENCE: 9
SFSQNATNVS NNSNTSNDSN VSPPVLKRHQ R                              31

SEQ ID NO: 10          moltype = AA  length = 21
FEATURE                Location/Qualifiers
```

-continued

```
source                  1..21
                        mol_type = protein
                        organism = synthetic construct
SEQUENCE: 10
SFSQNSRHPS QNPPVLKRHQ R                                          21

SEQ ID NO: 11           moltype = AA  length = 2122
FEATURE                 Location/Qualifiers
source                  1..2122
                        mol_type = protein
                        organism = synthetic construct
SEQUENCE: 11
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNPPVLK RHQREITRTT LQSDQEEIDY DDTISVEMKK  780
EDFDIYDEDE NQSPRSFQKK TRHYFIAAVE RLWDYGMSSS PHVLRNRAQS GSVPQFKKVV  840
FQEFTDGSFT QPLYRGELNE HLGLLGPYIR AEVEDNIMVT FRNQASRPYS FYSSLISYEE  900
DQRQGAEPRK NFVKPNETKT YFWKVQHHMA PTKDEFDCKA WAYFSDVDLE KDVHSGLIGP  960
LLVCHTNTLN PAHGRQVTVQ EFALFFTIFD ETKSWYFTEN MERNCRAPCN IQMEDPTFKE  1020
NYRFHAINGY IMDTLPGLVM AQDQRIRWYL LSMGSNENIH SIHFSGHVFT VRKKEEYKMA  1080
LYNLYPGVFE TVEMLPSKAG IWRVECLIGE HLHAGMSTLF LVYSNKCQTP LGMASGHIRD  1140
FQITASGQYG QWAPKLARLH YSGSINAWST KEPFSWIKVD LLAPMIIHGI KTQGARQKFS  1200
SLYISQFIIM YSLDGKKWQT YRGNSTGTLM VFFGNVDSSG IKHNIFNPPI IARYIRLHPT  1260
HYSIRSTLRM ELMGCDLNSC SMPLGMESKA ISDAQITASS YFTNMFATWS PSKARLHLQG  1320
RSNAWRPQVN NPKEWLQVDF QKTMKVTGVT TQGVKSLLTS MYVKEFLISS SQDGHQWTLF  1380
FQNGKVKVFQ GNQDSFTPVV NSLDPPLLTR YLRIHPQSWV HQIALRMEVL GCEAQDLYEI  1440
TRTTLQSDQE EIDYDDTISV EMKKEDFDIY DEDENQSPRS FQKKTRHYFI AAVERLWDYG  1500
MSSSPHVLRN RAQSGSVPQF KKVVFQEFTD GSFTQPLYRG ELNEHLGLLG PYIRAEVEDN  1560
IMVTFRNQAS RPYSFYSSLI SYEEDQRQGA EPRKNFVKPN ETKTYFWKVQ HHMAPTKDEF  1620
DCKAWAYFSD VDLEKDVHSG LIGPLLVCHT NTLNPAHGRQ VTVQEFALFF TIFDETKSWY  1680
FTENMERNCR APCNIQMEDP TFKENYRFHA INGYIMDTLP GLVMAQDQRI RWYLLSMGSN  1740
ENIHSIHFSG HVFTVRKKEE YKMALYNLYP GVFETVEMLP SKAGIWRVEC LIGEHLHAGM  1800
STLFLVYSNK CQTPLGMASG HIRDFQITAS GQYGQWAPKL ARLHYSGSIN AWSTKEPFSW  1860
IKVDLLAPMI IHGIKTQGAR QKFSSLYISQ FIIMYSLDGK KWQTYRGNST GTLMVFFGNV  1920
DSSGIKHNIF NPPIIARYIR LHPTHYSIRS TLRMELMGCD LNSCSMPLGM ESKAISDAQI  1980
TASSYFTNMF ATWSPSKARL HLQGRSNAWR PQVNNPKEWL QVDFQKTMKV TGVTTQGVKS  2040
LLTSMYVKEF LISSSQDGHQ WTLFFQNGKV KVFQGNQDSF TPVVNSLDPP LLTRYLRIHP  2100
QSWVHQIALR MEVLGCEAQD LY                                         2122

SEQ ID NO: 12           moltype = AA  length = 1455
FEATURE                 Location/Qualifiers
source                  1..1455
                        mol_type = protein
                        organism = synthetic construct
SEQUENCE: 12
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNATNVS NNSNTSNDSN VSPPVLKRHQ REITRTTLQS  780
DQEEIDYDDT ISVEMKKEDF DIYDEDENQS PRSFQKKTRH YFIAAVERLW DYGMSSSPHV  840
LRNRAQSGSV PQFKKVVFQE FTDGSFTQPL YRGELNEHLG LLGPYIRAEV EDNIMVTFRN  900
QASRPYSFYS SLISYEEDQR QGAEPRKNFV KPNETKTYFW KVQHHMAPTK DEFDCKAWAY  960
FSDVDLEKDV HSGLIGPLLV CHTNTLNPAH GRQVTVQEFA LFFTIFDETK SWYFTENMER  1020
NCRAPCNIQM EDPTFKENYR FHAINGYIMD TLPGLVMAQD QRIRWYLLSM GSNENIHSIH  1080
FSGHVFTVRK KEEYKMALYN LYPGVFETVE MLPSKAGIWR VECLIGEHLH AGMSTLFLVY  1140
SNKCQTPLGM ASGHIRDFQI TASGQYGQWA PKLARLHYSG SINAWSTKEP FSWIKVDLLA  1200
PMIIHGIKTQ GARQKFSSLY ISQFIIMYSL DGKKWQTYRG NSTGTLMVFF GNVDSSGIKH  1260
NIFNPPIIAR YIRLHPTHYS IRSTLRMELM GCDLNSCSMP LGMESKAISD AQITASSYFT  1320
NMFATWSPSK ARLHLQGRSN AWRPQVNNPK EWLQVDFQKT MKVTGVTTQG VKSLLTSMYV  1380
KEFLISSSQD GHQWTLFFQN GKVKVFQGNQ DSFTPVVNSL DPPLLTRYLR IHPQSWVHQI  1440
```

```
ALRMEVLGCE AQDLY                                                   1455

SEQ ID NO: 13           moltype = AA  length = 1445
FEATURE                 Location/Qualifiers
source                  1..1445
                        mol_type = protein
                        organism = synthetic construct
SEQUENCE: 13
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS QNPPVLKRHQ REITRTTLQS DQEEIDYDDT  780
ISVEMKKEDF DIYDEDENQS PRSFQKKTRH YFIAAVERLW DYGMSSSPHV LRNRAQSGSV  840
PQFKKVVFQE FTDGSFTQPL YRGELNEHLG LLGPYIRAEV EDNIMVTFRN QASRPYSFYS  900
SLISYEEDQR QGAEPRKNFV KPNETKTYFW KVQHHMAPTK DEFDCKAWAY FSDVDLEKDV  960
HSGLIGPLLV CHTNTLNPAH GRQVTVQEFA LFFTIFDETK SWYFTENMER NCRAPCNIQM  1020
EDPTFKENYR FHAINGYIMD TLPGLVMAQD QRIRWYLLSM GSNENIHSIH FSGHVFTVRK  1080
KEEYKMALYN LYPGVFETVE MLPSKAGIWR VECLIGEHLH AGMSTLFLVY SNKCQTPLGM  1140
ASGHIRDFQI TASGQYGQWA PKLARLHYSG SINAWSTKEP FSWIKVDLLA PMIIHGIKTQ  1200
GARQKFSSLY ISQFIIMYSL DGKKWQTYRG NSTGTLMVFF GNVDSSGIKH NIFNPPIIAR  1260
YIRLHPTHYS IRSTLRMELM GCDLNSCSMP LGMESKAISD AQITASSYFT NMFATWSPSK  1320
ARLHLQGRSN AWRPQVNNPK EWLQVDFQKT MKVTGVTTQG VKSLLTSMYV KEFLISSSQD  1380
GHQWTLFFQN GKVKVFQGNQ DSFTPVVNSL DPPLLTRYLR IHPQSWVHQI ALRMEVLGCE  1440
AQDLY                                                              1445

SEQ ID NO: 14           moltype = AA  length = 1539
FEATURE                 Location/Qualifiers
source                  1..1539
                        mol_type = protein
                        organism = synthetic construct
SEQUENCE: 14
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSQQNFVTQ RRKRGSGATN FSLLKQAGDV EENPGPMQIE  840
LSTCFFLCLL RFCFSEITRT TLQSDQEEID YDDTISVEMK KEDFDIYDED ENQSPRSFQK  900
KTRHYFIAAV ERLWDYGMSS SPHVLRNRAQ SGSVPQFKKV VFQEFTDGSF TQPLYRGELN  960
EHLGLLGPYI RAEVEDNIMV TFRNQASRPY SFYSSLISYE EDQRQGAEPR KNFVKPNETK  1020
TYFWKVQHHM APTKDEFDCK AWAYFSDVDL EKDVHSGLIG PLLVCHTNTL NPAHGRQVTV  1080
QEFALFFTIF DETKSWYFTE NMERNCRAPC NIQMEDPTFK ENYRFHAING YIMDTLPGLV  1140
MAQDQRIRWY LLSMGSNENI HSIHFSGHVF TVRKKEEYKM ALYNLYPGVF ETVEMLPSKA  1200
GIWRVECLIG EHLHAGMSTL FLVYSNKCQT PLGMASGHIR DFQITASGQY GQWAPKLARL  1260
HYSGSINAWS TKEPFSWIKV DLLAPMIIHG IKTQGARQKF SSLYISQFII MYSLDGKKWQ  1320
TYRGNSTGTL MVFFGNVDSS GIKHNIFNPP IIARYIRLHP THYSIRSTLR MELMGCDLNS  1380
CSMPLGMESK AISDAQITAS SYFTNMFATW SPSKARLHLQ GRSNAWRPQV NNPKEWLQVD  1440
FQKTMKVTGV TTQGVKSLLT SMYVKEFLIS SSQDGHQWTL FFQNGKVKVF QGNQDSFTPV  1500
VNSLDPPLLT RYLRIHPQSW VHQIALRMEV LGCEAQDLY                         1539

SEQ ID NO: 15           moltype = DNA  length = 4317
FEATURE                 Location/Qualifiers
source                  1..4317
                        mol_type = other DNA
                        organism = synthetic construct
SEQUENCE: 15
gccaccagga ggtactacct gggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag gggggctgagt atgatgacca gactagccag  360
```

```
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg ggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatccccc tgtgctgaag agacatcaga gggagatcac caggactacc  2280
ctgcagtctg atcaggagga gattgactat gatgacacaa tctctgtgga gatgaagaag  2340
gaggattttg acatctatga tgaggatgag aaccagagcc ccagatcttt tcagaagaag  2400
accagacact acttcattgc tgctgtggag aggctgtggg actatggcat gagcagcagc  2460
cctcatgtgc tgaggaacag ggcccagtct ggctctgtgc cccagttcaa gaaggtggtg  2520
ttccaggagt ttactgatgg cagcttcacc cagcccctgt acagagggga gctgaatgag  2580
cacctgggcc tgctgggccc ttatatcagg gctgaggtgg aggataacat tatggtgact  2640
ttcaggaacc aggcctctag gccctacagc ttctatagca gcctgatctc ttatgaggag  2700
gatcagaggc agggggctga gcccagaaag aactttgtga agcctaatga gactaagacc  2760
tacttctgga aggtccagca ccacatggcc cccaccaagg atgagtttga ttgcaaggcc  2820
tgggcctatt tctctgatgt ggacctggag aaggatgtcc attctggcct gattggccct  2880
ctgctggtgt gccacactaa cactctgaat cctgcccatg gcaggcaggt gactgtccag  2940
gagtttgccc tgttcttcac tatctttgat gagaccaaga gctggtactt tactgagaac  3000
atggagagaa actgcagggc tccttgcaat atccagatgg aggaccccac cttcaaggag  3060
aactacaggt ttcatgccat caatgggtac atcatggaca ccctgcctgg cctggtgatg  3120
gctcaggacc agagaatcag atggtatctg ctgagcatgg gcagcaatga gaatatccac  3180
agcatccact tctctggaca tgtgttcact gtgaggaaga aggaggagta caagatggct  3240
ctgtataatc tgtaccctgg agtgtttgaa actgtggaga tgctgccttc taaggctggc  3300
atctggaggg tggagtgcct gattggggag cacctgcatg ctggcatgag caccctgttc  3360
ctggtgtaca gcaacaagtg tcagaccccc ctgggcatgg cctctggaca catcagggac  3420
ttccagatca cagcctctgg ccagtatggc cagtgggccc ccaagctggc caggctgcat  3480
tattctggca gcatcaatgc ctggtctacc aaggagccct ttagctggat caaggtggac  3540
ctgctggccc ccatgattat ccatggcatc aagacccagg gggccaggca gaagttctct  3600
agcctgtaca tcagccagtt catcatcatg tactctctgg atggcaagaa gtggcagacc  3660
tacaggggca acagcactgg cacactgatg gtgttctttg gcaatgtgga cagctctggc  3720
atcaagcaca acatcttcaa tcccccccatt atcgctaggt atattaggct gcatcccacc  3780
cactacagca tcagatctac cctgagaatg gagctgatgg gctgtgacct gaactcttgc  3840
agcatgcccc tgggcatgga gtctaaggcc atctctgatg cccagattac tgccagcagc  3900
tacttcacca atatgtttgc cacctggagc ccttctaagg ccaggctgca tctgcagggg  3960
aggagcaatg cctggaggcc tcaggtgaac aaccctaagg agtggctgca ggtggatttc  4020
cagaagacca tgaaggtgac tggagtgacc acccagggag tcaagagcct gctgaccagc  4080
atgtatgtga aggagtttct gatcagctct agccaggatg gccaccagtg gactctgttc  4140
tttcagaatg ggaaggtgaa ggtgtttcag ggcaatcagg actctttcac ccctgtggtg  4200
aacagcctgg acccccccct gctgaccaga tacctgagaa tccaccccca gagctgggtg  4260
caccagatcg ccctgaggat ggaggtgctg ggctgtgagg ctcaggatct gtactga     4317
```

```
SEQ ID NO: 16          moltype = DNA  length = 4368
FEATURE                Location/Qualifiers
source                 1..4368
                       mol_type = other DNA
                       organism = synthetic construct
SEQUENCE: 16
gccaccagga ggtactacct gggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag ggggctgagt atgatgacca gactagccag  360
```

```
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg ggctctgct ggtgtgtaga   540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatgccac taatgtgtct aacaacagca acaccagcaa tgacagcaat  2280
gtgtctcccc ctgtgctgaa gagacatcag agggagatca ccaggactac cctgcagtct  2340
gatcaggagg agattgacta tgatgacaca atctctgtgg agatgaagaa ggaggatttt  2400
gacatctatg atgaggatga gaaccagagc cccagatctt ttcagaagaa gaccagacac  2460
tacttcattg ctgctgtgga gaggctgtgg gactatggca tgagcagcag ccctcatgtg  2520
ctgaggaaca gggcccagtc tggctctgtg ccccagttca agaaggtggt gttccaggag  2580
tttactgatg gcagcttcac ccagcccctg tacagagggg agctgaatga gcacctgggc  2640
ctgctgggcc cttatatcag ggctgaggtg gaggataaca ttatggtgac tttcaggaac  2700
caggcctcta ggccctacag cttctatagc agcctgatct cttatgagga ggatcagagg  2760
cagggggctg agcccagaaa gaactttgtg aagcctaatg agactaagac ctacttctgg  2820
aaggtccagc accacatggc ccccaccaag gatgagtttg attgcaaggc ctgggcctat  2880
ttctctgatg tggacctgga gaaggatgtc cattctggcc tgattggccc tctgctggtg  2940
tgccacacta acactctgaa tcctgcccat ggcaggcagg tgactgtcca ggagtttgcc  3000
ctgttcttca ctatctttga tgagaccaag agctggtact ttactgagaa catggagaga  3060
aactgcaggg ctccttgcaa tatccagatg gaggaccccca ccttcaagga gaactacagg  3120
tttcatgcca tcaatgggta catcatggac accctgcctg gcctggtgat ggctcaggac  3180
cagagaatca gatggtatct gctgagcatg ggcagcaatg agaatatcca cagcatccac  3240
ttctctggac atgtgttcac tgtgaggaag aaggaggagt acaagatggc tctgtataat  3300
ctgtaccctg gagtgtttga aactgtggag atgctgcctt ctaaggctgg catctggagg  3360
gtggagtgcc tgattgggga gcacctgcat gctggcatga gcaccctgtt cctggtgtac  3420
agcaacaagt gtcagacccc cctgggcatg gcctctggac acatcaggga cttccagatc  3480
acagcctctg gccagtatgg ccagtgggcc cccaagctgg ccaggctgca ttattctggc  3540
agcatcaatg cctggtctac caaggagccc tttagctgga tcaaggtgga cctgctggcc  3600
cccatgatta tccatggcat caagacccag gggggccaggc agaagttctc tagcctgtac  3660
atcagccagt tcatcatcat gtactctctg gatggcaaga agtggcagac ctacaggggc  3720
aacagcactg gcacactgat ggtgttcttt ggcaatgtgg acagctctgg catcaagcac  3780
aacatcttca atcccccccat tatcgctagg tatattaggc tgcatcccac ccactacagc  3840
atcagatcta ccctgagaat ggagctgatg ggctgtgacc tgaactcttg cagcatgccc  3900
ctgggcatgg agtctaaggc catctctgat gcccagatta ctgccagcag ctacttcacc  3960
aatatgtttg ccacctggag cccttctaag gccaggctgc atctgcaggg gaggagcaat  4020
gcctggaggc ctcaggtgaa caaccctaag gagtggctgc aggtggattt ccagaagacc  4080
atgaaggtga ctggagtgac cacccaggga gtcaagagcc tgctgaccag catgtatgtg  4140
aaggagtttc tgatcagctc tagccaggat ggccaccagt ggactctgtt ctttcagaat  4200
gggaaggtga aggtgtttca gggcaatcag gactctttca cccctgtggt gaacagcctg  4260
gacccccccc tgctgaccag atacctgaga atccaccccc agagctgggt gcaccagatc  4320
gccctgagga tggaggtgct gggctgtgag gctcaggatc tgtactga               4368
```

```
SEQ ID NO: 17          moltype = DNA  length = 4338
FEATURE                Location/Qualifiers
source                 1..4338
                       mol_type = other DNA
                       organism = synthetic construct
SEQUENCE: 17
gccaccagga ggtactacct gggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
```

```
gtgggggtga gctactggaa ggccagcgag ggggctgagt atgatgacca gactagccag  360
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg ggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaattctag acaccctagc caaaaccccc ctgtgctgaa gagacatcag  2280
agggagatca ccaggactac cctgcagtct gatcaggagg agattgacta tgatgacaca  2340
atctctgtgg agatgaagaa ggaggatttt gacatctatg atgaggatga gaaccagagc  2400
cccagatctt ttcagaagaa gaccagacac tacttcattg ctgctgtgga gaggctgtgg  2460
gactatggca tgagcagcag ccctcatgtg ctgaggaaca gggcccagtc tggctctgtg  2520
ccccagttca agaaggtggt gttccaggag tttactgatg gcagcttcac ccagcccctg  2580
tacagagggg agctgaatga gcacctgggc ctgctgggcc cttatatcag ggctgaggtg  2640
gaggataaca ttatggtgac tttcaggaac caggcctcta ggccctacag cttctatagc  2700
agcctgatct cttatgagga ggatcagagg caggggggctg agcccagaaa gaactttgtg  2760
aagcctaatg agactaagac ctacttctgg aaggtccagc accacatggc cccccaccaag  2820
gatgagtttg attgcaaggc ctgggcctat ttctctgatg tggacctgga gaaggatgtc  2880
cattctggcc tgattggccc tctgctggtg tgccacacta acactctgaa tcctgcccat  2940
ggcaggcagg tgactgtcca ggagtttgcc ctgttcttca ctatctttga tgagaccaag  3000
agctggtact ttactgagaa catggagaga aactgcaggg ctccttgcaa tatccagatg  3060
gaggacccca ccttcaagga gaactacagg tttcatgcca tcaatgggta catcatggac  3120
accctgcctg gcctggtgat ggctcaggac cagagaatca gatggtatct gctgagcatg  3180
ggcagcaatg agaatatcca cagcatccac ttctctggac atgtgttcac tgtgaggaag  3240
aaggaggagt acaagatggc tctgtataat ctgtaccctg gagtgtttga aactgtggag  3300
atgctgcctt ctaaggctgg catctggagg gtggagtgcc tgattgggga gcacctgcat  3360
gctggcatga gcaccctgtt cctggtgtac agcaacaagt gtcagacccc cctgggcatg  3420
gcctctggac acatcaggga cttccagatc acagcctctg gccagtatgg ccagtgggcc  3480
cccaagctgg ccaggctgca ttattctggc agcatcaatg cctggtctac caaggagccc  3540
tttagctgga tcaaggtgga cctgctggcc cccatgatta tccatggcat caagacccag  3600
ggggccaggc agaagttctc tagcctgtac atcagccagt tcatcatcat gtactctctg  3660
gatggcaaga agtggcagac ctacaggggc aacagcactg gcacactgat ggtgttcttt  3720
ggcaatgtgg acagctctgg catcaagcac aacatcttca atccccccat tatcgctagg  3780
tatattaggc tgcatcccac ccactacagc atcagatcta ccctgagaat ggagctgatg  3840
ggctgtgacc tgaactcttg cagcatgccc ctgggcatgg agtctaaggc catctctgat  3900
gcccagatta ctgccagcag ctacttcacc aatatgtttg ccacctggag cccttctaag  3960
gccaggctgc atctgcaggg gaggagcaat gcctggaggc ctcaggtgaa caaccctaag  4020
gagtggctgc aggtggattt ccagaagacc atgaaggtga ctggagtgac cacccaggga  4080
gtcaagagcc tgctgaccag catgtatgtg aaggagttcc tgatcagctc tagccaggat  4140
ggccaccagt ggactctgtt ctttcagaat gggaaggtga aggtgtttca gggcaatcag  4200
gactctttca cccctgtggt gaacagcctg gacccccccc tgctgaccag atacctgaga  4260
atccaccccc agagctgggt gcaccagatc gccctgagga tggaggtgct gggctgtgag  4320
gctcaggatc tgtactga                                                4338

SEQ ID NO: 18          moltype = DNA  length = 4620
FEATURE                Location/Qualifiers
source                 1..4620
                       mol_type = other DNA
                       organism = synthetic construct
SEQUENCE: 18
gccaccagga ggtactacct gggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
```

-continued

```
tatgacactg tggtgatcac cctgaagaac atggccagcc atcctgtgag cctgcatgct  300
gtgggggtga gctactggaa ggccagcgag ggggctgagt atgatgacca gactagccag  360
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg gggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatagcag acaccctagc accagacaga aacagtttaa tgccactaat  2280
gtgagcaaca acagcaacac cagcaatgac agcaatgtgt ctaacaagac atctaacaac  2340
agcaatgcca caaacaagac caacaacaca aatgatagca caaacaggac caaccagacc  2400
aataccagcc agcagaactt cgtgacccag agacggaaga gaggctctgg cgccaccaac  2460
tttagcctgc tgaagcaggc aggcgacgtg gaggagaatc ctggaccaat gcagattgag  2520
ctgagcacct gcttcttcct gtgtctgctg aggttctgct tctctgagat caccaggact  2580
accctgcagt ctgatcagga ggagattgac tatgatgaca caatctctgt ggagatgaag  2640
aaggaggatt ttgacatcta tgatgaggat gagaaccaga gccccagatc ttttcagaag  2700
aagaccagac actacttcat tgctgctgtg gagaggctgt gggactatgg catgagcagc  2760
agccctcatg tgctgaggaa cagggcccag tctggctctg tgccccagtt caagaaggtg  2820
gtgttccagg agtttactga tggcagcttc acccagcccc tgtacagagg ggagctgaat  2880
gagcacctgg gcctgctggg cccttatatc agggctgagg tggaggataa cattatggtg  2940
actttcagga accaggcctc taggccctac agcttctata gcagcctgat ctcttatgag  3000
gaggatcaga ggcagggggc tgagcccaga aagaactttg tgaagcctaa tgagactaag  3060
acctacttct ggaaggtcca gcaccacatg gcccccacca aggatgagtt tgattgcaag  3120
gcctgggcct atttctctga tgtggacctg gagaaggatg tccattctgg cctgattggc  3180
cctctgctgg tgtgccacac taacactctg aatcctgccc atggcaggca ggtgactgtc  3240
caggagtttg ccctgttctt cactatcttt gatgagacca agagctggta ctttactgag  3300
aacatggaga gaaactgcag ggctccttgc aatatccaga tggaggaccc caccttcaag  3360
gagaactaca ggtttcatgc catcaatggg tacatcatgg acaccctgcc tggcctggtg  3420
atggctcagg accagagaat cagatggtat ctgctgagca tgggcagcaa tgagaatatc  3480
cacagcatcc acttctctgg acatgtgttc actgtgagga agaaggagga gtacaagatg  3540
gctctgtata atctgtaccc tggagtgttt gaaactgtgg agatgctgcc ttctaaggct  3600
ggcatctgga gggtggagtg cctgattggg gagcacctgc atgctggcat gagcaccctg  3660
ttcctggtgt acagcaacaa gtgtcagacc cccctgggca tggcctctgg acacatcagg  3720
gacttccaga tcacagcctc tggccagtat ggccagtggg cccccaagct ggccaggctg  3780
cattattctg gcagcatcaa tgcctggtct accaaggagc cctttagctg gatcaaggtg  3840
gacctgctgg cccccatgat tatccatggc atcaagaccc aggggggcag gcagaagttc  3900
tctagcctgt acatcagcca gttcatcatc atgtactctc tggatggcaa gaagtggcag  3960
acctacaggg gcaacagcac tggcacactg atggtgttct ttggcaatgt ggacagctct  4020
ggcatcaagc acaacatctt caatcccccc attatcgcta ggtatattag gctgcatccc  4080
acccactaca gcatcagatc taccctgaga atggagctga tgggctgtga cctgaactct  4140
tgcagcatgc ccctgggcat ggagtctaag gccatctctg atgcccagat tactgccagc  4200
agctacttca ccaatatgtt tgccacctgg agcccttcta aggccaggct gcatctgcag  4260
gggaggagca atgcctggag gcctcaggtg aacaacccta aggagtggct gcaggtggat  4320
ttccagaaga ccatgaaggt gactggagtg accacccagg gagtcaagag cctgctgacc  4380
agcatgtatg tgaaggagtt tctgatcagc tctagccagg atggccacca gtggactctg  4440
ttctttcaga atgggaaggt gaaggtgttt cagggcaatc aggactcttt cacccctgtg  4500
gtgaacagcc tggacccccc cctgctgacc agatacctga gaatccaccc ccagagctgg  4560
gtgcaccaga tcgccctgag gatggaggtg ctgggctgtg aggctcagga tctgtactga  4620
```

```
SEQ ID NO: 19          moltype = DNA  length = 5310
FEATURE                Location/Qualifiers
source                 1..5310
                       mol_type = other DNA
                       organism = synthetic construct
```

-continued

SEQUENCE: 19
gccaccagga ggtactacct gggggctgtg gagctgagct gggactacat gcagtctgac 60
ctgggggagc tgcctgtgga tgctaggttc ccccctagag tgcccaagtc cttccccttc 120
aacacttctg tggtgtacaa gaagaccctg tttgtggagt tcactgacca cctgtttaac 180
attgccaagc ccaggccccc ttggatgggc ctgctggggc ccaccatcca ggctgaggtg 240
tatgacactg tggtgatcac cctgaagaac atggccagcc atcctgtgag cctgcatgct 300
gtgggggtga gctactggaa ggccagcgag gggggctgagt atgatgacca gactagccag 360
agggagaagg aggatgacaa ggtgtttcct ggaggcagcc acacctatgt gtggcaggtg 420
ctgaaggaga atggccccat ggcctctgac cccctgtgcc tgacctacag ctacctgagc 480
catgtggatc tggtgaagga cctgaactct ggcctgattg gggctctgct ggtgtgtaga 540
gagggcagcc tggctaagga gaagacccag accctgcata agttcatcct gctgtttgct 600
gtgtttgatg agggcaagag ctggcactct gagaccaaga acagcctgat gcaggatagg 660
gatgctgcct ctgccagggc ttggcccaag atgcacactg tgaatggcta tgtgaatagg 720
agcctgcctg gcctgattgg ctgccacagg aagtctgtgt actggcatgt gattggaatg 780
ggcacaaccc ctgaggtcca tagcatcttc ctggagggcc acactttcct ggtgaggaac 840
cacagacagg cctctctgga gattagcccc atcaccttcc tgactgctca gactctgctg 900
atggacctgg gccagttcct gctgttttgc catattagct ctcaccagca tgatggcatg 960
gaggcctatg tgaaggtgga cagctgccct gaggagcctc agctgaggat gaagaacaat 1020
gaggaggctg aagactatga tgatgacctg actgattctg agatggatgt ggtgaggttt 1080
gatgatgaca atagccccag cttcattcag atcagatctg tggccaaaaa gcaccccaag 1140
acctgggtgc attacattgc tgctgaagag gaggactggg actatgcccc tctggtgctg 1200
gcccctgatg ataggagcta taagagccag tacctgaaca atgggcccca gaggattggc 1260
agaaagtaca agaaggtgag gttcatggct tacactgatg aaaccttcaa aaccagggag 1320
gccatccagc atgagtctgg catcctgggc cctctgctgt atggagaggt gggagacacc 1380
ctgctgatca tcttcaagaa ccaggccagc aggccctaca acatctatcc tcatggcatc 1440
actgatgtga gacctctgta cagcaggagg ctgcctaagg gggtgaaaca cctgaaggac 1500
tttcccatcc tgcctgggga gatcttcaag tataagtgga ctgtgactgt ggaggatggc 1560
cctaccaagt ctgaccccag gtgtctgaca aggtattaca gcagctttgt gaacatggag 1620
agggacctgg cctctggcct gattggccct ctgctgatct gctacaagga gtctgtggac 1680
cagaggggca accagatcat gtctgacaag aggaatgtga tcctgttctc tgtgtttgat 1740
gagaatagga gctggtatct gactgagaac atccagagat tcctgcccaa tcctgctggg 1800
gtgcagctgg aggaccctga gtttcaggcc agcaatatca tgcacagcat caatggctat 1860
gtgtttgaca gcctgcagct gtctgtgtgc ctgcatgagg tggcctactg gtacatcctg 1920
agcattggag cccagactga ttttctgtct gtgttctttt ctggctatac cttcaagcac 1980
aagatggtgt atgaggacac cctgaccctg ttccccttct ctggggagac tgtgttcatg 2040
tctatggaga atcctgggct gtggattctg ggctgccaca actctgattt caggaacagg 2100
ggcatgactg ccctgctgaa ggtgagcagc tgtgacaaga acactgggga ctactatgag 2160
gatagctatg aggacatttc tgcttatctg ctgtctaaga ataatgccat tgagcccagg 2220
agcttcagcc agaatagcag acaccctagc accagacaga aacagtttaa tgccactaat 2280
gtgagcaaca acagcaacac cagcaatgac agcaatgtgt ctaacaagac atctaacaac 2340
agcaatgcca caaacaagac caacaacaca aatgatagca caaacaggac caaccagacc 2400
aataccagcc cccctgtgct gaagagacat cagagggaga tcaccaggac taccctgcag 2460
tctgatcagg aggagattga ctatgatgac acaatctctg tggagatgaa gaaggaggat 2520
tttgacatct atgatgagga tgagaaccag agccccagat cttttcagaa gaagaccaga 2580
cactacttca ttgctgctgt ggagaggctg tgggactatg gcatgagcag cagccctcat 2640
gtgctgagga acagggccca gtctggctct gtgccccagt tcaagaaggt ggtgttccag 2700
gagtttactg atggcagctt cacccagccc ctgtacagag gggagctgaa tgagcacctg 2760
ggcctgctgg gcccttatat cagggctgag gtggaggata acattatggt gactttcagg 2820
aaccaggcct ctaggcccta cagcttctat agcagcctga tctcttatga ggaggatcag 2880
aggcaggggg ctgagcccag aaagaacttt gtgaagccta atgagactaa gacctacttc 2940
tggaaggtcc agcaccacat ggcccccacc aaggatgagt ttgattgcaa ggcctgggcc 3000
tatttctctg atgtggacct ggagaaggat gtccattctg gcctgattgg ccctctgctg 3060
gtgtgccaca ctaacactct gaatcctgcc catggcaggc aggtgactgt ccaggagttt 3120
gccctgttct tcactatctt tgatgagacc aagagctggt actttactga gaacatggag 3180
agaaactgca gggctccttg caatatccag atggaggacc ccaccttcaa ggagaactac 3240
aggtttcatg ccatcaatgg gtacatcatg gacaccctgc ctggcctggt gatggctcag 3300
gaccagagaa tcagatggta tctgctgagc atgggcagca atgagaatat ccacagcatc 3360
cacttctctg gacatgtgtt cactgtgagg aagaaggagg agtacaagat ggctctgtat 3420
aatctgtacc ctggagtgtt tgaaactgtg gagatgctgc cttctaaggc tggcatctgg 3480
agggtggagt gcctgattgg ggagcacctg catgctggca tgagcaccct gttcctggtg 3540
tacagcaaca agtgtcagac ccccctgggc atggcctctg gacacatcag ggacttccag 3600
atcacagcct ctggccagta tggccagtgg gcccccaagc tggccaggct gcattattct 3660
ggcagcatca atgcctggtc taccaaggag ccctttagct ggatcaaggt ggacctgctg 3720
gcccccatga ttatccatgg catcaagacc caggggggcca ggcagaagtt ctctagcctg 3780
tacatcagcc agttcatcat catgtactct ctggatggca agaagtggca gacctacagg 3840
ggcaacagca ctggcacact gatggtgttc tttggcaatg tggacagctc tggcatcaag 3900
cacaacatct tcaatccccc cattatcgct aggtatatta ggctgcatcc cacccactac 3960
agcatcagat ctaccctgag aatggagctg atgggctgtg acctgaactc ttgcagcatg 4020
cccctgggca tggagtctaa ggccatctct gatgcccaga ttactgccag cagctacttc 4080
accaatatgt ttgccacctg gagcccttct aaggccaggc tgcatctgca ggggaggagc 4140
aatgcctgga ggcctcaggt gaacaaccct aaggagtggc tgcaggtgga tttccagaag 4200
accatgaagg tgactggagt gaccacccag ggagtcaaga gcctgctgac cagcatgtat 4260
gtgaaggagt ttctgatcag ctctagccag gatggccacc agtggactct gttctttcag 4320
aatgggaagg tgaaggtgtt tcagggcaat caggactctt tcacccctgt ggtgaacagc 4380
ctggaccccc ccctgctgac cagatacctg agaatccacc cccagagctg ggtgcaccag 4440
atcgccctga ggatggaggt gctgggctgt gaggctcagg atctgtacgg aggcggaggc 4500
tctggaggag gcggctccgg cggaggaggc tctagctcaa gttccaaagc tcctcctcca 4560
agtctgccat ctccaagcag gctccccgga ccatccgata cccctattct gccacaagcc 4620
gagtctaagt atggcccacc ttgtcctcca tgtcctgccc ctccagtggc tggaggacct 4680

```
tctgtgtttc tgtttccccc aaagccaaaa gatacactga tgatttctcg cactcctgag  4740
gtgacttgcg tggtggtggc tgtgagccag gaggatcccg aggtgcagtt caactggtac  4800
gtggacggcg tggaggtgca caacgccaag accaagccca gagaggagca attcaactcc  4860
acctacagag tggtgagcgt gctcaccgtg gtgcaccagg attggctgaa tggcaaggaa  4920
tacaaatgta aggtgagcaa taagggactg ccaagtagca ttgaaaaaac aatttctaaa  4980
gctaaaggac agccaagaga accccaggtt tatactcttc ccccctccca ggaggagatg  5040
accaagaacc aggtgagcct gacctgcctg gtgaagggct ttacccctc cgacatcgcc  5100
gtggagtggg agagcaacgg ccagcccgag aacaactaca agaccacccc ccccgtgctg  5160
gacagcgacg gcagcttctt tctgtattct aaacttacag tcgataaaag cagatggcag  5220
gaaggaaatg tgtttagctg tagcgtgatg catgaagccc tgcacaatca ttacacgcag  5280
aaatccctga gcctgagctt aggtaaatga                                  5310

SEQ ID NO: 20          moltype = AA  length = 1769
FEATURE                Location/Qualifiers
source                 1..1769
                       mol_type = protein
                       organism = synthetic construct
SEQUENCE: 20
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSPPVLKRH QREITRTTLQ SDQEEIDYDD TISVEMKKED  840
FDIYDEDENQ SPRSFQKKTR HYFIAAVERL WDYGMSSSPH VLRNRAQSGS VPQFKKVVFQ  900
EFTDGSFTQP LYRGELNEHL GLLGPYIRAE VEDNIMVTFR NQASRPYSFY SSLISYEEDQ  960
RQGAEPRKNF VKPNETKTYF WKVQHHMAPT KDEFDCKAWA YFSDVDLEKD VHSGLIGPLL  1020
VCHTNTLNPA HGRQVTVQEF ALFFTIFDET KSWYFTENME RNCRAPCNIQ MEDPTFKENY  1080
RFHAINGYIM DTLPGLVMAQ DQRIRWYLLS MGSNENIHSI HFSGHVFTVR KKEEYKMALY  1140
NLYPGVFETV EMLPSKAGIW RVECLIGEHL HAGMSTLFLV YSNKCQTPLG MASGHIRDFQ  1200
ITASGQYGQW APKLARLHYS GSINAWSTKE PFSWIKVDLL APMIIHGIKT QGARQKFSSL  1260
YISQFIIMYS LDGKKWQTYR GNSTGTLMVF FGNVDSSGIK HNIFNPPIIA RYIRLHPTHY  1320
SIRSTLRMEL MGCDLNSCSM PLGMESKAIS DAQITASSYF TNMFATWSPS KARLHLQGRS  1380
NAWRPQVNNP KEWLQVDFQK TMKVTGVTTQ GVKSLLTSMY VKEFLISSSQ DGHQWTLFFQ  1440
NGKVKVFQGN QDSFTPVVNS LDPPLLTRYL RIHPQSWVHQ IALRMEVLGC EAQDLYGGGG  1500
SGGGGSGGGG SSSSSKAPPP SLPSPSRLPG PSDTPILPQA ESKYGPPCPP CPAPPVAGGP  1560
SVFLFPPKPK DTLMISRTPE VTCVVVAVSQ EDPEVQFNWY VDGVEVHNAK TKPREEQFNS  1620
TYRVVSVLTV VHQDWLNGKE YKCKVSNKGL PSSIEKTISK AKGQPREPQV YTLPPSQEEM  1680
TKNQVSLTCL VKGFYPSDIA VEWESNGQPE NNYKTTPPVL DSDGSFFLYS KLTVDKSRWQ  1740
EGNVFSCSVM HEALHNHYTQ KSLSLSLGK                                   1769

SEQ ID NO: 21          moltype = AA  length = 1496
FEATURE                Location/Qualifiers
source                 1..1496
                       mol_type = protein
                       organism = synthetic construct
SEQUENCE: 21
ATRRYYLGAV ELSWDYMQSD LGELPVDARF PPRVPKSFPF NTSVVYKKTL FVEFTDHLFN  60
IAKPRPPWMG LLGPTIQAEV YDTVVVTLKN MASHPVSLHA VGVSYWKSSE GAEYDDQTSQ  120
REKEDDKVFP GKSHTYVWQV LKENGPTASD PPCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSPPVLKRH QREITRTTLQ SDQEEIDYDD TISVEMKKED  840
FDIYDEDENQ SPRSFQKKTR HYFIAAVERL WDYGMSSSPH VLRNRAQSGS VPQFKKVVFQ  900
EFTDGSFTQP LYRGELNEHL GLLGPYIRAE VEDNIMVTFR NQASRPYSFY SSLISYEEDQ  960
RQGAEPRKNF VKPNETKTYF WKVQHHMAPT KDEFDCKAWA YFSDVDLEKD VHSGLIGPLL  1020
VCHTNTLNPA HGRQVTVQEF ALFFTIFDET KSWYFTENME RNCRAPCNIQ MEDPTFKENY  1080
RFHAINGYIM DTLPGLVMAQ DQRIRWYLLS MGSNENIHSI HFSGHVFTVR KKEEYKMALY  1140
NLYPGVFETV EMLPSKAGIW RVECLIGEHL HAGMSTLFLV YSNKCQTPLG MASGHIRDFQ  1200
ITASGQYGQW APKLARLHYS GSINAWSTKE PFSWIKVDLL APMIIHGIKT QGARQKFSSL  1260
YISQFIIMYS LDGKKWQTYR GNSTGTLMVF FGNVDSSGIK HNIFNPPIIA RYIRLHPTHY  1320
SIRSTLRMEL MGCDLNSCSM PLGMESKAIS DAQITASSYF TNMFATWSPS KARLHLQGRS  1380
NAWRPQVNNP KEWLQVDFQK TMKVTGVTTQ GVKSLLTSMY VKEFLISSSQ DGHQWTLFFQ  1440
```

-continued

```
NGKVKVFQGN QDSFTPVVNS LDPPLLTRYL RIHPQSWVHQ IALRMEVLGC EAQDLY      1496

SEQ ID NO: 22           moltype = DNA  length = 4491
FEATURE                 Location/Qualifiers
source                  1..4491
                        mol_type = other DNA
                        organism = synthetic construct
SEQUENCE: 22
gccaccagga ggtactacct gggggctgtg gagctgagct gggactacat gcagtctgac  60
ctgggggagc tgcctgtgga tgctaggttc cccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtggtgac cctgaagaac atggccagcc atcctgtgag cctgcatgct  300
gtgggggtga gctactggaa gagcagcgag ggggctgagt atgatgacca gactagccag  360
agggagaagg aggatgacaa ggtgtttcct ggaaagagcc acacctatgt gtggcaggtg  420
ctgaaggaga atggccccac agcctctgac cccccttgcc tgacctacag ctacctgagc  480
catgtggatc tggtgaagga cctgaactct ggcctgattg gggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatagcag acaccctagc accagacaga aacagtttaa tgccactaat  2280
gtgagcaaca acagcaacac cagcaatgac agcaatgtgt ctaacaagac atctaacaac  2340
agcaatgcca caaacaagac caacaacaca aatgatagca caaacaggac caaccagacc  2400
aataccagcc cccctgtgct gaagagacat cagagggaga tcaccaggac taccctgcag  2460
tctgatcagg aggagattga ctatgatgac acaatctctg tggagatgaa gaaggaggat  2520
tttgacatct atgatgagga tgagaaccag agccccagat cttttcagaa gaagaccaga  2580
cactacttca ttgctgctgt ggagaggctg tgggactatg gcatgagcag cagccctcat  2640
gtgctgagga acagggccca gtctggctct gtgccccagt tcaagaaggt ggtgttccag  2700
gagtttactg atggcagctt cacccagccc ctgtacagag gggagctgaa tgagcacctg  2760
ggcctgctgg gcccttatat cagggctgag gtggaggata acattatggt gactttcagg  2820
aaccaggcct ctaggcccta cagcttctat agcagcctga tctcttatga ggaggatcag  2880
aggcaggggg ctgagcccag aaagaacttt gtgaagccta atgagactaa gacctacttc  2940
tggaaggtcc agcaccacat ggcccccacc aaggatgagt ttgattgcaa ggcctgggcc  3000
tatttctctg atgtggacct ggagaaggat gtccattctg gcctgattgg ccctctgctg  3060
gtgtgccaca ctaacactct gaatcctgcc catggcaggc aggtgactgt ccaggagttt  3120
gccctgttct tcactatctt tgatgagacc aagagctggt actttactga gaacatggag  3180
agaaactgca gggctccttg caatatccag atggaggacc ccaccttcaa ggagaactac  3240
aggtttcatg ccatcaatgg gtacatcatg gacaccctgc ctggcctggt gatggctcag  3300
gaccagagaa tcagatggta tctgctgagc atgggcagca atgagaatat ccacagcatc  3360
cacttctctg gacatgtgtt cactgtgagg aagaaggagg agtacaagat ggctctgtat  3420
aatctgtacc ctggagtgtt tgaaactgtg gagatgctgc cttctaaggc tggcatctgg  3480
agggtggagt gcctgattgg ggagcacctg catgctggca tgagcaccct gttcctggtg  3540
tacagcaaca agtgtcagac ccccctgggc atggcctctg gacacatcag ggacttccag  3600
atcacagcct ctggccagta tggccagtgg gcccccaagc tggccaggct gcattattct  3660
ggcagcatca atgcctggtc taccaaggag ccctttagct ggatcaaggt ggacctgctg  3720
gcccccatga ttatccatgg catcaagacc caggggggcca ggcagaagtt ctctagcctg  3780
tacatcagcc agttcatcat catgtactct ctggatggca agaagtggca gacctacagg  3840
ggcaacagca ctggcacact gatggtgttc tttggcaatg tggacagctc tggcatcaag  3900
cacaacatct tcaatccccc cattatcgct aggtatatta ggctgcatcc cacccactac  3960
agcatcagat ctaccctgag aatggagctg atgggctgtg acctgaactc ttgcagcatg  4020
cccctgggca tggagtctaa ggccatctct gatgcccaga ttactgccag cagctacttc  4080
accaatatgt ttgccacctg gagcccttct aaggccaggc tgcatctgca ggggaggagc  4140
aatgcctgga ggcctcaggt gaacaaccct aaggagtggc tgcaggtgga tttccagaag  4200
accatgaagg tgactggagt gaccacccag ggagtcaaga gcctgctgac cagcatgtat  4260
```

```
gtgaaggagt ttctgatcag ctctagccag gatggccacc agtggactct gttctttcag  4320
aatgggaagg tgaaggtgtt tcagggcaat caggactctt tcacccctgt ggtgaacagc  4380
ctggacccccc ccctgctgac cagatacctg agaatccacc cccagagctg ggtgcaccag  4440
atcgccctga ggatggaggt gctgggctgt gaggctcagg atctgtactg a           4491

SEQ ID NO: 23           moltype = AA  length = 1498
FEATURE                 Location/Qualifiers
source                  1..1498
                        mol_type = protein
                        organism = synthetic construct
SEQUENCE: 23
ATRRYYLGAV ELSWDYMQSD LGELPVDARF PPRVPKSFPF NTSVVYKKTL FVEFTDHLFN  60
IAKPRPPWMG LLGPTIQAEV YDTVVVTLKN MASHPVSLHA VGVSYWKSSE GAEYDDQTSQ  120
REKEDDKVFP GKSHTYVWQV LKENGPTASD PPCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSQQNFVTQ RSKREITRTT LQSDQEEIDY DDTISVEMKK  840
EDFDIYDEDE NQSPRSFQKK TRHYFIAAVE RLWDYGMSSS PHVLRNRAQS GSVPQFKKVV  900
FQEFTDGSFT QPLYRGELNE HLGLLGPYIR AEVEDNIMVT FRNQASRPYS FYSSLISYEE  960
DQRQGAEPRK NFVKPNETKT YFWKVQHHMA PTKDEFDCKA WAYFSDVDLE KDVHSGLIGP  1020
LLVCHTNTLN PAHGRQVTVQ EFALFFTIFD ETKSWYFTEN MERNCRAPCN IQMEDPTFKE  1080
NYRFHAINGY IMDTLPGLVM AQDQRIRWYL LSMGSNENIH SIHFSGHVFT VRKKEEYKMA  1140
LYNLYPGVFE TVEMLPSKAG IWRVECLIGE HLHAGMSTLF LVYSNKCQTP LGMASGHIRD  1200
FQITASGQYG QWAPKLARLH YSGSINAWST KEPFSWIKVD LLAPMIIHGI KTQGARQKFS  1260
SLYISQFIIM YSLDGKKWQT YRGNSTGTLM VFFGNVDSSG IKHNIFNPPI IARYIRLHPT  1320
HYSIRSTLRM ELMGCDLNSC SMPLGMESKA ISDAQITASS YFTNMFATWS PSKARLHLQG  1380
RSNAWRPQVN NPKEWLQVDF QKTMKVTGVT TQGVKSLLTS MYVKEFLISS SQDGHQWTLF  1440
FQNGKVKVFQ GNQDSFTPVV NSLDPPLLTR YLRIHPQSWV HQIALRMEVL GCEAQDLY    1498

SEQ ID NO: 24           moltype = DNA  length = 4497
FEATURE                 Location/Qualifiers
source                  1..4497
                        mol_type = other DNA
                        organism = synthetic construct
SEQUENCE: 24
gccaccagga ggtactacct gggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtggtgac cctgaagaac atggccagcc atcctgtgag cctgcatgct  300
gtgggggtga gctactggaa gagcagcgag gggctgagt atgatgacca gactagccag  360
agggagaagg aggatgacaa ggtgtttcct ggaaagagcc acacctatgt gtggcaggtg  420
ctgaaggaga atggccccac agcctctgac ccccccttgcc tgacctacag ctacctgagc  480
catgtggatc tggtgaagga cctgaactct ggcctgattg gggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
```

```
gatagctatg aggacatttc tgcttatctg ctgtctaaga ataatgccat tgagcccagg  2220
agcttcagcc agaattctag acaccctagc accagacaga aacagtttaa tgccactaat  2280
gtgtctaaca acagcaacac cagcaatgac agcaatgtgt ctaacaagac atctaacaac  2340
agcaacgcca caaacaagac caacaacaca aatgatagca caaaccggac caaccagacc  2400
aataccagcc agcagaactt cgtgacccag agaagtaaga gagagatcac caggactacc  2460
ctgcagtctg atcaggagga gattgactat gatgacacaa tctctgtgga gatgaagaag  2520
gaggattttg acatctatga tgaggatgag aaccagagcc ccagatcttt tcagaagaag  2580
accagacact acttcattgc tgctgtggag aggctgtggg actatggcat gagcagcagc  2640
cctcatgtgc tgaggaacag ggcccagtct ggctctgtgc cccagttcaa gaaggtggtg  2700
ttccaggagt ttactgatgg cagcttcacc cagcccctgt acagagggga gctgaatgag  2760
cacctgggcc tgctgggccc ttatatcagg gctgaggtgg aggataacat tatggtgact  2820
ttcaggaacc aggcctctag gccctacagc ttctatagca gcctgatctc ttatgaggag  2880
gatcagaggc agggggctga gcccagaaag aactttgtga agcctaatga gactaagacc  2940
tacttctgga aggtccagca ccacatggcc cccaccaagg atgagtttga ttgcaaggcc  3000
tgggcctatt tctctgatgt ggacctggag aaggatgtcc attctggcct gattggccct  3060
ctgctggtgt gccacactaa cactctgaat cctgcccatg gcaggcaggt gactgtccag  3120
gagtttgccc tgttcttcac tatctttgat gagaccaaga gctggtactt tactgagaac  3180
atggagagaa actgcagggc tccttgcaat atccagatgg aggaccccac cttcaaggag  3240
aactacaggt ttcatgccat caatgggtac atcatggaca ccctgcctgg cctggtgatg  3300
gctcaggacc agagaatcag atggtatctg ctgagcatgg gcagcaatga gaatatccac  3360
agcatccact tctctggaca tgtgttcact gtgaggaaga aggaggagta caagatggct  3420
ctgtataatc tgtaccctgg agtgtttgaa actgtggaga tgctgccttc taaggctggc  3480
atctggaggg tggagtgcct gattggggag cacctgcatg ctggcatgag caccctgttc  3540
ctggtgtaca gcaacaagtg tcagaccccc ctgggcatgg cctctggaca catcagggac  3600
ttccagatca cagcctctgg ccagtatggc cagtgggccc ccaagctggc caggctgcat  3660
tattctggca gcatcaatgc ctggtctacc aaggagccct ttagctggat caaggtggac  3720
ctgctggccc ccatgattat ccatggcatc aagacccagg gggccaggca gaagttctct  3780
agcctgtaca tcagccagtt catcatcatg tactctctgg atggcaagaa gtggcagacc  3840
tacaggggca acagcactgg cacactgatg gtgttctttg gcaatgtgga cagctctggc  3900
atcaagcaca acatcttcaa tcccccccatt atcgctaggt atattaggct gcatcccacc  3960
cactacagca tcagatctac cctgagaatg gagctgatgg gctgtgacct gaactcttgc  4020
agcatgcccc tgggcatgga gtctaaggcc atctctgatg cccagattac tgccagcagc  4080
tacttcacca atatgtttgc cacctggagc ccttctaagg ccaggctgca tctgcagggg  4140
aggagcaatg cctggaggcc tcaggtgaac aaccctaagg agtggctgca ggtggatttc  4200
cagaagacca tgaaggtgac tggagtgacc acccagggag tcaagagcct gctgaccagc  4260
atgtatgtga aggagtttct gatcagctct agccaggatg gccaccagtg gactctgttc  4320
tttcagaatg ggaaggtgaa ggtgtttcag ggcaatcagg actctttcac ccctgtggtg  4380
aacagcctgg accccccccct gctgaccaga tacctgagaa tccacccccca gagctgggtg  4440
caccagatcg ccctgaggat ggaggtgctg ggctgtgagg ctcaggatct gtactga     4497
```

```
SEQ ID NO: 25          moltype = DNA  length = 5928
FEATURE                Location/Qualifiers
source                 1..5928
                       mol_type = other DNA
                       organism = synthetic construct
SEQUENCE: 25
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg gggggagctgc ctgtggatgc taggttcccc cctagagtgc  1260
ccaagtcctt ccccttcaac acttctgtgg tgtacaagaa gaccctgttt gtggagttca  1320
ctgaccacct gtttaacatt gccaagccca ggcccccttg gatgggcctg ctggggccca  1380
ccatccaggc tgaggtgtat gacactgtgg tgatcaccct gaagaacatg gccagccatc  1440
ctgtgagcct gcatgctgtg ggggtgagct actggaaggc cagcgagggg gctgagtatg  1500
atgaccagac tagccagagg gagaaggagg atgacaaggt gtttcctgga ggcagccaca  1560
cctatgtgtg gcaggtgctg aaggagaatg gccccatggc ctctgacccc ctgtgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaacccctg aggtccatag catcttcctg gagggccaca  1980
```

-continued

```
ctttcctggt gaggaaccac agacaggcct ctctggagat tagccccatc accttcctga  2040
ctgctcagac tctgctgatg gacctgggcc agttcctgct gttttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga atagcagaca ccctagcacc agacagaaac  3420
agtttaatgc cactaatgtg agcaacaaca gcaacaccag caatgacagc aatgtgtcta  3480
acaagacatc taacaacagc aatgccacaa acaagaccaa caacacaaat gatagcacaa  3540
acaggaccaa ccagaccaat accagccccc ctgtgctgaa gagacatcag agggagatca  3600
ccaggactac cctgcagtct gatcaggagg agattgacta tgatgacaca atctctgtgg  3660
agatgaagaa ggaggatttt gacatctatg atgaggatga gaaccagagc cccagatctt  3720
ttcagaagaa gaccagacac tacttcattg ctgctgtgga gaggctgtgg gactatggca  3780
tgagcagcag ccctcatgtg ctgaggaaca gggcccagtc tggctctgtg ccccagttca  3840
agaaggtggt gttccaggag tttactgatg gcagcttcac ccagcccctg tacagagggg  3900
agctgaatga gcacctgggc ctgctgggcc cttatatcag ggctgaggtg gaggataaca  3960
ttatggtgac tttcaggaac caggcctcta ggccctacag cttctatagc agcctgatct  4020
cttatgagga ggatcagagg caggggctg agcccagaaa gaactttgtg aagcctaatg  4080
agactaagac ctacttctgg aaggtccagc accacatggc cccaccaag gatgagtttg  4140
attgcaaggc ctgggcctat ttctctgatg tggacctgga gaaggatgtc cattctggcc  4200
tgattggccc tctgctggtg tgccacacta acactctgaa tcctgcccat ggcaggcagg  4260
tgactgtcca ggagtttgcc ctgttcttca ctatctttga tgagaccaag agctggtact  4320
ttactgagaa catggagaga aactgcaggg ctccttgcaa tatccagatg gaggacccca  4380
ccttcaagga gaactacagg tttcatgcca tcaatgggta catcatggac accctgcctg  4440
gcctggtgat ggctcaggac cagagaatca gatggtatct gctgagcatg ggcagcaatg  4500
agaatatcca cagcatccac ttctctggac atgtgttcac tgtgaggaag aaggaggagt  4560
acaagatggc tctgtataat ctgtaccctg gagtgtttga aactgtggag atgctgcctt  4620
ctaaggctgg catctggagg gtggagtgcc tgattgggga gcacctgcat gctggcatga  4680
gcaccctgtt cctggtgtac agcaacaagt gtcagacccc cctgggcatg gcctctggac  4740
acatcaggga cttccagatc acagcctctg gccagtatgg ccagtgggcc cccaagctgg  4800
ccaggctgca ttattctggc agcatcaatg cctggtctac caaggagccc tttagctgga  4860
tcaaggtgga cctgctggcc cccatgatta tccatggcat caagacccag gggccaggc  4920
agaagttctc tagcctgtac atcagccagt tcatcatcat gtactctctg gatggcaaga  4980
agtggcagac ctacaggggc aacagcactg gcacactgat ggtgttcttt ggcaatgtgg  5040
acagctctgg catcaagcac aacatcttca atcccccat tatcgctagg tatattaggc  5100
tgcatcccac ccactacagc atcagatcta ccctgagaat ggagctgatg ggctgtgacc  5160
tgaactcttg cagcatgccc ctgggcatgg agtctaaggc catctctgat gcccagatta  5220
ctgccagcag ctacttcacc aatatgtttg ccacctggag cccttctaag gccaggctgc  5280
atctgcaggg gaggagcaat gcctggaggc ctcaggtgaa caaccctaag gagtggctgc  5340
aggtggattt ccagaagacc atgaaggtga ctggagtgac cacccaggga gtcaagagcc  5400
tgctgaccag catgtatgtg aaggagtttc tgatcagctc tagccaggat ggccaccagt  5460
ggactctgtt ctttcagaat gggaaggtga aggtgtttca gggcaatcag gactctttca  5520
cccctgtggt gaacagcctg gacccccccc tgctgaccag atacctgaga atccaccccc  5580
agagctgggt gcaccagatc gccctgagga tggaggtgct gggctgtgag gctcaggatc  5640
tgtactgaga tatctctaga gtcgacagta ctggtgatca gcctcgactg tgccttctag  5700
ttgccagcca tctgttgttt gcccctcccc cgtgccttcc ttgaccctgg aaggtgccac  5760
tcccactgtc ctttcctaat aaaatgagga aattgcatcg cattgtctga gtaggtgtca  5820
ttctattctg gggggtgggg tggggcagga cagcaagggg gaggattggg aagacaatag  5880
caggcatgct ggggatgcgg tgggctctat ggaaccagct ggggcccg  5928
```

```
SEQ ID NO: 26          moltype = DNA  length = 5934
FEATURE                Location/Qualifiers
source                 1..5934
                       mol_type = other DNA
                       organism = synthetic construct
SEQUENCE: 26
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
```

-continued

```
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gcccccatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg gggagctgc ctgtggatgc taggttcccc cctagagtgc  1260
ccaagtcctt ccccttcaac acttctgtgg tgtacaagaa gaccctgttt gtggagttca  1320
ctgaccacct gtttaacatt gccaagccca ggcccccttg gatgggcctg ctggggccca  1380
ccatccaggc tgaggtgtat gacactgtgg tgatcaccct gaagaacatg gccagccatc  1440
ctgtgagcct gcatgctgtg gggtgagct actggaaggc cagcgagggg gctgagtatg  1500
atgaccagac tagccagagg gagaaggagg atgacaaggt gtttcctgga ggcagccaca  1560
cctatgtgtg gcaggtgctg aaggagaatg gccccatggc ctctgacccc ctgtgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaacccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gttttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga attctagaca ccctagcacc agacagaaac  3420
agtttaatgc cactaatgtg tctaacaaca gcaacaccag caatgacagc aatgtgtcta  3480
acaagacatc taacaacagc aacgccacaa acaagaccaa caacacaaat gatagcacaa  3540
accggaccaa ccagaccaat accagccagc agaacttcgt gacccagaga agtaagagag  3600
agatcaccag gactaccctg cagtctgatc aggaggagat tgactatgat gacacaatct  3660
ctgtggagat gaagaaggag gattttgaca tctatgatga ggatgagaac cagagcccca  3720
gatcttttca gaagaagacc agacactact tcattgctgc tgtggagagg ctgtgggact  3780
atggcatgag cagcagccct catgtgctga ggaacagggc ccagtctggc tctgtgcccc  3840
agttcaagaa ggtggtgttc caggagttta ctgatggcag cttcacccag cccctgtaca  3900
gaggggagct gaatgagcac ctgggcctgc tgggccctta tatcagggct gaggtggagg  3960
ataacattat ggtgactttc aggaaccagg cctctaggcc ctacagcttc tatagcagcc  4020
tgatctctta tgaggaggat cagaggcagg gggctgagcc cagaaagaac tttgtgaagc  4080
ctaatgagac taagacctac ttctggaagg tccagcacca catggccccc accaaggatg  4140
agtttgattg caaggcctgg gcctatttct ctgatgtgga cctggagaag gatgtccatt  4200
ctggcctgat tggccctctg ctggtgtgcc acactaacac tctgaatcct gcccatggca  4260
ggcaggtgac tgtccaggag tttgccctgt tcttcactat ctttgatgag accaagagct  4320
ggtactttac tgagaacatg gagagaaact gcagggctcc ttgcaatatc cagatggagg  4380
accccacctt caaggagaac tacaggtttc atgccatcaa tgggtacatc atggacaccc  4440
tgcctggcct ggtgatggct caggaccaga gaatcagatg gtatctgctg agcatgggca  4500
gcaatgagaa tatccacagc atccacttct ctggacatgt gttcactgtg aggaagaagg  4560
aggagtacaa gatggctctg tataatctgt accctggagt gtttgaaact gtggagatgc  4620
tgccttctaa ggctggcatc tggagggtgg agtgcctgat tggggagcac ctgcatgctg  4680
gcatgagcac cctgttcctg gtgtacagca acaagtgtca gacccccctg ggcatggcct  4740
ctggacacat cagggacttc cagatcacag cctctggcca gtatggccag tgggccccca  4800
agctggccag gctgcattat tctggcagca tcaatgcctg gtctaccaag gagcccttta  4860
gctggatcaa ggtggacctg ctggccccca tgattatcca tggcatcaag acccaggggg  4920
ccaggcagaa gttctctagc ctgtacatca gccagttcat catcatgtac tctctggatg  4980
gcaagaagtg gcagacctac aggggcaaca gcactggcac actgatggtg ttctttggca  5040
atgtggacag ctctggcatc aagcacaaca tcttcaatcc ccccattatc gctaggtata  5100
```

```
ttaggctgca tcccacccac tacagcatca gatctaccct gagaatggag ctgatgggct  5160
gtgacctgaa ctcttgcagc atgcccctgg gcatggagtc taaggccatc tctgatgccc  5220
agattactgc cagcagctac ttcaccaata tgtttgccac ctggagccct tctaaggcca  5280
ggctgcatct gcaggggagg agcaatgcct ggaggcctca ggtgaacaac cctaaggagt  5340
ggctgcaggt ggatttccag aagaccatga aggtgactgg agtgaccacc cagggagtca  5400
agagcctgct gaccagcatg tatgtgaagg agtttctgat cagctctagc caggatggcc  5460
accagtggac tctgttcttt cagaatggga aggtgaaggt gtttcagggc aatcaggact  5520
ctttcacccc tgtggtgaac agcctggacc ccccccctgct gaccagatac ctgagaatcc  5580
acccccagag ctgggtgcac cagatcgccc tgaggatgga ggtgctgggc tgtgaggctc  5640
aggatctgta ctgagatatc tctagagtcg acagtactgg tgatcagcct cgactgtgcc  5700
ttctagttgc cagccatctg ttgtttgccc ctcccccgtg ccttccttga ccctggaagg  5760
tgccactccc actgtccttt cctaataaaa tgaggaaatt gcatcgcatt gtctgagtag  5820
gtgtcattct attctggggg gtggggtggg gcaggacagc aagggggagg attgggaaga  5880
caatagcagg catgctgggg atgcggtggg ctctatggaa ccagctgggg cccg        5934

SEQ ID NO: 27          moltype = DNA  length = 5928
FEATURE                Location/Qualifiers
source                 1..5928
                       mol_type = other DNA
                       organism = synthetic construct
SEQUENCE: 27
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg gggggagctgc ctgtggatgc taggttcccc cctagagtgc  1260
ccaagtcctt ccccttcaac acttctgtgg tgtacaagaa gaccctgttt gtggagttca  1320
ctgaccacct gtttaacatt gccaagccca ggccccccttg gatgggcctg ctggggccca  1380
ccatccaggc tgaggtgtat gacactgtgg tggtgaccct gaagaacatg gccagccatc  1440
ctgtgagcct gcatgctgtg ggggtgagct actggaagag cagcgagggg gctgagtatg  1500
atgaccagac tagccagagg gagaaggagg atgacaaggt gtttcctgga aagagccaca  1560
cctatgtgtg gcaggtgctg aaggagaatg gccccacagc ctctgacccc ccttgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaacccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gttttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga atagcagaca ccctagcacc agacagaaac  3420
agtttaatgc cactaatgtg agcaacaaca gcaacaccag caatgacagc aatgtgtcta  3480
```

```
acaagacatc taacaacagc aatgccacaa acaagaccaa caacacaaat gatagcacaa  3540
acaggaccaa ccagaccaat accagccccc ctgtgctgaa gagacatcag agggagatca  3600
ccaggactac cctgcagtct gatcaggagg agattgacta tgatgacaca atctctgtgg  3660
agatgaagaa ggaggatttt gacatctatg atgaggatga gaaccagagc cccagatctt  3720
ttcagaagaa gaccagacac tacttcattg ctgctgtgga gaggctgtgg gactatggca  3780
tgagcagcag ccctcatgtg ctgaggaaca gggcccagtc tggctctgtg ccccagttca  3840
agaaggtggt gttccaggag tttactgatg gcagcttcac ccagcccctg tacagagggg  3900
agctgaatga gcacctgggc ctgctgggcc cttatatcag ggctgaggtg gaggataaca  3960
ttatggtgac tttcaggaac caggcctcta ggccctacag cttctatagc agcctgatct  4020
cttatgagga ggatcagagg caggggggctg agcccagaaa gaactttgtg aagcctaatg  4080
agactaagac ctacttctgg aaggtccagc accacatggc ccccaccaag gatgagtttg  4140
attgcaaggc ctgggcctat ttctctgatg tggacctgga gaaggatgtc cattctggcc  4200
tgattggccc tctgctggtg tgccacacta acactctgaa tcctgcccat ggcaggcagg  4260
tgactgtcca ggagtttgcc ctgttcttca ctatctttga tgagaccaag agctggtact  4320
ttactgagaa catggagaga aactgcaggg ctccttgcaa tatccagatg gaggacccca  4380
ccttcaagga gaactacagg tttcatgcca tcaatgggta catcatggac accctgcctg  4440
gcctggtgat ggctcaggac cagagaatca gatggtatct gctgagcatg ggcagcaatg  4500
agaatatcca cagcatccac ttctctggac atgtgttcac tgtgaggaag aaggaggagt  4560
acaagatggc tctgtataat ctgtaccctg gagtgtttga aactgtggag atgctgcctt  4620
ctaaggctgg catctggagg gtggagtgcc tgattgggga gcacctgcat gctggcatga  4680
gcaccctgtt cctggtgtac agcaacaagt gtcagacccc cctgggcatg gcctctggac  4740
acatcaggga cttccagatc acagcctctg gccagtatgg ccagtgggcc cccaagctgg  4800
ccaggctgca ttattctggc agcatcaatg cctggtctac caaggagccc tttagctgga  4860
tcaaggtgga cctgctggcc cccatgatta tccatggcat caagacccag gggggccaggc  4920
agaagttctc tagcctgtac atcagccagt tcatcatcat gtactctctg gatggcaaga  4980
agtggcagac ctacaggggc aacagcactg gcacactgat ggtgttcttt ggcaatgtgg  5040
acagctctgg catcaagcac aacatcttca atccccccat tatcgctagg tatattaggc  5100
tgcatcccac ccactacagc atcagatcta ccctgagaat ggagctgatg ggctgtgacc  5160
tgaactcttg cagcatgccc ctgggcatgg agtctaaggc catctctgat gcccagatta  5220
ctgccagcag ctacttcacc aatatgtttg ccacctggag cccttctaag gccaggctgc  5280
atctgcaggg gaggagcaat gcctggaggc ctcaggtgaa caaccctaag gagtggctgc  5340
aggtggattt ccagaagacc atgaaggtga ctggagtgac cacccaggga gtcaagagcc  5400
tgctgaccag catgtatgtg aaggagtttc tgatcagctc tagccaggat ggccaccagt  5460
ggactctgtt ctttcagaat gggaaggtga aggtgtttca gggcaatcag gactctttca  5520
cccctgtggt gaacagcctg gacccccccc tgctgaccag atacctgaga atccaccccc  5580
agagctgggt gcaccagatc gccctgagga tggaggtgct gggctgtgag gctcaggatc  5640
tgtactgaga tatctctaga gtcgacagta ctggtgatca gcctcgactg tgccttctag  5700
ttgccagcca tctgttgttt gcccctcccc cgtgccttcc ttgaccctgg aaggtgccac  5760
tcccactgtc ctttcctaat aaaatgagga aattgcatcg cattgtctga gtaggtgtca  5820
ttctattctg gggggtgggg tggggcagga cagcaagggg gaggattggg aagacaatag  5880
caggcatgct ggggatgcgg tgggctctat ggaaccagct ggggcccg              5928
```

```
SEQ ID NO: 28          moltype = DNA  length = 5934
FEATURE                Location/Qualifiers
source                 1..5934
                       mol_type = other DNA
                       organism = synthetic construct
SEQUENCE: 28
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg ggggagctgc ctgtggatgc taggttcccc cctagagtgc  1260
ccaagtcctt ccccttcaac acttctgtgg tgtacaagaa gaccctgttt gtggagttca  1320
ctgaccacct gtttaacatt gccaagccca ggccccccttg gatgggcctg ctggggccca  1380
ccatccaggc tgaggtgtat gacactgtgg tggtgaccct gaagaacatg gccagccatc  1440
ctgtgagcct gcatgctgtg ggggtgagct actggaagag cagcgagggg gctgagtatg  1500
atgaccagac tagccagagg gagaaggagg atgacaaggt gtttcctgga aagagccaca  1560
cctatgtgtg gcaggtgctg aaggagaatg gccccacagc ctctgacccc ccttgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
```

```
atggctatgt gaataggagc ctgcctggcc tgattggctg ccacaggaag tctgtgtact  1920
ggcatgtgat tggaatgggc acaacccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gttttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga attctagaca ccctagcacc agacagaaac  3420
agtttaatgc cactaatgtg tctaacaaca gcaacaccag caatgacagc aatgtgtcta  3480
acaagacatc taacaacagc aacgccacaa acaagaccaa caacacaaat gatagcacaa  3540
accggaccaa ccagaccaat accagccagc agaacttcgt gacccagaga agtaagagag  3600
agatcaccag gactaccctg cagtctgatc aggaggagat tgactatgat gacacaatct  3660
ctgtggagat gaagaaggag gattttgaca tctatgatga ggatgagaac cagagcccca  3720
gatcttttca gaagaagacc agacactact tcattgctgc tgtggagagg ctgtgggact  3780
atggcatgag cagcagccct catgtgctga ggaacagggc ccagtctggc tctgtgcccc  3840
agttcaagaa ggtggtgttc caggagttta ctgatggcag cttcacccag cccctgtaca  3900
gaggggagct gaatgagcac ctgggcctgc tgggccctta tatcagggct gaggtggagg  3960
ataacattat ggtgactttc aggaaccagg cctctaggcc ctacagcttc tatagcagcc  4020
tgatctctta tgaggaggat cagaggcagg gggctgagcc cagaaagaac tttgtgaagc  4080
ctaatgagac taagacctac ttctggaagg tccagcacca catggccccc accaaggatg  4140
agtttgattg caaggcctgg gcctatttct ctgatgtgga cctggagaag gatgtccatt  4200
ctggcctgat tggccctctg ctggtgtgcc acactaacac tctgaatcct gcccatggca  4260
ggcaggtgac tgtccaggag tttgccctgt tcttcactat ctttgatgag accaagagct  4320
ggtactttac tgagaacatg gagagaaact gcagggctcc ttgcaatatc cagatggagg  4380
accccacctt caaggagaac tacaggtttc atgccatcaa tggtacatc atggacaccc  4440
tgcctggcct ggtgatggct caggaccaga gaatcagatg gtatctgctg agcatgggca  4500
gcaatgagaa tatccacagc atccacttct ctggacatgt gttcactgtg aggaagaagg  4560
aggagtacaa gatggctctg tataatctgt accctggagt gtttgaaact gtggagatgc  4620
tgccttctaa ggctggcatc tggagggtgg agtgcctgat tggggagcac ctgcatgctg  4680
gcatgagcac cctgttcctg gtgtacagca acaagtgtca gaccccccctg ggcatggcct  4740
ctggacacat cagggacttc cagatcacag cctctggcca gtatggccag tgggccccca  4800
agctggccag gctgcattat tctggcagca tcaatgcctg gtctaccaag gagcccttta  4860
gctggatcaa ggtggacctg ctggccccca tgattatcca tggcatcaag acccaggggg  4920
ccaggcagaa gttctctagc ctgtacatca gccagttcat catcatgtac tctctggatg  4980
gcaagaagtg gcagacctac aggggcaaca gcactggcac actgatggtg ttctttggca  5040
atgtggacag ctctggcatc aagcacaaca tcttcaatcc ccccattatc gctaggtata  5100
ttaggctgca tcccacccac tacagcatca gatctaccct gagaatggag ctgatgggct  5160
gtgacctgaa ctcttgcagc atgcccctgg gcatggagtc taaggccatc tctgatgccc  5220
agattactgc cagcagctac ttcaccaata tgtttgccac ctggagccct tctaaggcca  5280
ggctgcatct gcaggggagg agcaatgcct ggaggcctca ggtgaacaac cctaaggagt  5340
ggctgcaggt ggatttccag aagaccatga aggtgactgg agtgaccacc cagggagtca  5400
agagcctgct gaccagcatg tatgtgaagg agtttctgat cagctctagc caggatggcc  5460
accagtggac tctgttcttt cagaatggga aggtgaaggt gtttcagggc aatcaggact  5520
ctttcacccc tgtggtgaac agcctggacc ccccccctgct gaccagatac ctgagaatcc  5580
acccccagag ctgggtgcac cagatcgccc tgaggatgga ggtgctgggc tgtgaggctc  5640
aggatctgta ctgagatatc tctagagtcg acagtactgg tgatcagcct cgactgtgcc  5700
ttctagttgc cagccatctg ttgtttgccc ctcccccgtg ccttccttga ccctggaagg  5760
tgccactccc actgtccttt cctaataaaa tgaggaaatt gcatcgcatt gtctgagtag  5820
gtgtcattct attctggggg gtggggtggg gcaggacagc aagggggagg attgggaaga  5880
caatagcagg catgctgggg atgcggtggg ctctatggaa ccagctgggg cccg        5934
```

```
SEQ ID NO: 29          moltype = DNA  length = 204
FEATURE                Location/Qualifiers
source                 1..204
                       mol_type = other DNA
                       organism = synthetic construct
SEQUENCE: 29
gtgatgcggt tttggcagta caccaatggg cgtggatagc ggtttgactc acggggattt  60
ccaagtctcc accccattga cgtcaatggg agtttgtttt ggcaccaaaa tcaacgggac  120
tttccaaaat gtcgtaataa ccccgccccg ttgacgcaaa tgggcggtag gcgtgtacgg  180
tgggaggtct atataagcag aggt                                        204
```

-continued

```
SEQ ID NO: 30          moltype = DNA  length = 380
FEATURE                Location/Qualifiers
source                 1..380
                       mol_type = other DNA
                       organism = synthetic construct
SEQUENCE: 30
ggcattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt ccgcccccta ttgacgtcaa tgacggtaaa tggcccgcct  300
ggcattatgc ccagtacatg accttacggg actttcctac ttggcagtac atctacgtat  360
tagtcatcgc tattaccatg                                              380

SEQ ID NO: 31          moltype = DNA  length = 88
FEATURE                Location/Qualifiers
source                 1..88
                       mol_type = other DNA
                       organism = synthetic construct
SEQUENCE: 31
ggtaccgaag ccgctagcgc taccggtcaa gcttggatcc gctagctccg gagagctcag  60
atctgatatc tctagagtcg acagtact                                     88

SEQ ID NO: 32          moltype = DNA  length = 225
FEATURE                Location/Qualifiers
source                 1..225
                       mol_type = other DNA
                       organism = synthetic construct
SEQUENCE: 32
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
tgagtaggtg tcattctatt ctggggggtg gggtggggca ggacagcaag ggggaggatt  180
gggaagacaa tagcaggcat gctggggatg cggtgggctc tatgg                  225

SEQ ID NO: 33          moltype = DNA  length = 57
FEATURE                Location/Qualifiers
source                 1..57
                       mol_type = other DNA
                       organism = synthetic construct
SEQUENCE: 33
atgcagattg aactgagcac ctgcttcttc ctgtgtctgc tgagattctg cttctct     57

SEQ ID NO: 34          moltype = DNA  length = 57
FEATURE                Location/Qualifiers
source                 1..57
                       mol_type = other DNA
                       organism = synthetic construct
SEQUENCE: 34
atgcaaatag agctctccac ctgcttcttt ctgtgccttt tgcgattctg ctttagt     57

SEQ ID NO: 35          moltype = DNA  length = 4317
FEATURE                Location/Qualifiers
source                 1..4317
                       mol_type = other DNA
                       organism = synthetic construct
SEQUENCE: 35
gccaccagaa gatactacct gggtgcagtg gaactgtcat gggactatat gcaaagtgat  60
ctcggtgagc tgcctgtgga cgcaagattt cctcctagag tgccaaaatc ttttccattc  120
aacacctcag tcgtgtacaa aaagactctg tttgtagaat tcacggatca ccttttcaac  180
atcgctaagc caaggccacc ctggatgggt ctgctaggtc ctaccatcca ggctgaggtt  240
tatgatacag tggtcattac acttaagaac atggcttccc atcctgtcag tcttcatgct  300
gttggtgtat cctactggaa agcttctgag ggagctgaat atgatgatca gaccagtcaa  360
agggagaaag aagatgataa agtcttccct ggtggaagcc atacatatgt ctggcaggtc  420
ctgaaagaga atggtccaat ggcctctgac ccactgtgcc ttacctactc atatctttct  480
catgtggacc tggtaaaaga cttgaattca ggcctcattg gagccctact agtatgtaga  540
gaagggagtc tggccaagga aaagacacag accttgcaca aatttatact actttttgct  600
gtatttgatg aagggaaaag ttggcactca gaaacaaaga actccttgat gcaggatagg  660
gatgctgcat ctgctcgggc ctggcctaaa atgcacacag tcaatggtta tgtaaacagg  720
tctctgccag gtctgattgg atgccacagg aaatcagtct attggcatgt gattggaatg  780
ggcaccactc ctgaagtgca ctcaatattc ctcgaaggtc acacatttct tgtgaggaac  840
catcgccagg cgtccttgga aatctcgcca ataactttcc ttactgctca aacactcttg  900
atggaccttg gacagtttct actgttttgt catatctctt cccaccaaca tgatggcatg  960
gaagcttatg tcaaagtaga cagctgtcca gaggaacccc aactacgaat gaaaaataat  1020
gaagaagcgg aagactatga tgatgatctt actgattctg aaatggatgt ggtcaggttt  1080
gatgatgaca actctccttc ctttatccaa attcgctcag ttgccaagaa gcatcctaaa  1140
acttgggtac attacattgc tgctgaagag gaggactggg actatgctcc cttagtcctc  1200
gcccccgatg acagaagtta taaaagtcaa tatttgaaca atggccctca gcggattggt  1260
aggaagtaca aaaaagtccg atttatggca tacacagatg aaacctttaa gactcgtgaa  1320
```

gctattcagc atgaatcagg aatcttggga cctttacttt atggggaagt tggagacaca 1380
ctgttgatta tatttaagaa tcaagcaagc agaccatata acatctaccc tcacggaatc 1440
actgatgtcc gtcctttgta ttcaaggaga ttaccaaaag gtgtaaaaca tttgaaggat 1500
tttccaattc tgccaggaga aatattcaaa tataaatgga cagtgactgt agaagatggg 1560
ccaactaaat cagatcctcg gtgcctgacc cgctattact ctagtttcgt taatatggag 1620
agagatctag cttcaggact cattggccct ctcctcatct gctacaaaga atctgtagat 1680
caaagaggaa accagataat gtcagacaag aggaatgtca tcctgttttc tgtatttgat 1740
gagaaccgaa gctggtacct cacagagaat atacaacgct ttctccccaa tccagctgga 1800
gtgcagcttg aggatccaga gttccaagcc tccaacatca tgcacagcat caatggctat 1860
gtttttgata gtttgcagtt gtcagtttgt ttgcatgagg tggcatactg gtacattcta 1920
agcattggag cacagactga cttcctttct gtcttcttct ctggatatac cttcaaacac 1980
aaaatggtct atgaagacac actcacccta ttcccattct caggagaaac tgtcttcatg 2040
tcgatggaaa acccaggtct atggattctg gggtgccaca actcagactt tcggaacaga 2100
ggcatgaccg ccttactgaa ggtttctagt tgtgacaaga acactggtga ttattacgag 2160
gacagttatg aagatatttc agcatacttg ctgagtaaaa acaatgccat tgaaccaaga 2220
agcttctctc aaaacccacc agtcttgaaa cgccatcaac gggaaataac tcgtactact 2280
cttcagtcag atcaagagga aattgactat gatgatacca tatcagttga aatgaagaag 2340
gaagattttg acatttatga tgaggatgaa aatcagagcc cccgcagctt tcaaaagaaa 2400
acacgacact attttattgc tgcagtggag aggctctggg attatgggat gagtagctcc 2460
ccacatgttc taagaaacag ggctcagagt ggcagtgtcc ctcagttcaa gaaagttgtt 2520
ttccaggaat ttactgatgg ctcctttact cagcccttat accgtggaga actaaatgaa 2580
catttgggac tcctggggcc atatataaga gcagaagttg aagataatat catggtaact 2640
ttcagaaatc aggcctctcg tccctattcc ttctattcta gccttatttc ttatgaggaa 2700
gatcagaggc aaggagcaga acctagaaaa aactttgtca agcctaatga aaccaaaact 2760
tacttttgga aagtgcaaca tcatatggca cccactaaag atgagtttga ctgcaaagcc 2820
tgggcttatt tctctgatgt tgacctggaa aaagatgtgc actcaggcct gattggaccc 2880
cttctggtct gccacactaa cacactgaac cctgctcatg ggagacaagt gacagtacag 2940
gaatttgctc tgtttttcac catctttgat gagaccaaaa gctggtactt cactgaaaat 3000
atggaaagaa actgcagggc tccctgcaat atccagatgg aagatcccac ttttaaagag 3060
aattatcgct tccatgcaat caatggctac ataatggata cactacctgg cttagtaatg 3120
gctcaggatc aaaggattcg atggtatctg ctcagcatgg gcagcaatga aaacatccat 3180
tctattcatt tcagtggaca tgtgttcact gtacgaaaaa aagaggagta taaaatggca 3240
ctgtacaatc tctatccagg tgtttttgag acagtggaaa tgttaccatc caaagctgga 3300
atttggcggg tggaatgcct tattggcgag catctacatg ctgggatgag cacacttttt 3360
ctggtgtaca gcaataagtg tcagactccc ctgggaatgg cttctggaca cattagagat 3420
tttcagatta cagcttcagg acaatatgga cagtgggccc caaagctggc cagacttcat 3480
tattccggat caatcaatgc ctggagcacc aaggagccct tttcttggat caaggtggat 3540
ctgttggcac caatgattat tcacggcatc aagacccagg gtgcccgtca gaagttctcc 3600
agcctctaca tctctcagtt tatcatcatg tatagtcttg atgggaagaa gtggcagact 3660
tatcgaggaa attccactgg aaccttaatg gtcttctttg gcaatgtgga ttcatctggg 3720
ataaaacaca atatttttaa ccctccaatt attgctcgat acatccgttt gcacccaact 3780
cattatagca ttcgcagcac tcttcgcatg gagttgatgg gctgtgattt aaatagttgc 3840
agcatgccat tgggaatgga gagtaaagca atatcagatg cacagattac tgcttcatcc 3900
tactttacca atatgtttgc cacctggtct ccttcaaaag ctcgacttca cctccaaggg 3960
aggagtaatg cctggagacc tcaggtgaat aatccaaaag agtggctgca agtggacttc 4020
cagaagacaa tgaaagtcac aggagtaact actcagggag taaaatctct gcttaccagc 4080
atgtatgtga aggagttcct catctccagc agtcaagatg gccatcagtg gactctcttt 4140
tttcagaatg gcaaagtaaa ggtttttcag ggaaatcaag actccttcac acctgtggtg 4200
aactctctag acccaccgtt actgactcgc taccttcgaa ttcaccccca gagttgggtg 4260
caccagattg ccctgaggat ggaggttctg ggctgcgagg cacaggacct ctactga 4317

SEQ ID NO: 36 moltype = DNA length = 4368
FEATURE Location/Qualifiers
source 1..4368
mol_type = other DNA
organism = synthetic construct
SEQUENCE: 36
gccaccagaa gatactacct gggtgcagtg gaactgtcat gggactatat gcaaagtgat 60
ctcggtgagc tgcctgtgga cgcaagattt cctcctagag tgccaaaatc ttttccattc 120
aacacctcag tcgtgtacaa aaagactctg tttgtagaat tcacggatca ccttttcaac 180
atcgctaagc caaggccacc ctggatgggt ctgctaggtc ctaccatcca ggctgaggtt 240
tatgatacag tggtcattac acttaagaac atggcttccc atcctgtcag tcttcatgct 300
gttggtgtat cctactggaa agcttctgag ggagctgaat atgatgatca gaccagtcaa 360
agggagaaag aagatgataa agtcttccct ggtggaagcc atacatatgt ctggcaggtc 420
ctgaaagaga atggtccaat ggcctctgac ccactgtgcc ttacctactc atatctttct 480
catgtggacc tggtaaaaga cttgaattca ggcctcattg gagccctact agtatgtaga 540
gaagggagtc tggccaagga aaagacacag accttgcaca aatttatact actttttgct 600
gtatttgatg aagggaaaag ttggcactca gaaacaaaga actccttgat gcaggatagg 660
gatgctgcat ctgctcgggc ctggcctaaa atgcacacag tcaatggtta tgtaaacagg 720
tctctgccag gtctgattgg atgccacagg aaatcagtct attggcatgt gattggaatg 780
ggcaccactc ctgaagtgca ctcaatattc ctcgaaggtc acacatttct tgtgaggaac 840
catcgccagg cgtccttgga aatctcgcca ataactttcc ttactgctca aacactcttg 900
atggaccttg gacagtttct actgttttgt catatctctt cccaccaaca tgatggcatg 960
gaagcttatg tcaaagtaga cagctgtcca gaggaacccc aactacgaat gaaaaataat 1020
gaagaagcgg aagactatga tgatgatctt actgattctg aaatggatgt ggtcaggttt 1080
gatgatgaca actctccttc ctttatccaa attcgctcag ttgccaagaa gcatcctaaa 1140
acttgggtac attacattgc tgctgaagag gaggactggg actatgctcc cttagtcctc 1200
gcccccgatg acagaagtta taaaagtcaa tatttgaaca atggccctca gcggattggt 1260
aggaagtaca aaaaagtccg atttatggca tacacagatg aaacctttaa gactcgtgaa 1320

```
gctattcagc atgaatcagg aatcttggga cctttacttt atggggaagt tggagacaca  1380
ctgttgatta tatttaagaa tcaagcaagc agaccatata acatctaccc tcacggaatc  1440
actgatgtcc gtcctttgta ttcaaggaga ttaccaaaag gtgtaaaaca tttgaaggat  1500
tttccaattc tgccaggaga aatattcaaa tataaatgga cagtgactgt agaagatggg  1560
ccaactaaat cagatcctcg gtgcctgacc cgctattact ctagtttcgt taatatggag  1620
agagatctag cttcaggact cattggccct ctcctcatct gctacaaaga atctgtagat  1680
caaagaggaa accagataat gtcagacaag aggaatgtca tcctgttttc tgtatttgat  1740
gagaaccgaa gctggtacct cacagagaat atacaacgct ttctccccaa tccagctgga  1800
gtgcagcttg aggatccaga gttccaagcc tccaacatca tgcacagcat caatggctat  1860
gtttttgata gtttgcagtt gtcagtttgt ttgcatgagg tggcatactg gtacattcta  1920
agcattggag cacagactga cttcctttct gtcttcttct ctggatatac cttcaaacac  1980
aaaatggtct atgaagacac actcacccta ttcccattct caggagaaac tgtcttcatg  2040
tcgatggaaa acccaggtct atggattctg gggtgccaca actcagactt tcggaacaga  2100
ggcatgaccg ccttactgaa ggtttctagt tgtgacaaga acactggtga ttattacgag  2160
gacagttatg aagatatttc agcatacttg ctgagtaaaa acaatgccat tgaaccaaga  2220
agcttcagcc agaatgccac taatgtgtct aacaacagca acaccagcaa tgacagcaat  2280
gtgtctcccc ctgtgctgaa gagacatcag agggaaataa ctcgtactac tcttcagtca  2340
gatcaagagg aaattgacta tgatgatacc atatcagttg aaatgaagaa ggaagatttt  2400
gacatttatg atgaggatga aaatcagagc cccgcagct ttcaaaagaa aacacgacac  2460
tattttattg ctgcagtgga gaggctctgg gattatggga tgagtagctc ccacatgtt  2520
ctaagaaaca gggctcagag tggcagtgtc cctcagttca agaaagttgt tttccaggaa  2580
tttactgatg gctcctttac tcagccctta taccgtggag aactaaatga acatttggga  2640
ctcctggggc catatataag agcagaagtt gaagataata tcatggtaac tttcagaaat  2700
caggcctctc gtccctattc cttctattct agccttattt cttatgagga agatcagagg  2760
caaggagcag aacctagaaa aaactttgtc aagcctaatg aaaccaaaac ttacttttgg  2820
aaagtgcaac atcatatggc acccactaaa gatgagtttg actgcaaagc ctgggcttat  2880
ttctctgatg ttgacctgga aaaagatgtg cactcaggcc tgattggacc ccttctggtc  2940
tgccacacta acacactgaa ccctgctcat gggagacaag tgacagtaca ggaatttgct  3000
ctgtttttca ccatctttga tgagaccaaa agctggtact tcactgaaaa tatggaaaga  3060
aactgcaggg ctccctgcaa tatccagatg gaagatccca cttttaaaga gaattatcgc  3120
ttccatgcaa tcaatggcta cataatggat acactacctg gcttagtaat ggctcaggat  3180
caaaggattc gatggtatct gctcagcatg ggcagcaatg aaaacatcca ttctattcat  3240
ttcagtggac atgtgttcac tgtacgaaaa aaagaggagt ataaaatggc actgtacaat  3300
ctctatccag gtgtttttga gacagtggaa atgttaccat ccaaagctgg aatttggcgg  3360
gtggaatgcc ttattggcga gcatctacat gctgggatga gcacactttt tctggtgtac  3420
agcaataagt gtcagactcc cctgggaatg gcttctggac acattagaga ttttcagatt  3480
acagcttcag gacaatatgg acagtgggcc ccaaagctgg ccagacttca ttattccgga  3540
tcaatcaatg cctggagcac caaggagccc ttttcttgga tcaaggtgga tctgttggca  3600
ccaatgatta ttcacggcat caagacccag ggtgcccgtc agaagttctc cagcctctac  3660
atctctcagt ttatcatcat gtatagtctt gatgggaaga agtggcagac ttatcgagga  3720
aattccactg gaaccttaat ggtcttcttt ggcaatgtgg attcatctgg gataaaacac  3780
aatattttta accctccaat tattgctcga tacatccgtt tgcacccaac tcattatagc  3840
attcgcagca ctcttcgcat ggagttgatg ggctgtgatt taaatagttg cagcatgcca  3900
ttgggaatgg agagtaaagc aatatcagat gcacagatta ctgcttcatc ctactttacc  3960
aatatgtttg ccacctggtc tccttcaaaa gctcgacttc acctccaagg gaggagtaat  4020
gcctggagac ctcaggtgaa taatccaaaa gagtggctgc aagtggactt ccagaagaca  4080
atgaaagtca caggagtaac tactcaggga gtaaaatctc tgcttaccag catgtatgtg  4140
aaggagttcc tcatctccag cagtcaagat ggccatcagt ggactctctt ttttcagaat  4200
ggcaaagtaa aggtttttca gggaaatcaa gactccttca cacctgtggt gaactctcta  4260
gacccaccgt tactgactcg ctaccttcga attcaccccc agagttgggt gcaccagatt  4320
gccctgagga tggaggttct gggctgcgag gcacaggacc tctactga              4368
```

```
SEQ ID NO: 37          moltype = DNA  length = 4338
FEATURE                Location/Qualifiers
source                 1..4338
                       mol_type = other DNA
                       organism = synthetic construct
SEQUENCE: 37
gccaccagaa gatactacct gggtgcagtg gaactgtcat gggactatat gcaaagtgat  60
ctcggtgagc tgcctgtgga cgcaagattt cctcctagag tgccaaaatc ttttccattc  120
aacacctcag tcgtgtacaa aaagactctg tttgtagaat tcacggatca ccttttcaac  180
atcgctaagc caaggccacc ctggatgggt ctgctaggtc ctaccatcca ggctgaggtt  240
tatgatacag tggtcattac acttaagaac atggcttccc atcctgtcag tcttcatgct  300
gttggtgtat cctactggaa agcttctgag ggagctgaat atgatgatca gaccagtcaa  360
agggagaaag aagatgataa agtcttccct ggtggaagcc atacatatgt ctggcaggtc  420
ctgaaagaga atggtccaat ggcctctgac ccactgtgcc ttacctactc atatctttct  480
catgtggacc tggtaaaaga cttgaattca ggcctcattg gagccctact agtatgtaga  540
gaagggagtc tggccaagga aaagacacag accttgcaca aatttatact actttttgct  600
gtatttgatg aagggaaaag ttggcactca gaaacaaaga actccttgat gcaggatagg  660
gatgctgcat ctgctcgggc ctggcctaaa atgcacacag tcaatggtta tgtaaacagg  720
tctctgccag gtctgattgg atgccacagg aaatcagtct attggcatgt gattggaatg  780
ggcaccactc ctgaagtgca ctcaatattc ctcgaaggtc acacatttct tgtgaggaac  840
catcgccagg cgtccttgga aatctcgcca ataactttcc ttactgctca aacactcttg  900
atggaccttg gacagtttct actgttttgt catatctctt cccaccaaca tgatggcatg  960
gaagcttatg tcaaagtaga cagctgtcca gaggaacccc aactacgaat gaaaaataat  1020
gaagaagcgg aagactatga tgatgatctt actgattctg aaatggatgt ggtcaggttt  1080
gatgatgaca actctccttc ctttatccaa attcgctcag ttgccaagaa gcatcctaaa  1140
acttgggtac attacattgc tgctgaagag gaggactggg actatgctcc ccttagtcctc 1200
gcccccgatg acagaagtta taaaagtcaa tatttgaaca atggccctca gcggattggt  1260
```

```
aggaagtaca aaaaagtccg atttatggca tacacagatg aaacctttaa gactcgtgaa  1320
gctattcagc atgaatcagg aatcttggga cctttacttt atggggaagt tggagacaca  1380
ctgttgatta tatttaagaa tcaagcaagc agaccatata acatctaccc tcacggaatc  1440
actgatgtcc gtcctttgta ttcaaggaga ttaccaaaag gtgtaaaaca tttgaaggat  1500
tttccaattc tgccaggaga aatattcaaa tataaatgga cagtgactgt agaagatggg  1560
ccaactaaat cagatcctcg gtgcctgacc cgctattact ctagtttcgt taatatggag  1620
agagatctag cttcaggact cattggccct ctcctcatct gctacaaaga atctgtagat  1680
caaagaggaa accagataat gtcagacaag aggaatgtca tcctgttttc tgtatttgat  1740
gagaaccgaa gctggtacct cacagagaat atacaacgct ttctccccaa tccagctgga  1800
gtgcagcttg aggatccaga gttccaagcc tccaacatca tgcacagcat caatggctat  1860
gtttttgata gtttgcagtt gtcagtttgt ttgcatgagg tggcatactg gtacattcta  1920
agcattggag cacagactga cttcctttct gtcttcttct ctggatatac cttcaaacac  1980
aaaatggtct atgaagacac actcacccta ttcccattct caggagaaac tgtcttcatg  2040
tcgatggaaa acccaggtct atggattctg gggtgccaca actcagactt tcggaacaga  2100
ggcatgaccg ccttactgaa ggtttctagt tgtgacaaga acactggtga ttattacgag  2160
gacagttatg aagatatttc agcatacttg ctgagtaaaa acaatgccat tgaaccaaga  2220
agcttcagcc agaattctag acaccctagc caaaaccccc ctgtgctgaa gagacatcag  2280
agggaaataa ctcgtactac tcttcagtca gatcaagagg aaattgacta tgatgatacc  2340
atatcagttg aaatgaagaa ggaagatttt gacatttatg atgaggatga aaatcagagc  2400
ccccgcagct ttcaaaagaa aacacgacac tattttattg ctgcagtgga gaggctctgg  2460
gattatggga tgagtagctc cccacatgtt ctaagaaaca gggctcagag tggcagtgtc  2520
cctcagttca agaaagttgt tttccaggaa tttactgatg gctcctttac tcagccctta  2580
taccgtggag aactaaatga acatttggga ctcctggggc catatataag agcagaagtt  2640
gaagataata tcatggtaac tttcagaaat caggcctctc gtccctattc cttctattct  2700
agccttattt cttatgagga agatcagagg caaggagcag aacctagaaa aaactttgtc  2760
aagcctaatg aaaccaaaac ttacttttgg aaagtgcaac atcatatggc acccactaaa  2820
gatgagtttg actgcaaagc ctgggcttat ttctctgatg ttgacctgga aaaagatgtg  2880
cactcaggcc tgattggacc ccttctggtc tgccacacta acacactgaa ccctgctcat  2940
gggagacaag tgacagtaca ggaatttgct ctgtttttca ccatctttga tgagaccaaa  3000
agctggtact tcactgaaaa tatggaaaga aactgcaggg ctccctgcaa tatccagatg  3060
gaagatccca cttttaaaga gaattatcgc ttccatgcaa tcaatggcta cataatggat  3120
acactacctg gcttagtaat ggctcaggat caaaggattc gatggtatct gctcagcatg  3180
ggcagcaatg aaaacatcca ttctattcat ttcagtggac atgtgttcac tgtacgaaaa  3240
aaagaggagt ataaaatggc actgtacaat ctctatccag gtgtttttga gacagtggaa  3300
atgttaccat ccaaagctgg aatttggcgg gtggaatgcc ttattggcga gcatctacat  3360
gctgggatga gcacactttt tctggtgtac agcaataagt gtcagactcc cctgggaatg  3420
gcttctggac acattagaga ttttcagatt acagcttcag gacaatatgg acagtgggcc  3480
ccaaagctgg ccagacttca ttattccgga tcaatcaatg cctggagcac caaggagccc  3540
ttttcttgga tcaaggtgga tctgttggca ccaatgatta ttcacggcat caagacccag  3600
ggtgcccgtc agaagttctc cagcctctac atctctcagt ttatcatcat gtatagtctt  3660
gatgggaaga agtggcagac ttatcgagga aattccactg gaaccttaat ggtcttcttt  3720
ggcaatgtgg attcatctgg gataaaacac aatattttta accctccaat tattgctcga  3780
tacatccgtt tgcacccaac tcattatagc attcgcagca ctcttcgcat ggagttgatg  3840
ggctgtgatt taaatagttg cagcatgcca ttgggaatgg agagtaaagc aatatcagat  3900
gcacagatta ctgcttcatc ctactttacc aatatgtttg ccacctggtc tccttcaaaa  3960
gctcgacttc acctccaagg gaggagtaat gcctggagac ctcaggtgaa taatccaaaa  4020
gagtggctgc aagtggactt ccagaagaca atgaaagtca caggagtaac tactcaggga  4080
gtaaaatctc tgcttaccag catgtatgtg aaggagttcc tcatctccag cagtcaagat  4140
ggccatcagt ggactctctt ttttcagaat ggcaaagtaa aggtttttca gggaaatcaa  4200
gactccttca cacctgtggt gaactctcta gacccaccgt tactgactcg ctaccttcga  4260
attcaccccc agagttgggt gcaccagatt gccctgagga tggaggttct gggctgcgag  4320
gcacaggacc tctactga                                             4338

SEQ ID NO: 38          moltype = DNA  length = 4491
FEATURE                Location/Qualifiers
source                 1..4491
                       mol_type = other DNA
                       organism = synthetic construct
SEQUENCE: 38
gccaccagaa gatactacct gggtgcagtg gaactgtcat gggactatat gcaaagtgat  60
ctcggtgagc tgcctgtgga cgcaagattt cctcctagag tgccaaaatc ttttccattc  120
aacacctcag tcgtgtacaa aaagactctg tttgtagaat tcacggatca cctttttcaac  180
atcgctaagc caaggccacc ctggatgggt ctgctaggtc ctaccatcca ggctgaggtt  240
tatgatacag tggtcattac acttaagaac atggcttccc atcctgtcag tcttcatgct  300
gttggtgtat cctactggaa agcttctgag ggagctgaat atgatgatca gaccagtcaa  360
agggagaaag aagatgataa agtcttccct ggtggaagcc atacatatgt ctggcaggtc  420
ctgaaagaga atggtccaat ggcctctgac ccactgtgcc ttacctactc atatctttct  480
catgtggacc tggtaaaaga cttgaattca ggcctcattg gagccctact agtatgtaga  540
gaagggagtc tggccaagga aaagacacag accttgcaca aatttatact actttttgct  600
gtatttgatg aagggaaaag ttggcactca gaaacaaaga actccttgat gcaggatagg  660
gatgctgcat ctgctcgggc ctggcctaaa atgcacacag tcaatggtta tgtaaacagg  720
tctctgccag gtctgattgg atgccacagg aaatcagtct attggcatgt gattggaatg  780
ggcaccactc ctgaagtgca ctcaatattc ctcgaaggtc acacatttct tgtgaggaac  840
catcgccagg cgtccttgga aatctcgcca ataactttcc ttactgctca aacactcttg  900
atggaccttg gacagtttct actgttttgt catatctctt cccaccaaca tgatggcatg  960
gaagcttatg tcaaagtaga cagctgtcca gaggaacccc aactacgaat gaaaaataat  1020
gaagaagcgg aagactatga tgatgatctt actgattctg aaatggatgt ggtcaggttt  1080
gatgatgaca actctccttc ctttatccaa attcgctcag ttgccaagaa gcatcctaaa  1140
acttgggtac attacattgc tgctgaagag gaggactggg actatgctcc cttagtcctc  1200
```

```
gcccccgatg acagaagtta taaaagtcaa tatttgaaca atggccctca gcggattggt  1260
aggaagtaca aaaaagtccg atttatggca tacacagatg aaacctttaa gactcgtgaa  1320
gctattcagc atgaatcagg aatcttggga cctttacttt atggggaagt tggagacaca  1380
ctgttgatta tatttaagaa tcaagcaagc agaccatata acatctaccc tcacggaatc  1440
actgatgtcc gtcctttgta ttcaaggaga ttaccaaaag gtgtaaaaca tttgaaggat  1500
tttccaattc tgccaggaga aatattcaaa tataaatgga cagtgactgt agaagatggg  1560
ccaactaaat cagatcctcg gtgcctgacc cgctattact ctagtttcgt taatatggag  1620
agagatctag cttcaggact cattggccct ctcctcatct gctacaaaga atctgtagat  1680
caaagaggaa accagataat gtcagacaag aggaatgtca tcctgttttc tgtatttgat  1740
gagaaccgaa gctggtacct cacagagaat atacaacgct ttctccccaa tccagctgga  1800
gtgcagcttg aggatccaga gttccaagcc tccaacatca tgcacagcat caatggctat  1860
gtttttgata gtttgcagtt gtcagtttgt ttgcatgagg tggcatactg gtacattcta  1920
agcattggag cacagactga cttcctttct gtcttcttct ctggatatac cttcaaacac  1980
aaaatggtct atgaagacac actcacccta ttcccattct caggagaaac tgtcttcatg  2040
tcgatggaaa acccaggtct atggattctg gggtgccaca actcagactt tcggaacaga  2100
ggcatgaccg ccttactgaa ggtttctagt tgtgacaaga acactggtga ttattacgag  2160
gacagttatg aagatatttc agcatacttg ctgagtaaaa acaatgccat tgaaccaaga  2220
agcttcagcc agaatagcag acaccctagc accagacaga aacagtttaa tgccactaat  2280
gtgagcaaca acagcaacac cagcaatgac agcaatgtgt ctaacaagac atctaacaac  2340
agcaatgcca caaacaagac caacaacaca aatgatagca caaacaggac caaccagacc  2400
aataccagcc cccctgtgct gaagagacat cagagggaaa taactcgtac tactcttcag  2460
tcagatcaag aggaaattga ctatgatgat accatatcag ttgaaatgaa gaaggaagat  2520
tttgacattt atgatgagga tgaaaatcag agcccccgca gctttcaaaa gaaaacacga  2580
cactatttta ttgctgcagt ggagaggctc tgggattatg ggatgagtag ctccccacat  2640
gttctaagaa acagggctca gagtggcagt gtccctcagt tcaagaaagt tgttttccag  2700
gaatttactg atggctcctt tactcagccc ttataccgtg gagaactaaa tgaacatttg  2760
ggactcctgg ggccatatat aagagcagaa gttgaagata atatcatggt aactttcaga  2820
aatcaggcct ctcgtcccta ttccttctat tctagcctta tttcttatga ggaagatcag  2880
aggcaaggag cagaacctag aaaaaacttt gtcaagccta atgaaaccaa aacttacttt  2940
tggaaagtgc aacatcatat ggcacccact aaagatgagt ttgactgcaa agcctgggct  3000
tatttctctg atgttgacct ggaaaaagat gtgcactcag gcctgattgg acccctcctg  3060
gtctgccaca ctaacacact gaaccctgct catgggagac aagtgacagt acaggaattt  3120
gctctgtttt tcaccatctt tgatgagacc aaaagctggt acttcactga aaatatggaa  3180
agaaactgca gggctccctg caatatccag atggaagatc ccacttttaa agagaattat  3240
cgcttccatg caatcaatgg ctacataatg gatacactac ctggcttagt aatggctcag  3300
gatcaaagga ttcgatggta tctgctcagc atgggcagca atgaaaacat ccattctatt  3360
catttcagtg gacatgtgtt cactgtacga aaaaaagagg agtataaaat ggcactgtac  3420
aatctctatc caggtgtttt tgagacagtg gaaatgttac catccaaagc tggaatttgg  3480
cgggtggaat gccttattgg cgagcatcta catgctggga tgagcacact tttctggtg  3540
tacagcaata agtgtcagac tcccctggga atggcttctg gacacattag agatttcag  3600
attacagctt caggacaata tggacagtgg gccccaaagc tggccagact tcattattcc  3660
ggatcaatca atgcctggag caccaaggag cccttttctt ggatcaaggt ggatctgttg  3720
gcaccaatga ttattcacgg catcaagacc cagggtgccc gtcagaagtt ctccagcctc  3780
tacatctctc agtttatcat catgtatagt cttgatggga agaagtggca gacttatcga  3840
ggaaattcca ctggaacctt aatggtcttc tttggcaatg tggattcatc tgggataaaa  3900
cacaatattt ttaaccctcc aattattgct cgatacatcc gtttgcaccc aactcattat  3960
agcattcgca gcactcttcg catggagttg atgggctgtg atttaaatag ttgcagcatg  4020
ccattgggaa tggagagtaa agcaatatca gatgcacaga ttactgcttc atcctacttt  4080
accaatatgt ttgccacctg gtctccttca aaagctcgac ttcacctcca agggaggagt  4140
aatgcctgga gacctcaggt gaataatcca aaagagtggc tgcaagtgga cttccagaag  4200
acaatgaaag tcacaggagt aactactcag ggagtaaaat ctctgcttac cagcatgtat  4260
gtgaaggagt tcctcatctc cagcagtcaa gatggccatc agtggactct ctttttcag  4320
aatggcaaag taaaggtttt tcagggaaat caagactcct tcacacctgt ggtgaactct  4380
ctagacccac cgttactgac tcgctacctt cgaattcacc cccagagttg ggtgcaccag  4440
attgccctga ggatggaggt tctgggctgc gaggcacagg acctctactg a           4491
```

```
SEQ ID NO: 39          moltype = DNA  length = 4497
FEATURE                Location/Qualifiers
source                 1..4497
                       mol_type = other DNA
                       organism = synthetic construct
SEQUENCE: 39
gccaccagaa gatactacct gggtgcagtg gaactgtcat gggactatat gcaaagtgat  60
ctcggtgagc tgcctgtgga cgcaagattt cctcctagag tgccaaaatc ttttccattc  120
aacacctcag tcgtgtacaa aaagactctg tttgtagaat tcacggatca ccttttcaac  180
atcgctaagc caaggccacc ctggatgggt ctgctaggtc ctaccatcca ggctgaggtt  240
tatgatacag tggtcattac acttaagaac atggcttccc atcctgtcag tcttcatgct  300
gttggtgtat cctactggaa agcttctgag ggagctgaat atgatgatca gaccagtcaa  360
agggagaaag aagatgataa agtcttccct ggtggaagcc atacatatgt ctggcaggtc  420
ctgaaagaga atggtccaat ggcctctgac ccactgtgcc ttacctactc atatctttct  480
catgtggacc tggtaaaaga cttgaattca ggcctcattg gagccctact agtatgtaga  540
gaagggagtc tggccaagga aaagacacag accttgcaca aatttatact acttttgct  600
gtatttgatg aagggaaaag ttggcactca gaaacaaaga actccttgat gcaggatagg  660
gatgctgcat ctgctcgggc ctggcctaaa atgcacacag tcaatggtta tgtaaacagg  720
tctctgccag gtctgattgg atgccacagg aaatcagtct attggcatgt gattggaatg  780
ggcaccactc ctgaagtgca ctcaatattc ctcgaaggtc acacatttct tgtgaggaac  840
catcgccagg cgtccttgga aatctcgcca ataactttcc ttactgctca aacactcttg  900
atggaccttg gacagtttct actgttttgt catatctctt cccaccaaca tgatggcatg  960
gaagcttatg tcaaagtaga cagctgtcca gaggaacccc aactacgaat gaaaaataat  1020
```

```
gaagaagcgg aagactatga tgatgatctt actgattctg aaatggatgt ggtcaggttt  1080
gatgatgaca actctccttc ctttatccaa attcgctcag ttgccaagaa gcatcctaaa  1140
acttgggtac attacattgc tgctgaagag gaggactggg actatgctcc cttagtcctc  1200
gcccccgatg acagaagtta taaaagtcaa tatttgaaca atggccctca gcggattggt  1260
aggaagtaca aaaaagtccg atttatggca tacacagatg aaacctttaa gactcgtgaa  1320
gctattcagc atgaatcagg aatcttggga cctttacttt atggggaagt tggagacaca  1380
ctgttgatta tatttaagaa tcaagcaagc agaccatata acatctaccc tcacggaatc  1440
actgatgtcc gtcctttgta ttcaaggaga ttaccaaaag gtgtaaaaca tttgaaggat  1500
tttccaattc tgccaggaga aatattcaaa tataaatgga cagtgactgt agaagatggg  1560
ccaactaaat cagatcctcg gtgcctgacc cgctattact ctagtttcgt taatatggag  1620
agagatctag cttcaggact cattggccct ctcctcatct gctacaaaga atctgtagat  1680
caaagaggaa accagataat gtcagacaag aggaatgtca tcctgttttc tgtatttgat  1740
gagaaccgaa gctggtacct cacagagaat atacaacgct ttctccccaa tccagctgga  1800
gtgcagcttg aggatccaga gttccaagcc tccaacatca tgcacagcat caatggctat  1860
gtttttgata gtttgcagtt gtcagtttgt ttgcatgagg tggcatactg gtacattcta  1920
agcattggag cacagactga cttcctttct gtcttcttct ctggatatac cttcaaacac  1980
aaaatggtct atgaagacac actcacccta ttcccattct caggagaaac tgtcttcatg  2040
tcgatggaaa acccaggtct atggattctg gggtgccaca actcagactt tcggaacaga  2100
ggcatgaccg ccttactgaa ggtttctagt tgtgacaaga acactggtga ttattacgag  2160
gacagttatg aagatatttc agcatacttg ctgagtaaaa acaatgccat tgaaccaaga  2220
agcttcagcc agaattctag acaccctagc accagacaga aacagtttaa tgccactaat  2280
gtgtctaaca acagcaacac cagcaatgac agcaatgtgt ctaacaagac atctaacaac  2340
agcaacgcca caaacaagac caacaacaca aatgatagca caaaccggac caaccagacc  2400
aataccagcc agcagaactt cgtgacccag agaagtaaga gagaaataac tcgtactact  2460
cttcagtcag atcaagagga aattgactat gatgatacca tatcagttga aatgaagaag  2520
gaagattttg acatttatga tgaggatgaa aatcagagcc cccgcagctt tcaaaagaaa  2580
acacgacact attttattgc tgcagtggag aggctctggg attatgggat gagtagctcc  2640
ccacatgttc taagaaacag ggctcagagt ggcagtgtcc ctcagttcaa gaaagttgtt  2700
ttccaggaat ttactgatgg ctcctttact cagcccttat accgtggaga actaaatgaa  2760
catttgggac tcctggggcc atatataaga gcagaagttg aagataatat catggtaact  2820
ttcagaaatc aggcctctcg tccctattcc ttctattcta gccttatttc ttatgaggaa  2880
gatcagaggc aaggagcaga acctagaaaa aactttgtca agcctaatga aaccaaaact  2940
tacttttgga aagtgcaaca tcatatggca cccactaaag atgagtttga ctgcaaagcc  3000
tgggcttatt tctctgatgt tgacctggaa aaagatgtgc actcaggcct gattggaccc  3060
cttctggtct gccacactaa cacactgaac cctgctcatg ggagacaagt gacagtacag  3120
gaatttgctc tgtttttcac catctttgat gagaccaaaa gctggtactt cactgaaaat  3180
atggaaagaa actgcagggc tccctgcaat atccagatgg aagatcccac ttttaaagag  3240
aattatcgct tccatgcaat caatggctac ataatggata cactacctgg cttagtaatg  3300
gctcaggatc aaaggattcg atggtatctg ctcagcatgg gcagcaatga aaacatccat  3360
tctattcatt tcagtggaca tgtgttcact gtacgaaaaa aagaggagta taaaatggca  3420
ctgtacaatc tctatccagg tgtttttgag acagtggaaa tgttaccatc caaagctgga  3480
atttggcggg tggaatgcct tattggcgag catctacatg ctgggatgag cacacttttt  3540
ctggtgtaca gcaataagtg tcagactccc ctgggaatgg cttctggaca cattagagat  3600
tttcagatta cagcttcagg acaatatgga cagtgggccc caaagctggc cagacttcat  3660
tattccggat caatcaatgc ctggagcacc aaggagccct tttcttggat caaggtggat  3720
ctgttggcac caatgattat tcacggcatc aagacccagg gtgcccgtca gaagttctcc  3780
agcctctaca tctctcagtt tatcatcatg tatagtcttg atgggaagaa gtggcagact  3840
tatcgaggaa attccactgg aaccttaatg gtcttctttg gcaatgtgga ttcatctggg  3900
ataaaacaca atatttttaa ccctccaatt attgctcgat acatccgttt gcacccaact  3960
cattatagca ttcgcagcac tcttcgcatg gagttgatgg gctgtgattt aaatagttgc  4020
agcatgccat tgggaatgga gagtaaagca atatcagatg cacagattac tgcttcatcc  4080
tactttacca atatgtttgc cacctggtct ccttcaaaag ctcgacttca cctccaaggg  4140
aggagtaatg cctggagacc tcaggtgaat aatccaaaag agtggctgca agtggacttc  4200
cagaagacaa tgaaagtcac aggagtaact actcagggag taaaatctct gcttaccagc  4260
atgtatgtga aggagttcct catctccagc agtcaagatg gccatcagtg gactctcttt  4320
tttcagaatg gcaaagtaaa ggtttttcag ggaaatcaag actccttcac acctgtggtg  4380
aactctctag acccaccgtt actgactcgc taccttcgaa ttcaccccca gagttgggtg  4440
caccagattg ccctgaggat ggaggttctg ggctgcgagg cacaggacct ctactga     4497
```

```
SEQ ID NO: 40           moltype = AA  length = 2122
FEATURE                 Location/Qualifiers
source                  1..2122
                        mol_type = protein
                        organism = synthetic construct
SEQUENCE: 40
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNPPVLK RHQREITRTT LQSDQEEIDY DDTISVEMKK  780
EDFDIYDEDE NQSPRSFQKK TRHYFIAAVE RLWDYGMSSS PHVLRNRAQS GSVPQFKKVV  840
```

```
FQEFTDGSFT QPLYRGELNE HLGLLGPYIR AEVEDNIMVT FRNQASRPYS FYSSLISYEE  900
DQRQGAEPRK NFVKPNETKT YFWKVQHHMA PTKDEFDCKA WAYFSDVDLE KDVHSGLIGP  960
LLVCHTNTLN PAHGRQVTVQ EFALFFTIFD ETKSWYFTEN MERNCRAPCN IQMEDPTFKE  1020
NYRFHAINGY IMDTLPGLVM AQDQRIRWYL LSMGSNENIH SIHFSGHVFT VRKKEEYKMA  1080
LYNLYPGVFE TVEMLPSKAG IWRVECLIGE HLHAGMSTLF LVYSNKCQTP LGMASGHIRD  1140
FQITASGQYG QWAPKLARLH YSGSINAWST KEPFSWIKVD LLAPMIIHGI KTQGARQKFS  1200
SLYISQFIIM YSLDGKKWQT YRGNSTGTLM VFFGNVDSSG IKHNIFNPPI IARYIRLHPT  1260
HYSIRSTLRM ELMGCDLNSC SMPLGMESKA ISDAQITASS YFTNMFATWS PSKARLHLQG  1320
RSNAWRPQVN NPKEWLQVDF QKTMKVTGVT TQGVKSLLTS MYVKEFLISS SQDGHQWTLF  1380
FQNGKVKVFQ GNQDSFTPVV NSLDPPLLTR YLRIHPQSWV HQIALRMEVL GCEAQDLYEI  1440
TRTTLQSDQE EIDYDDTISV EMKKEDFDIY DEDENQSPRS FQKKTRHYFI AAVERLWDYG  1500
MSSSPHVLRN RAQSGSVPQF KKVVFQEFTD GSFTQPLYRG ELNEHLGLLG PYIRAEVEDN  1560
IMVTFRNQAS RPYSFYSSLI SYEEDQRQGA EPRKNFVKPN ETKTYFWKVQ HHMAPTKDEF  1620
DCKAWAYFSD VDLEKDVHSG LIGPLLVCHT NTLNPAHGRQ VTVQEFALFF TIFDETKSWY  1680
FTENMERNCR APCNIQMEDP TFKENYRFHA INGYIMDTLP GLVMAQDQRI RWYLLSMGSN  1740
ENIHSIHFSG HVFTVRKKEE YKMALYNLYP GVFETVEMLP SKAGIWRVEC LIGEHLHAGM  1800
STLFLVYSNK CQTPLGMASG HIRDFQITAS GQYGQWAPKL ARLHYSGSIN AWSTKEPFSW  1860
IKVDLLAPMI IHGIKTQGAR QKFSSLYISQ FIIMYSLDGK KWQTYRGNST GTLMVFFGNV  1920
DSSGIKHNIF NPPIIARYIR LHPTHYSIRS TLRMELMGCD LNSCSMPLGM ESKAISDAQI  1980
TASSYFTNMF ATWSPSKARL HLQGRSNAWR PQVNNPKEWL QVDFQKTMKV TGVTTQGVKS  2040
LLTSMYVKEF LISSSQDGHQ WTLFFQNGKV KVFQGNQDSF TPVVNSLDPP LLTRYLRIHP  2100
QSWVHQIALR MEVLGCEAQD LY                                          2122

SEQ ID NO: 41          moltype = AA  length = 1455
FEATURE                Location/Qualifiers
source                 1..1455
                       mol_type = protein
                       organism = synthetic construct
SEQUENCE: 41
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNATNVS NNSNTSNDSN VSPPVLKRHQ REITRTTLQS  780
DQEEIDYDDT ISVEMKKEDF DIYDEDENQS PRSFQKKTRH YFIAAVERLW DYGMSSSPHV  840
LRNRAQSGSV PQFKKVVFQE FTDGSFTQPL YRGELNEHLG LLGPYIRAEV EDNIMVTFRN  900
QASRPYSFYS SLISYEEDQR QGAEPRKNFV KPNETKTYFW KVQHHMAPTK DEFDCKAWAY  960
FSDVDLEKDV HSGLIGPLLV CHTNTLNPAH GRQVTVQEFA LFFTIFDETK SWYFTENMER  1020
NCRAPCNIQM EDPTFKENYR FHAINGYIMD TLPGLVMAQD QRIRWYLLSM GSNENIHSIH  1080
FSGHVFTVRK KEEYKMALYN LYPGVFETVE MLPSKAGIWR VECLIGEHLH AGMSTLFLVY  1140
SNKCQTPLGM ASGHIRDFQI TASGQYGQWA PKLARLHYSG SINAWSTKEP FSWIKVDLLA  1200
PMIIHGIKTQ GARQKFSSLY ISQFIIMYSL DGKKWQTYRG NSTGTLMVFF GNVDSSGIKH  1260
NIFNPPIIAR YIRLHPTHYS IRSTLRMELM GCDLNSCSMP LGMESKAISD AQITASSYFT  1320
NMFATWSPSK ARLHLQGRSN AWRPQVNNPK EWLQVDFQKT MKVTGVTTQG VKSLLTSMYV  1380
KEFLISSSQD GHQWTLFFQN GKVKVFQGNQ DSFTPVVNSL DPPLLTRYLR IHPQSWVHQI  1440
ALRMEVLGCE AQDLY                                                  1455

SEQ ID NO: 42          moltype = AA  length = 1445
FEATURE                Location/Qualifiers
source                 1..1445
                       mol_type = protein
                       organism = synthetic construct
SEQUENCE: 42
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS QNPPVLKRHQ REITRTTLQS DQEEIDYDDT  780
ISVEMKKEDF DIYDEDENQS PRSFQKKTRH YFIAAVERLW DYGMSSSPHV LRNRAQSGSV  840
PQFKKVVFQE FTDGSFTQPL YRGELNEHLG LLGPYIRAEV EDNIMVTFRN QASRPYSFYS  900
SLISYEEDQR QGAEPRKNFV KPNETKTYFW KVQHHMAPTK DEFDCKAWAY FSDVDLEKDV  960
HSGLIGPLLV CHTNTLNPAH GRQVTVQEFA LFFTIFDETK SWYFTENMER NCRAPCNIQM  1020
EDPTFKENYR FHAINGYIMD TLPGLVMAQD QRIRWYLLSM GSNENIHSIH FSGHVFTVRK  1080
```

-continued

```
KEEYKMALYN LYPGVFETVE MLPSKAGIWR VECLIGEHLH AGMSTLFLVY SNKCQTPLGM  1140
ASGHIRDFQI TASGQYGQWA PKLARLHYSG SINAWSTKEP FSWIKVDLLA PMIIHGIKTQ  1200
GARQKFSSLY ISQFIIMYSL DGKKWQTYRG NSTGTLMVFF GNVDSSGIKH NIFNPPIIAR  1260
YIRLHPTHYS IRSTLRMELM GCDLNSCSMP LGMESKAISD AQITASSYFT NMFATWSPSK  1320
ARLHLQGRSN AWRPQVNNPK EWLQVDFQKT MKVTGVTTQG VKSLLTSMYV KEFLISSSQD  1380
GHQWTLFFQN GKVKVFQGNQ DSFTPVVNSL DPPLLTRYLR IHPQSWVHQI ALRMEVLGCE  1440
AQDLY                                                              1445

SEQ ID NO: 43          moltype = AA  length = 1496
FEATURE                Location/Qualifiers
source                 1..1496
                       mol_type = protein
                       organism = synthetic construct
SEQUENCE: 43
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSPPVLKRH QREITRTTLQ SDQEEIDYDD TISVEMKKED  840
FDIYDEDENQ SPRSFQKKTR HYFIAAVERL WDYGMSSSPH VLRNRAQSGS VPQFKKVVFQ  900
EFTDGSFTQP LYRGELNEHL GLLGPYIRAE VEDNIMVTFR NQASRPYSFY SSLISYEEDQ  960
RQGAEPRKNF VKPNETKTYF WKVQHHMAPT KDEFDCKAWA YFSDVDLEKD VHSGLIGPLL  1020
VCHTNTLNPA HGRQVTVQEF ALFFTIFDET KSWYFTENME RNCRAPCNIQ MEDPTFKENY  1080
RFHAINGYIM DTLPGLVMAQ DQRIRWYLLS MGSNENIHSI HFSGHVFTVR KKEEYKMALY  1140
NLYPGVFETV EMLPSKAGIW RVECLIGEHL HAGMSTLFLV YSNKCQTPLG MASGHIRDFQ  1200
ITASGQYGQW APKLARLHYS GSINAWSTKE PFSWIKVDLL APMIIHGIKT QGARQKFSSL  1260
YISQFIIMYS LDGKKWQTYR GNSTGTLMVF FGNVDSSGIK HNIFNPPIIA RYIRLHPTHY  1320
SIRSTLRMEL MGCDLNSCSM PLGMESKAIS DAQITASSYF TNMFATWSPS KARLHLQGRS  1380
NAWRPQVNNP KEWLQVDFQK TMKVTGVTTQ GVKSLLTSMY VKEFLISSSQ DGHQWTLFFQ  1440
NGKVKVFQGN QDSFTPVVNS LDPPLLTRYL RIHPQSWVHQ IALRMEVLGC EAQDLY      1496

SEQ ID NO: 44          moltype = AA  length = 1498
FEATURE                Location/Qualifiers
source                 1..1498
                       mol_type = protein
                       organism = synthetic construct
SEQUENCE: 44
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSQQNFVTQ RSKREITRTT LQSDQEEIDY DDTISVEMKK  840
EDFDIYDEDE NQSPRSFQKK TRHYFIAAVE RLWDYGMSSS PHVLRNRAQS GSVPQFKKVV  900
FQEFTDGSFT QPLYRGELNE HLGLLGPYIR AEVEDNIMVT FRNQASRPYS FYSSLISYEE  960
DQRQGAEPRK NFVKPNETKT YFWKVQHHMA PTKDEFDCKA WAYFSDVDLE KDVHSGLIGP  1020
LLVCHTNTLN PAHGRQVTVQ EFALFFTIFD ETKSWYFTEN MERNCRAPCN IQMEDPTFKE  1080
NYRFHAINGY IMDTLPGLVM AQDQRIRWYL LSMGSNENIH SIHFSGHVFT VRKKEEYKMA  1140
LYNLYPGVFE TVEMLPSKAG IWRVECLIGE HLHAGMSTLF LVYSNKCQTP LGMASGHIRD  1200
FQITASGQYG QWAPKLARLH YSGSINAWST KEPFSWIKVD LLAPMIIHGI KTQGARQKFS  1260
SLYISQFIIM YSLDGKKWQT YRGNSTGTLM VFFGNVDSSG IKHNIFNPPI IARYIRLHPT  1320
HYSIRSTLRM ELMGCDLNSC SMPLGMESKA ISDAQITASS YFTNMFATWS PSKARLHLQG  1380
RSNAWRPQVN NPKEWLQVDF QKTMKVTGVT TQGVKSLLTS MYVKEFLISS SQDGHQWTLF  1440
FQNGKVKVFQ GNQDSFTPVV NSLDPPLLTR YLRIHPQSWV HQIALRMEVL GCEAQDLY    1498

SEQ ID NO: 45          moltype = DNA  length = 4317
FEATURE                Location/Qualifiers
source                 1..4317
                       mol_type = other DNA
                       organism = synthetic construct
SEQUENCE: 45
gccaccagga gatactacct gggggctgtg gagctgagct gggactacat gcagtctgac  60
```

ctgggggagc tgcctgtgga tgccaggttc ccccccagag tgcccaagag cttccccttc 120
aacacctctg tggtgtacaa gaagaccctg tttgtggagt tcactgacca cctgttcaac 180
attgccaagc ccaggccccc ctggatgggc ctgctgggcc ccaccatcca ggctgaggtg 240
tatgacactg tggtgatcac cctgaagaac atggccagcc accctgtgag cctgcatgct 300
gtgggggtga gctactggaa ggcctctgag gggctgagt atgatgacca gaccagccag 360
agggagaagg aggatgacaa ggtgttccct gggggcagcc acacctatgt gtggcaggtg 420
ctgaaggaga atggccccat ggcctctgac cccctgtgcc tgacctacag ctacctgagc 480
catgtggacc tggtgaagga cctgaactct ggcctgattg gggccctgct ggtgtgcagg 540
gagggcagcc tggccaagga gaagacccag accctgcaca agttcatcct gctgtttgct 600
gtgtttgatg agggcaagag ctggcactct gaaaccaaga acagcctgat gcaggacagg 660
gatgctgcct ctgccagggc ctggcccaag atgcacactg tgaatggcta tgtgaacagg 720
agcctgcctg gcctgattgg ctgccacagg aagtctgtgt actggcatgt gattggcatg 780
ggcaccaccc ctgaggtgca cagcatcttc ctggagggcc acaccttcct ggtcaggaac 840
cacaggcagg ccagcctgga gatcagcccc atcaccttcc tgactgccca gaccctgctg 900
atggacctgg gccagttcct gctgttctgc cacatcagca gccaccagca tgatggcatg 960
gaggcctatg tgaaggtgga cagctgccct gaggagcccc agctgaggat gaagaacaat 1020
gaggaggctg aggactatga tgatgacctg actgactctg agatggatgt ggtgaggttt 1080
gatgatgaca acagccccag cttcatccag atcaggtctg tggccaagaa gcaccccaag 1140
acctgggtgc actacattgc tgctgaggag gaggactggg actatgcccc cctggtgctg 1200
gcccctgatg acaggagcta caagagccag tacctgaaca atggccccca gaggattggc 1260
aggaagtaca agaaggtcag gttcatggcc tacactgatg aaaccttcaa gaccagggag 1320
gccatccagc atgagtctgg catcctgggc cccctgctgt atggggaggt gggggacacc 1380
ctgctgatca tcttcaagaa ccaggccagc aggccctaca acatctaccc ccatggcatc 1440
actgatgtga ggcccctgta cagcaggagg ctgcccaagg gggtgaagca cctgaaggac 1500
ttccccatcc tgcctgggga gatcttcaag tacaagtgga ctgtgactgt ggaggatggc 1560
cccaccaagt ctgaccccag gtgcctgacc agatactaca gcagctttgt gaacatggag 1620
agggacctgg cctctggcct gattggcccc ctgctgatct gctacaagga gtctgtggac 1680
cagaggggca accagatcat gtctgacaag aggaatgtga tcctgttctc tgtgtttgat 1740
gagaacagga gctggtacct gactgagaac atccagaggt tcctgcccaa ccctgctggg 1800
gtgcagctgg aggaccctga gttccaggcc agcaacatca tgcacagcat caatggctat 1860
gtgtttgaca gcctgcagct gtctgtgtgc ctgcatgagg tggcctactg gtacatcctg 1920
agcattgggg cccagactga cttcctgtct gtgttcttct ctggctacac cttcaagcac 1980
aagatggtgt atgaggacac cctgaccctg ttccccttct ctggggagac tgtgttcatg 2040
agcatggaga accctggcct gtggattctg ggctgccaca actctgactt caggaacagg 2100
ggcatgactg ccctgctgaa agtctccagc tgtgacaaga acactgggga ctactatgag 2160
gacagctatg aggacatctc tgcctacctg ctgagcaaga acaatgccat tgagcccagg 2220
agcttcagcc agaatccccc agtgctgaag aggcaccaga gggagatcac caggaccacc 2280
ctgcagtctg accaggagga gattgactat gatgacacca tctctgtgga gatgaagaag 2340
gaggactttg acatctacga cgaggacgag aaccagagcc ccaggagctt ccagaagaag 2400
accaggcact acttcattgc tgctgtggag aggctgtggg actatggcat gagcagcagc 2460
ccccatgtgc tgaggaacag ggcccagtct ggctctgtgc cccagttcaa gaaggtggtg 2520
ttccaggagt tcactgatgg cagcttcacc cagcccctgt acagagggga gctgaatgag 2580
cacctgggcc tgctgggccc ctacatcagg gctgaggtgg aggacaacat catggtgacc 2640
ttcaggaacc aggccagcag gccctacagc ttctacagca gcctgatcag ctatgaggag 2700
gaccagaggc aggggctga gcccaggaag aactttgtga agcccaatga aaccaagacc 2760
tacttctgga aggtgcagca ccacatggcc cccaccaagg atgagtttga ctgcaaggcc 2820
tgggcctact tctctgatgt ggacctggag aaggatgtgc actctggcct gattggcccc 2880
ctgctggtgt gccacaccaa caccctgaac cctgcccatg gcaggcaggt gactgtgcag 2940
gagtttgccc tgttcttcac catctttgat gaaaccaaga gctggtactt cactgagaac 3000
atggagagga actgcagggc cccctgcaac atccagatgg aggaccccac cttcaaggag 3060
aactacaggt tccatgccat caatggctac atcatggaca ccctgcctgg cctggtgatg 3120
gcccaggacc agaggatcag gtggtacctg ctgagcatgg gcagcaatga gaacatccac 3180
agcatccact tctctggcca tgtgttcact gtgaggaaga aggaggagta caagatggcc 3240
ctgtacaacc tgtaccctgg ggtgtttgag actgtggaga tgctgcccag caaggctggc 3300
atctggaggg tggagtgcct gattggggag cacctgcatg ctggcatgag caccctgttc 3360
ctggtgtaca gcaacaagtg ccagaccccc ctgggcatgg cctctggcca catcagggac 3420
ttccagatca ctgcctctgg ccagtatggc cagtgggccc ccaagctggc caggctgcac 3480
tactctggca gcatcaatgc ctggagcacc aaggagccct tcagctggat caaggtggac 3540
ctgctggccc ccatgatcat ccatggcatc aagacccagg gggccaggca gaagttcagc 3600
agcctgtaca tcagccagtt catcatcatg tacagcctgg atggcaagaa gtggcagacc 3660
tacaggggca acagcactgg caccctgatg gtgttctttg gcaatgtgga cagctctggc 3720
atcaagcaca acatcttcaa cccccccatc attgccagat acatcaggct gcaccccacc 3780
cactacagca tcaggagcac cctgaggatg gagctgatgg gctgtgacct gaacagctgc 3840
agcatgcccc tgggcatgga gagcaaggcc atctctgatg cccagatcac tgccagcagc 3900
tacttcacca acatgtttgc cacctggagc cccagcaagg ccaggctgca cctgcagggc 3960
aggagcaatg cctggaggcc ccaggtcaac aaccccaagg agtggctgca ggtggacttc 4020
cagaagacca tgaaggtgac tggggtgacc acccaggggg tgaagagcct gctgaccagc 4080
atgtatgtga aggagttcct gatcagcagc agccaggatg gccaccagtg gaccctgttc 4140
ttccagaatg gcaaggtgaa ggtgttccag ggcaaccagg acagcttcac ccctgtggtg 4200
aacagcctgg acccccccct gctgaccaga tacctgagga ttcaccccca gagctgggtg 4260
caccagattg ccctgaggat ggaggtgctg ggctgtgagg cccaggacct gtactga 4317

SEQ ID NO: 46 moltype = DNA length = 5928
FEATURE Location/Qualifiers
source 1..5928
mol_type = other DNA
organism = synthetic construct
SEQUENCE: 46
ccccaactgg ggtaaccttt gggctccccg ggcgcgacta gtgaattcgt caatattggc 60

```
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcaaatag agctctccac ctgcttcttt ctgtgccttt  1140
tgcgattctg ctttagtgcc accagaagat actacctggg tgcagtggaa ctgtcatggg  1200
actatatgca aagtgatctc ggtgagctgc ctgtggacgc aagatttcct cctagagtgc  1260
caaaatcttt tccattcaac acctcagtcg tgtacaaaaa gactctgttt gtagaattca  1320
cggatcacct tttcaacatc gctaagccaa ggccaccctg gatgggtctg ctaggtccta  1380
ccatccaggc tgaggtttat gatacagtgg tcattacact taagaacatg gcttcccatc  1440
ctgtcagtct tcatgctgtt ggtgtatcct actggaaagc ttctgaggga gctgaatatg  1500
atgatcagac cagtcaaagg gagaaagaag atgataaagt cttccctggt ggaagccata  1560
catatgtctg gcaggtcctg aaagagaatg gtccaatggc ctctgaccca ctgtgcctta  1620
cctactcata tctttctcat gtggacctgg taaaagactt gaattcaggc ctcattggag  1680
ccctactagt atgtagagaa gggagtctgg ccaaggaaaa gacacagacc ttgcacaaat  1740
ttatactact ttttgctgta tttgatgaag ggaaaagttg gcactcagaa acaaagaact  1800
ccttgatgca ggatagggat gctgcatctg ctcgggcctg gcctaaaatg cacacagtca  1860
atggttatgt aaacaggtct ctgccaggtc tgattggatg ccacaggaaa tcagtctatt  1920
ggcatgtgat tggaatgggc accactcctg aagtgcactc aatattcctc gaaggtcaca  1980
catttcttgt gaggaaccat cgccaggcgt ccttggaaat ctcgccaata actttcctta  2040
ctgctcaaac actcttgatg gaccttggac agtttctact gttttgtcat atctcttccc  2100
accaacatga tggcatggaa gcttatgtca aagtagacag ctgtccagag gaaccccaac  2160
tacgaatgaa aaataatgaa gaagcggaag actatgatga tgatcttact gattctgaaa  2220
tggatgtggt caggtttgat gatgacaact ctccttcctt tatccaaatt cgctcagttg  2280
ccaagaagca tcctaaaact tgggtacatt acattgctgc tgaagaggag gactgggact  2340
atgctccctt agtcctcgcc cccgatgaca gaagttataa aagtcaatat ttgaacaatg  2400
gccctcagcg gattggtagg aagtacaaaa aagtccgatt tatggcatac acagatgaaa  2460
cctttaagac tcgtgaagct attcagcatg aatcaggaat cttgggacct ttactttatg  2520
gggaagttgg agacacactg ttgattatat ttaagaatca agcaagcaga ccatataaca  2580
tctaccctca cggaatcact gatgtccgtc ctttgtattc aaggagatta ccaaaaggtg  2640
taaaacattt gaaggatttt ccaattctgc caggagaaat attcaaatat aaatggacag  2700
tgactgtaga agatgggcca actaaatcag atcctcggtg cctgacccgc tattactcta  2760
gtttcgttaa tatggagaga gatctagctt caggactcat tggccctctc ctcatctgct  2820
acaaagaatc tgtagatcaa agaggaaacc agataatgtc agacaagagg aatgtcatcc  2880
tgttttctgt atttgatgag aaccgaagct ggtacctcac agagaatata caacgctttc  2940
tccccaatcc agctggagtg cagcttgagg atccagagtt ccaagcctcc aacatcatgc  3000
acagcatcaa tggctatgtt tttgatagtt tgcagttgtc agtttgtttg catgaggtgg  3060
catactggta cattctaagc attggagcac agactgactt cctttctgtc ttcttctctg  3120
gatatacctt caaacacaaa atggtctatg aagacacact caccctattc ccattctcag  3180
gagaaactgt cttcatgtcg atggaaaacc caggtctatg gattctgggg tgccacaact  3240
cagactttcg gaacagaggc atgaccgcct tactgaaggt ttctagttgt gacaagaaca  3300
ctggtgatta ttacgaggac agttatgaag atatttcagc atacttgctg agtaaaaaca  3360
atgccattga accaagaagc ttcagccaga atagcagaca ccctagcacc agacagaaac  3420
agtttaatgc cactaatgtg agcaacaaca gcaacaccag caatgacagc aatgtgtcta  3480
acaagacatc taacaacagc aatgccacaa acaagaccaa caacacaaat gatagcacaa  3540
acaggaccaa ccagaccaat accagccccc ctgtgctgaa gagacatcag agggaaataa  3600
ctcgtactac tcttcagtca gatcaagagg aaattgacta tgatgatacc atatcagttg  3660
aaatgaagaa ggaagatttt gacatttatg atgaggatga aaatcagagc cccegcagct  3720
ttcaaaagaa aacacgacac tattttattg ctgcagtgga gaggctctgg gattatggga  3780
tgagtagctc cccacatgtt ctaagaaaca gggctcagag tggcagtgtc cctcagttca  3840
agaaagttgt tttccaggaa tttactgatg gctcctttac tcagccctta taccgtggag  3900
aactaaatga acatttggga ctcctggggc catatataag agcagaagtt gaagataata  3960
tcatggtaac tttcagaaat caggcctctc gtccctattc cttctattct agccttattt  4020
cttatgagga agatcagagg caaggagcag aacctagaaa aaactttgtc aagcctaatg  4080
aaaccaaaac ttacttttgg aaagtgcaac atcatatggc acccactaaa gatgagtttg  4140
actgcaaagc ctgggcttat ttctctgatg ttgacctgga aaaagatgtg cactcaggcc  4200
tgattggacc ccttctggtc tgccacacta acacactgaa ccctgctcat gggagacaag  4260
tgacagtaca ggaatttgct ctgtttttca ccatctttga tgagaccaaa agctggtact  4320
tcactgaaaa tatggaaaga aactgcaggg ctccctgcaa tatccagatg gaagatccca  4380
cttttaaaga gaattatcgc ttccatgcaa tcaatggcta cataatggat acactacctg  4440
gcttagtaat ggctcaggat caaaggattc gatggtatct gctcagcatg ggcagcaatg  4500
aaaacatcca ttctattcat ttcagtggac atgtgttcac tgtacgaaaa aaagaggagt  4560
ataaaatggc actgtacaat ctctatccag gtgtttttga gacagtggaa atgttaccat  4620
ccaaagctgg aatttggcgg gtggaatgcc ttattggcga gcatctacat gctgggatga  4680
gcacactttt tctggtgtac agcaataagt gtcagactcc cctgggaatg gcttctggac  4740
acattagaga ttttcagatt acagcttcag gacaatatgg acagtgggcc ccaaagctgg  4800
```

```
ccagacttca ttattccgga tcaatcaatg cctggagcac caaggagccc ttttcttgga  4860
tcaaggtgga tctgttggca ccaatgatta ttcacggcat caagacccag ggtgcccgtc  4920
agaagttctc cagcctctac atctctcagt ttatcatcat gtatagtctt gatgggaaga  4980
agtggcagac ttatcgagga aattccactg gaaccttaat ggtcttcttt ggcaatgtgg  5040
attcatctgg gataaaacac aatattttta accctccaat tattgctcga tacatccgtt  5100
tgcacccaac tcattatagc attcgcagca ctcttcgcat ggagttgatg ggctgtgatt  5160
taaatagttg cagcatgcca ttgggaatgg agagtaaagc aatatcagat gcacagatta  5220
ctgcttcatc ctactttacc aatatgtttg ccacctggtc tccttcaaaa gctcgacttc  5280
acctccaagg gaggagtaat gcctggagac ctcaggtgaa taatccaaaa gagtggctgc  5340
aagtggactt ccagaagaca atgaaagtca caggagtaac tactcaggga gtaaaatctc  5400
tgcttaccag catgtatgtg aaggagttcc tcatctccag cagtcaagat ggccatcagt  5460
ggactctctt ttttcagaat ggcaaagtaa aggtttttca gggaaatcaa gactccttca  5520
cacctgtggt gaactctcta gacccaccgt tactgactcg ctaccttcga attcaccccc  5580
agagttgggt gcaccagatt gccctgagga tggaggttct gggctgcgag gcacaggacc  5640
tctactgaga tatctctaga gtcgacagta ctggtgatca gcctcgactg tgccttctag  5700
ttgccagcca tctgttgttt gcccctcccc cgtgccttcc ttgaccctgg aaggtgccac  5760
tcccactgtc ctttcctaat aaaatgagga aattgcatcg cattgtctga gtaggtgtca  5820
ttctattctg gggggtgggg tggggcagga cagcaagggg gaggattggg aagacaatag  5880
caggcatgct ggggatgcgg tgggctctat ggaaccagct ggggcccg              5928

SEQ ID NO: 47           moltype = DNA  length = 5934
FEATURE                 Location/Qualifiers
source                  1..5934
                        mol_type = other DNA
                        organism = synthetic construct
SEQUENCE: 47
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcaaatag agctctccac ctgcttcttt ctgtgccttt  1140
tgcgattctg ctttagtgcc accagaagat actacctggg tgcagtggaa ctgtcatggg  1200
actatatgca aagtgatctc ggtgagctgc ctgtggacgc aagatttcct cctagagtgc  1260
caaaatcttt tccattcaac acctcagtcg tgtacaaaaa gactctgttt gtagaattca  1320
cggatcacct tttcaacatc gctaagccaa ggccaccctg gatgggtctg ctaggtccta  1380
ccatccaggc tgaggtttat gatacagtgg tcattacact taagaacatg gcttcccatc  1440
ctgtcagtct tcatgctgtt ggtgtatcct actggaaagc ttctgaggga gctgaatatg  1500
atgatcagac cagtcaaagg gagaaagaag atgataaagt cttccctggt ggaagccata  1560
catatgtctg gcaggtcctg aaagagaatg gtccaatggc ctctgaccca ctgtgcctta  1620
cctactcata tctttctcat gtggacctgg taaaagactt gaattcaggc ctcattggag  1680
ccctactagt atgtagagaa gggagtctgg ccaaggaaaa gacacagacc ttgcacaaat  1740
ttatactact ttttgctgta tttgatgaag ggaaaagttg gcactcagaa acaaagaact  1800
ccttgatgca ggatagggat gctgcatctg ctcgggcctg gcctaaaatg cacacagtca  1860
atggttatgt aaacaggtct ctgccaggtc tgattggatg ccacaggaaa tcagtctatt  1920
ggcatgtgat tggaatgggc accactcctg aagtgcactc aatattcctc gaaggtcaca  1980
catttcttgt gaggaaccat cgccaggcgt ccttggaaat ctcgccaata actttcctta  2040
ctgctcaaac actcttgatg gaccttggac agtttctact gttttgtcat atctcttccc  2100
accaacatga tggcatggaa gcttatgtca aagtagacag ctgtccagag gaaccccaac  2160
tacgaatgaa aaataatgaa gaagcggaag actatgatga tgatcttact gattctgaaa  2220
tggatgtggt caggtttgat gatgacaact ctccttcctt tatccaaatt cgctcagttg  2280
ccaagaagca tcctaaaact tgggtacatt acattgctgc tgaagaggag gactgggact  2340
atgctccctt agtcctcgcc cccgatgaca gaagttataa aagtcaatat ttgaacaatg  2400
gccctcagcg gattggtagg aagtacaaaa aagtccgatt tatggcatac acagatgaaa  2460
cctttaagac tcgtgaagct attcagcatg aatcaggaat cttgggacct ttactttatg  2520
gggaagttgg agacacactg ttgattatat ttaagaatca agcaagcaga ccatataaca  2580
tctaccctca cggaatcact gatgtccgtc ctttgtattc aaggagatta ccaaaaggtg  2640
taaaacattt gaaggatttt ccaattctgc caggagaaat attcaaatat aaatggacag  2700
tgactgtaga agatgggcca actaaatcag atcctcggtg cctgacccgc tattactcta  2760
gtttcgttaa tatggagaga gatctagctt caggactcat tggccctctc ctcatctgct  2820
acaaagaatc tgtagatcaa agaggaaacc agataatgtc agacaagagg aatgtcatcc  2880
tgttttctgt atttgatgag aaccgaagct ggtacctcac agagaatata caacgctttc  2940
tccccaatcc agctggagtg cagcttgagg atccagagtt ccaagcctcc aacatcatgc  3000
acagcatcaa tggctatgtt tttgatagtt tgcagttgtc agtttgtttg catgaggtgg  3060
catactggta cattctaagc attggagcac agactgactt cctttctgtc ttcttctctg  3120
gatatacctt caaacacaaa atggtctatg aagacacact caccctattc ccattctcag  3180
```

```
gagaaactgt cttcatgtcg atggaaaacc caggtctatg gattctgggg tgccacaact  3240
cagactttcg gaacagaggc atgaccgcct tactgaaggt ttctagttgt gacaagaaca  3300
ctggtgatta ttacgaggac agttatgaag atatttcagc atacttgctg agtaaaaaca  3360
atgccattga accaagaagc ttcagccaga attctagaca ccctagcacc agacagaaac  3420
agtttaatgc cactaatgtg tctaacaaca gcaacaccag caatgacagc aatgtgtcta  3480
acaagacatc taacaacagc aacgccacaa acaagaccaa caacacaaat gatagcacaa  3540
accggaccaa ccagaccaat accagccagc agaacttcgt gacccagaga agtaagagag  3600
aaataactcg tactactctt cagtcagatc aagaggaaat tgactatgat gataccatat  3660
cagttgaaat gaagaaggaa gattttgaca tttatgatga ggatgaaaat cagagccccc  3720
gcagctttca aaagaaaaca cgacactatt ttattgctgc agtggagagg ctctgggatt  3780
atgggatgag tagctcccca catgttctaa gaaacagggc tcagagtggc agtgtccctc  3840
agttcaagaa agttgtttc caggaattta ctgatggctc ctttactcag cccttatacc  3900
gtggagaact aaatgaacat ttgggactcc tggggccata tataagagca gaagttgaag  3960
ataaatatcat ggtaactttc agaaatcagg cctctcgtcc ctattccttc tattctagcc  4020
ttatttctta tgaggaagat cagaggcaag gagcagaacc tagaaaaaac tttgtcaagc  4080
ctaatgaaac caaaacttac ttttggaaag tgcaacatca tatggcaccc actaaagatg  4140
agtttgactg caaagcctgg gcttatttct ctgatgttga cctggaaaaa gatgtgcact  4200
caggcctgat tggacccctt ctggtctgcc acactaacac actgaaccct gctcatggga  4260
gacaagtgac agtacaggaa tttgctctgt tttcaccat ctttgatgag accaaaagct  4320
ggtacttcac tgaaaatatg gaaagaaact gcagggctcc ctgcaatatc cagatggaag  4380
atcccacttt taaagagaat tatcgcttcc atgcaatcaa tggctacata atggatacac  4440
tacctggctt agtaatggct caggatcaaa ggattcgatg gtatctgctc agcatgggca  4500
gcaatgaaaa catccattct attcatttca gtggacatgt gttcactgta cgaaaaaaag  4560
aggagtataa aatggcactg tacaatctct atccaggtgt tttgagaca gtggaaatgt  4620
taccatccaa agctggaatt tggcgggtgg aatgccttat tggcgagcat ctacatgctg  4680
ggatgagcac actttttctg gtgtacagca ataagtgtca gactcccctg ggaatggctt  4740
ctggacacat tagagatttt cagattacag cttcaggaca atatggacag tgggccccaa  4800
agctggccag acttcattat tccggatcaa tcaatgcctg gagcaccaag gagccctttt  4860
cttggatcaa ggtggatctg ttggcaccaa tgattattca cggcatcaag acccagggtg  4920
cccgtcagaa gttctccagc ctctacatct ctcagtttat catcatgtat agtcttgatg  4980
ggaagaagtg gcagacttat cgaggaaatt ccactggaac cttaatggtc ttctttggca  5040
atgtggattc atctgggata aaacacaata tttttaaccc tccaattatt gctcgataca  5100
tccgtttgca cccaactcat tatagcattc gcagcactct tcgcatggag ttgatgggct  5160
gtgatttaaa tagttgcagc atgccattgg gaatggagag taaagcaata tcagatgcac  5220
agattactgc ttcatcctac tttaccaata tgtttgccac ctggtctcct tcaaaagctc  5280
gacttcacct ccaagggagg agtaatgcct ggagacctca ggtgaataat ccaaaagagt  5340
ggctgcaagt ggacttccag aagacaatga aagtcacagg agtaactact cagggagtaa  5400
aatctctgct taccagcatg tatgtgaagg agttcctcat ctccagcagt caagatggcc  5460
atcagtggac tctcttttt cagaatggca aagtaaaggt tttcaggga aatcaagact  5520
ccttcacacc tgtggtgaac tctctagacc caccgttact gactcgctac cttcgaattc  5580
acccccagag ttgggtgcac cagattgccc tgaggatgga ggttctgggc tgcgaggcac  5640
aggacctcta ctgagatatc tctagagtcg acagtactgg tgatcagcct cgactgtgcc  5700
ttctagttgc cagccatctg ttgtttgccc ctcccccgtg ccttccttga ccctggaagg  5760
tgccactccc actgtccttt cctaataaaa tgaggaaatt gcatcgcatt gtctgagtag  5820
gtgtcattct attctggggg gtggggtggg gcaggacagc aagggggagg attgggaaga  5880
caatagcagg catgctgggg atgcggtggg ctctatggaa ccagctgggg cccg        5934
```

```
SEQ ID NO: 48           moltype = DNA  length = 5754
FEATURE                 Location/Qualifiers
source                  1..5754
                        mol_type = other DNA
                        organism = synthetic construct
SEQUENCE: 48
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg agctgagcac ctgcttcttc ctgtgcctgc  1140
tgaggttctg cttctctgcc accaggagat actacctggg ggctgtggag ctgagctggg  1200
actacatgca gtctgacctg gggagctgc ctgtggatgc caggttcccc cccagagtgc  1260
ccaagagctt ccccttcaac acctctgtgg tgtacaagaa gaccctgttt gtggagttca  1320
ctgaccacct gttcaacatt gccaagccca ggccccctg gatgggcctg ctgggcccca  1380
ccatccaggc tgaggtgtat gacactgtgg tgatcaccct gaagaacatg gccagccacc  1440
ctgtgagcct gcatgctgtg gggtgagct actggaaggc ctctgagggg gctgagtatg  1500
atgaccagac cagccagagg gagaaggagg atgacaaggt gttccctggg ggcagccaca  1560
```

```
cctatgtgtg gcaggtgctg aaggagaatg gccccatggc ctctgacccc ctgtgcctga  1620
cctacagcta cctgagccat gtggacctgg tgaaggacct gaactctggc ctgattgggg  1680
ccctgctggt gtgcagggag ggcagcctgg ccaaggagaa gacccagacc ctgcacaagt  1740
tcatcctgct gtttgctgtg tttgatgagg gcaagagctg gcactctgaa accaagaaca  1800
gcctgatgca ggacagggat gctgcctctg ccagggcctg gcccaagatg cacactgtga  1860
atggctatgt gaacaggagc ctgcctggcc tgattggctg ccacaggaag tctgtgtact  1920
ggcatgtgat tggcatgggc accacccctg aggtgcacag catcttcctg gagggccaca  1980
ccttcctggt caggaaccac aggcaggcca gcctggagat cagccccatc accttcctga  2040
ctgcccagac cctgctgatg gacctgggcc agttcctgct gttctgccac atcagcagcc  2100
accagcatga tggcatggag gcctatgtga aggtggacag ctgccctgag gagccccagc  2160
tgaggatgaa gaacaatgag gaggctgagg actatgatga tgacctgact gactctgaga  2220
tggatgtggt gaggtttgat gatgacaaca gccccagctt catccagatc aggtctgtgg  2280
ccaagaagca ccccaagacc tgggtgcact acattgctgc tgaggaggag gactgggact  2340
atgcccccct ggtgctggcc cctgatgaca ggagctacaa gagccagtac ctgaacaatg  2400
gcccccagag gattggcagg aagtacaaga aggtcaggtt catggcctac actgatgaaa  2460
ccttcaagac cagggaggcc atccagcatg agtctggcat cctgggcccc ctgctgtatg  2520
gggaggtggg ggacaccctg ctgatcatct tcaagaacca ggccagcagg ccctacaaca  2580
tctaccccca tggcatcact gatgtgaggc ccctgtacag caggaggctg cccaaggggg  2640
tgaagcacct gaaggacttc cccatcctgc ctggggagat cttcaagtac aagtggactg  2700
tgactgtgga ggatggcccc accaagtctg accccaggtg cctgaccaga tactacagca  2760
gctttgtgaa catggagagg gacctggcct ctggcctgat tggcccctg ctgatctgct  2820
acaaggagtc tgtggaccag aggggcaacc agatcatgtc tgacaagagg aatgtgatcc  2880
tgttctctgt gtttgatgag aacaggagct ggtacctgac tgagaacatc cagaggttcc  2940
tgcccaaccc tgctggggtg cagctggagg accctgagtt ccaggccagc aacatcatgc  3000
acagcatcaa tggctatgtg tttgacagcc tgcagctgtc tgtgtgcctg catgaggtgg  3060
cctactggta catcctgagc attggggccc agactgactt cctgtctgtg ttcttctctg  3120
gctacacctt caagcacaag atggtgtatg aggacaccct gaccctgttc cccttctctg  3180
gggagactgt gttcatgagc atggagaacc ctggcctgtg gattctgggc tgccacaact  3240
ctgacttcag gaacaggggc atgactgccc tgctgaaagt ctccagctgt gacaagaaca  3300
ctggggacta ctatgaggac agctatgagg acatctctgc ctacctgctg agcaagaaca  3360
atgccattga gcccaggagc ttcagccaga atcccccagt gctgaagagg caccagaggg  3420
agatcaccag gaccaccctg cagtctgacc aggaggagat tgactatgat gacaccatct  3480
ctgtggagat gaagaaggag gactttgaca tctacgacga ggacgagaac cagagcccca  3540
ggagcttcca gaagaagacc aggcactact tcattgctgc tgtggagagg ctgtgggact  3600
atggcatgag cagcagcccc catgtgctga ggaacagggc ccagtctggc tctgtgcccc  3660
agttcaagaa ggtggtgttc caggagttca ctgatggcag cttcacccag cccctgtaca  3720
gaggggagct gaatgagcac ctgggcctgc tgggccccta catcagggct gaggtggagg  3780
acaacatcat ggtgaccttc aggaaccagg ccagcaggcc ctacagcttc tacagcagcc  3840
tgatcagcta tgaggaggac cagaggcagg gggctgagcc caggaagaac tttgtgaagc  3900
ccaatgaaac caagacctac ttctggaagg tgcagcacca catggccccc accaaggatg  3960
agtttgactg caaggcctgg gcctacttct ctgatgtgga cctggagaag gatgtgcact  4020
ctggcctgat tggcccctg ctggtgtgcc acaccaacac cctgaaccct gcccatggca  4080
ggcaggtgac tgtgcaggag tttgccctgt tcttcaccat ctttgatgaa accaagagct  4140
ggtacttcac tgagaacatg gagaggaact gcagggcccc ctgcaacatc cagatggagg  4200
accccacctt caaggagaac tacaggttcc atgccatcaa tggctacatc atggacaccc  4260
tgcctggcct ggtgatggcc caggaccaga ggatcaggtg gtacctgctg agcatgggca  4320
gcaatgagaa catccacagc atccacttct ctggccatgt gttcactgtg aggaagaagg  4380
aggagtacaa gatggccctg tacaacctgt accctggggt gtttgagact gtggagatgc  4440
tgcccagcaa ggctggcatc tggagggtgg agtgcctgat tggggagcac ctgcatgctg  4500
gcatgagcac cctgttcctg gtgtacagca acaagtgcca gacccccctg ggcatggcct  4560
ctggccacat cagggacttc cagatcactg cctctggcca gtatggccag tgggccccca  4620
agctggccag gctgcactac tctggcagca tcaatgcctg gagcaccaag gagcccttca  4680
gctggatcaa ggtggacctg ctggccccca tgatcatcca tggcatcaag acccaggggg  4740
ccaggcagaa gttcagcagc ctgtacatca gccagttcat catcatgtac agcctggatg  4800
gcaagaagtg gcagacctac aggggcaaca gcactggcac cctgatggtg ttctttggca  4860
atgtggacag ctctggcatc aagcacaaca tcttcaaccc ccccatcatt gccagataca  4920
tcaggctgca ccccacccac tacagcatca ggagcaccct gaggatggag ctgatgggct  4980
gtgacctgaa cagctgcagc atgcccctgg gcatggagag caaggccatc tctgatgccc  5040
agatcactgc cagcagctac ttcaccaaca tgtttgccac ctggagcccc agcaaggcca  5100
ggctgcacct gcagggcagg agcaatgcct ggaggcccca ggtcaacaac cccaaggagt  5160
ggctgcaggt ggacttccag aagaccatga aggtgactgg ggtgaccacc cagggggtga  5220
agagcctgct gaccagcatg tatgtgaagg agttcctgat cagcagcagc caggatggcc  5280
accagtggac cctgttcttc cagaatggca aggtgaaggt gttccagggc aaccaggaca  5340
gcttcacccc tgtggtgaac agcctggacc ccccctgct gaccagatac ctgaggattc  5400
acccccagag ctgggtgcac cagattgccc tgaggatgga ggtgctgggc tgtgaggccc  5460
aggacctgta ctgagatatc tctagagtcg acagtactgg tgatcagcct cgactgtgcc  5520
ttctagttgc cagccatctg ttgtttgccc ctcccccgtg ccttccttga ccctggaagg  5580
tgccactccc actgtccttt cctaataaaa tgaggaaatt gcatcgcatt gtctgagtag  5640
gtgtcattct attctggggg gtggggtggg gcaggacagc aagggggagg attgggaaga  5700
caatagcagg catgctgggg atgcggtggg ctctatggaa ccagctgggg cccg        5754

SEQ ID NO: 49           moltype = DNA  length = 5754
FEATURE                 Location/Qualifiers
source                  1..5754
                        mol_type = other DNA
                        organism = synthetic construct
SEQUENCE: 49
ccccaactgg ggtaaccttt gggctccccg ggcgcgacta gtgaattcgt caatattggc  60
cattagccat attattcatt ggttatatag cataaatcaa tattggctat tggccattgc  120
```

-continued

```
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg gggggagctgc ctgtggatgc taggttcccc cctagagtgc  1260
ccaagtcctt cccccttcaac acttctgtgg tgtacaagaa gaccctgttt gtggagttca  1320
ctgaccacct gtttaacatt gccaagccca ggccccccttg gatgggcctg ctgggggccca  1380
ccatccaggc tgaggtgtat gacactgtgg tgatcaccct gaagaacatg gccagccatc  1440
ctgtgagcct gcatgctgtg ggggtgagct actggaaggc cagcgagggg gctgagtatg  1500
atgaccagac tagccagagg gagaaggagg atgacaaggt gtttcctgga ggcagcccaca  1560
cctatgtgtg gcaggtgctg aaggagaatg gccccatggc ctctgacccc ctgtgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaacccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gttttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga atccccctgt gctgaagaga catcagaggg  3420
agatcaccag gactaccctg cagtctgatc aggaggagat tgactatgat gacacaatct  3480
ctgtggagat gaagaaggag gattttgaca tctatgatga ggatgagaac cagagcccca  3540
gatcttttca gaagaagacc agacactact tcattgctgc tgtggagagg ctgtgggact  3600
atggcatgag cagcagccct catgtgctga ggaacagggc ccagtctggc tctgtgcccc  3660
agttcaagaa ggtggtgttc caggagttta ctgatggcag cttcacccag cccctgtaca  3720
gaggggagct gaatgagcac ctgggcctgc tgggccctta tatcagggct gaggtggagg  3780
ataacattat ggtgactttc aggaaccagg cctctaggcc ctacagcttc tatagcagcc  3840
tgatctctta tgaggaggat cagaggcagg gggctgagcc cagaaagaac tttgtgaagc  3900
ctaatgagac taagacctac ttctggaagg tccagcacca catggccccc accaaggatg  3960
agtttgattg caaggcctgg gcctatttct ctgatgtgga cctggagaag gatgtccatt  4020
ctggcctgat tggccctctg ctggtgtgcc acactaacac tctgaatcct gcccatggca  4080
ggcaggtgac tgtccaggag tttgccctgt tcttcactat ctttgatgag accaagagct  4140
ggtactttac tgagaacatg gagagaaact gcagggctcc ttgcaatatc cagatggagg  4200
accccacctt caaggagaac tacaggtttc atgccatcaa tgggtacatc atggacaccc  4260
tgcctggcct ggtgatggct caggaccaga gaatcagatg gtatctgctg agcatgggca  4320
gcaatgagaa tatccacagc atccacttct ctggacatgt gttcactgtg aggaagaagg  4380
aggagtacaa gatggctctg tataatctgt accctggagt gtttgaaact gtggagatgc  4440
tgccttctaa ggctggcatc tggagggtgg agtgcctgat tggggagcac ctgcatgctg  4500
gcatgagcac cctgttcctg gtgtacagca acaagtgtca gaccccccctg ggcatggcct  4560
ctggacacat cagggacttc cagatcacag cctctggcca gtatggccag tgggccccca  4620
agctggccag gctgcattat tctggcagca tcaatgcctg gtctaccaag gagcccttta  4680
gctggatcaa ggtggacctg ctggccccca tgattatcca tggcatcaag acccaggggg  4740
ccaggcagaa gttctctagc ctgtacatca gccagttcat catcatgtac tctctggatg  4800
gcaagaagtg gcagacctac aggggcaaca gcactggcac actgatggtg ttctttggca  4860
```

```
atgtggacag ctctggcatc aagcacaaca tcttcaatcc ccccattatc gctaggtata  4920
ttaggctgca tcccacccac tacagcatca gatctaccct gagaatggag ctgatgggct  4980
gtgacctgaa ctcttgcagc atgcccctgg gcatggagtc taaggccatc tctgatgccc  5040
agattactgc cagcagctac ttcaccaata tgtttgccac ctggagccct tctaaggcca  5100
ggctgcatct gcaggggagg agcaatgcct ggaggcctca ggtgaacaac cctaaggagt  5160
ggctgcaggt ggatttccag aagaccatga aggtgactgg agtgaccacc cagggagtca  5220
agagcctgct gaccagcatg tatgtgaagg agtttctgat cagctctagc caggatggcc  5280
accagtggac tctgttcttt cagaatggga aggtgaaggt gtttcagggc aatcaggact  5340
ctttcacccc tgtggtgaac agcctggacc ccccccctgct gaccagatac ctgagaatcc  5400
acccccagag ctgggtgcac cagatcgccc tgaggatgga ggtgctgggc tgtgaggctc  5460
aggatctgta ctgagatatc tctagagtcg acagtactgg tgatcagcct cgactgtgcc  5520
ttctagttgc cagccatctg ttgtttgccc ctcccccgtg ccttccttga ccctggaagg  5580
tgccactccc actgtccttt cctaataaaa tgaggaaatt gcatcgcatt gtctgagtag  5640
gtgtcattct attctggggg gtggggtggg gcaggacagc aagggggagg attgggaaga  5700
caatagcagg catgctgggg atgcggtggg ctctatggaa ccagctgggg cccg        5754

SEQ ID NO: 50          moltype = AA  length = 1496
FEATURE                Location/Qualifiers
source                 1..1496
                       mol_type = protein
                       organism = synthetic construct
SEQUENCE: 50
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSPPVLKHH QREITRTTLQ SDQEEIDYDD TISVEMKKED  840
FDIYDEDENQ SPRSFQKKTR HYFIAAVERL WDYGMSSSPH VLRNRAQSGS VPQFKKVVFQ  900
EFTDGSFTQP LYRGELNEHL GLLGPYIRAE VEDNIMVTFR NQASRPYSFY SSLISYEEDQ  960
RQGAEPRKNF VKPNETKTYF WKVQHHMAPT KDEFDCKAWA YFSDVDLEKD VHSGLIGPLL  1020
VCHTNTLNPA HGRQVTVQEF ALFFTIFDET KSWYFTENME RNCRAPCNIQ MEDPTFKENY  1080
RFHAINGYIM DTLPGLVMAQ DQRIRWYLLS MGSNENIHSI HFSGHVFTVR KKEEYKMALY  1140
NLYPGVFETV EMLPSKAGIW RVECLIGEHL HAGMSTLFLV YSNKCQTPLG MASGHIRDFQ  1200
ITASGQYGQW APKLARLHYS GSINAWSTKE PFSWIKVDLL APMIIHGIKT QGARQKFSSL  1260
YISQFIIMYS LDGKKWQTYR GNSTGTLMVF FGNVDSSGIK HNIFNPPIIA RYIRLHPTHY  1320
SIRSTLRMEL MGCDLNSCSM PLGMESKAIS DAQITASSYF TNMFATWSPS KARLHLQGRS  1380
NAWRPQVNNP KEWLQVDFQK TMKVTGVTTQ GVKSLLTSMY VKEFLISSSQ DGHQWTLFFQ  1440
NGKVKVFQGN QDSFTPVVNS LDPPLLTRYL RIHPQSWVHQ IALRMEVLGC EAQDLY      1496

SEQ ID NO: 51          moltype = AA  length = 1496
FEATURE                Location/Qualifiers
source                 1..1496
                       mol_type = protein
                       organism = synthetic construct
SEQUENCE: 51
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLSC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSPPVLKRH QREITRTTLQ SDQEEIDYDD TISVEMKKED  840
FDIYDEDENQ SPRSFQKKTR HYFIAAVERL WDYGMSSSPH VLRNRAQSGS VPQFKKVVFQ  900
EFTDGSFTQP LYRGELNEHL GLLGPYIRAE VEDNIMVTFR NQASRPYSFY SSLISYEEDQ  960
RQGAEPRKNF VKPNETKTYF WKVQHHMAPT KDEFDCKAWA YFSDVDLEKD VHSGLIGPLL  1020
VCHTNTLNPA HGRQVTVQEF ALFFTIFDET KSWYFTENME RNCRAPCNIQ MEDPTFKENY  1080
RFHAINGYIM DTLPGLVMAQ DQRIRWYLLS MGSNENIHSI HFSGHVFTVR KKEEYKMALY  1140
NLYPGVFETV EMLPSKAGIW RVECLIGEHL HAGMSTLFLV YSNKCQTPLG MASGHIRDFQ  1200
ITASGQYGQW APKLARLHYS GSINAWSTKE PFSWIKVDLL APMIIHGIKT QGARQKFSSL  1260
YISQFIIMYS LDGKKWQTYR GNSTGTLMVF FGNVDSSGIK HNIFNPPIIA RYIRLHPTHY  1320
SIRSTLRMEL MGCDLNSCSM PLGMESKAIS DAQITASSYF TNMFATWSPS KARLHLQGRS  1380
NAWRPQVNNP KEWLQVDFQK TMKVTGVTTQ GVKSLLTSMY VKEFLISSSQ DGHQWTLFFQ  1440
NGKVKVFQGN QDSFTPVVNS LDPPLLTRYL RIHPQSWVHQ IALRMEVLGC EAQDLY      1496
```

```
SEQ ID NO: 52          moltype = AA  length = 1496
FEATURE                Location/Qualifiers
source                 1..1496
                       mol_type = protein
                       organism = synthetic construct
SEQUENCE: 52
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLSC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSPPVLKHH QREITRTTLQ SDQEEIDYDD TISVEMKKED  840
FDIYDEDENQ SPRSFQKKTR HYFIAAVERL WDYGMSSSPH VLRNRAQSGS VPQFKKVVFQ  900
EFTDGSFTQP LYRGELNEHL GLLGPYIRAE VEDNIMVTFR NQASRPYSFY SSLISYEEDQ  960
RQGAEPRKNF VKPNETKTYF WKVQHHMAPT KDEFDCKAWA YFSDVDLEKD VHSGLIGPLL  1020
VCHTNTLNPA HGRQVTVQEF ALFFTIFDET KSWYFTENME RNCRAPCNIQ MEDPTFKENY  1080
RFHAINGYIM DTLPGLVMAQ DQRIRWYLLS MGSNENIHSI HFSGHVFTVR KKEEYKMALY  1140
NLYPGVFETV EMLPSKAGIW RVECLIGEHL HAGMSTLFLV YSNKCQTPLG MASGHIRDFQ  1200
ITASGQYGQW APKLARLHYS GSINAWSTKE PFSWIKVDLL APMIIHGIKT QGARQKFSSL  1260
YISQFIIMYS LDGKKWQTYR GNSTGTLMVF FGNVDSSGIK HNIFNPPIIA RYIRLHPTHY  1320
SIRSTLRMEL MGCDLNSCSM PLGMESKAIS DAQITASSYF TNMFATWSPS KARLHLQGRS  1380
NAWRPQVNNP KEWLQVDFQK TMKVTGVTTQ GVKSLLTSMY VKEFLISSSQ DGHQWTLFFQ  1440
NGKVKVFQGN QDSFTPVVNS LDPPLLTRYL RIHPQSWVHQ IALRMEVLGC EAQDLY      1496

SEQ ID NO: 53          moltype = AA  length = 1498
FEATURE                Location/Qualifiers
source                 1..1498
                       mol_type = protein
                       organism = synthetic construct
SEQUENCE: 53
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLSC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATN VSNNSNTSND SNVSNKTSNN  780
SNATNKTNNT NDSTNRTNQT NTSQQNFVTQ RSKREITRTT LQSDQEEIDY DDTISVEMKK  840
EDFDIYDEDE NQSPRSFQKK TRHYFIAAVE RLWDYGMSSS PHVLRNRAQS GSVPQFKKVV  900
FQEFTDGSFT QPLYRGELNE HLGLLGPYIR AEVEDNIMVT FRNQASRPYS FYSSLISYEE  960
DQRQGAEPRK NFVKPNETKT YFWKVQHHMA PTKDEFDCKA WAYFSDVDLE KDVHSGLIGP  1020
LLVCHTNTLN PAHGRQVTVQ EFALFFTIFD ETKSWYFTEN MERNCRAPCN IQMEDPTFKE  1080
NYRFHAINGY IMDTLPGLVM AQDQRIRWYL LSMGSNENIH SIHFSGHVFT VRKKEEYKMA  1140
LYNLYPGVFE TVEMLPSKAG IWRVECLIGE HLHAGMSTLF LVYSNKCQTP LGMASGHIRD  1200
FQITASGQYG QWAPKLARLH YSGSINAWST KEPFSWIKVD LLAPMIIHGI KTQGARQKFS  1260
SLYISQFIIM YSLDGKKWQT YRGNSTGTLM VFFGNVDSSG IKHNIFNPPI IARYIRLHPT  1320
HYSIRSTLRM ELMGCDLNSC SMPLGMESKA ISDAQITASS YFTNMFATWS PSKARLHLQG  1380
RSNAWRPQVN NPKEWLQVDF QKTMKVTGVT TQGVKSLLTS MYVKEFLISS SQDGHQWTLF  1440
FQNGKVKVFQ GNQDSFTPVV NSLDPPLLTR YLRIHPQSWV HQIALRMEVL GCEAQDLY    1498

SEQ ID NO: 54          moltype = DNA  length = 4497
FEATURE                Location/Qualifiers
source                 1..4497
                       mol_type = other DNA
                       organism = synthetic construct
SEQUENCE: 54
gccaccagga ggtactacct gggggctgtg gagctgagct gggactacat gcagtctgac  60
ctgggggagc tgcctgtgga tgctaggttc cccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag ggggctgagt atgatgacca gactagccag  360
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
```

```
catgtggatc tggtgaagga cctgaactct ggcctgattg gggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgagttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaattctag acaccctagc accagacaga aacagtttaa tgccactaat  2280
gtgtctaaca acagcaacac cagcaatgac agcaatgtgt ctaacaagac atctaacaac  2340
agcaacgcca caaacaagac caacaacaca aatgatagca caaaccggac caaccagacc  2400
aataccagcc agcagaactt cgtgacccag agaagtaaga gagagatcac caggactacc  2460
ctgcagtctg atcaggagga gattgactat gatgacacaa tctctgtgga gatgaagaag  2520
gaggattttg acatctatga tgaggatgag aaccagagcc ccagatcttt tcagaagaag  2580
accagacact acttcattgc tgctgtggag aggctgtggg actatggcat gagcagcagc  2640
cctcatgtgc tgaggaacag ggcccagtct ggctctgtgc cccagttcaa gaaggtggtg  2700
ttccaggagt ttactgatgg cagcttcacc cagcccctgt acagagggga gctgaatgag  2760
cacctgggcc tgctgggccc ttatatcagg gctgaggtgg aggataacat tatggtgact  2820
ttcaggaacc aggcctctag gccctacagc ttctatagca gcctgatctc ttatgaggag  2880
gatcagaggc agggggctga gcccagaaag aactttgtga agcctaatga gactaagacc  2940
tacttctgga aggtccagca ccacatggcc cccaccaagg atgagtttga ttgcaaggcc  3000
tgggcctatt tctctgatgt ggacctggag aaggatgtcc attctggcct gattggccct  3060
ctgctggtgt gccacactaa cactctgaat cctgcccatg gcaggcaggt gactgtccag  3120
gagtttgccc tgttcttcac tatctttgat gagaccaaga gctggtactt tactgagaac  3180
atggagagaa actgcagggc tccttgcaat atccagatgg aggaccccac cttcaaggag  3240
aactacaggt ttcatgccat caatgggtac atcatggaca ccctgcctgg cctggtgatg  3300
gctcaggacc agagaatcag atggtatctg ctgagcatgg gcagcaatga gaatatccac  3360
agcatccact tctctggaca tgtgttcact gtgaggaaga aggaggagta caagatggct  3420
ctgtataatc tgtaccctgg agtgtttgaa actgtggaga tgctgccttc taaggctggc  3480
atctggaggg tggagtgcct gattggggag cacctgcatg ctggcatgag caccctgttc  3540
ctggtgtaca gcaacaagtg tcagaccccc ctgggcatgg cctctggaca catcagggac  3600
ttccagatca cagcctctgg ccagtatggc cagtgggccc ccaagctggc caggctgcat  3660
tattctggca gcatcaatgc ctggtctacc aaggagccct ttagctggat caaggtggac  3720
ctgctggccc ccatgattat ccatggcatc aagacccagg gggccaggca gaagttctct  3780
agcctgtaca tcagccagtt catcatcatg tactctctgg atggcaagaa gtggcagacc  3840
tacaggggca acagcactgg cacactgatg gtgttctttg gcaatgtgga cagctctggc  3900
atcaagcaca acatcttcaa tccccccatt atcgctaggt atattaggct gcatcccacc  3960
cactacagca tcagatctac cctgagaatg gagctgatgg gctgtgacct gaactcttgc  4020
agcatgcccc tgggcatgga gtctaaggcc atctctgatg cccagattac tgccagcagc  4080
tacttcacca atatgtttgc cacctggagc ccttctaagg ccaggctgca tctgcagggg  4140
aggagcaatg cctggaggcc tcaggtgaac aaccctaagg agtggctgca ggtggatttc  4200
cagaagacca tgaaggtgac tggagtgacc acccagggag tcaagagcct gctgaccagc  4260
atgtatgtga aggagtttct gatcagctct agccaggatg gccaccagtg gactctgttc  4320
tttcagaatg ggaaggtgaa ggtgtttcag ggcaatcagg actctttcac cctgtggtg  4380
aacagcctgg accccccct gctgaccaga tacctgagaa tccaccccca gagctgggtg  4440
caccagatcg ccctgaggat ggaggtgctg ggctgtgagg ctcaggatct gtactga     4497
```

```
SEQ ID NO: 55          moltype = DNA  length = 5934
FEATURE                Location/Qualifiers
source                 1..5934
                       mol_type = other DNA
                       organism = synthetic construct
SEQUENCE: 55
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
```

-continued

```
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg gggagctgc ctgtggatgc taggttcccc cctagagtgc  1260
ccaagtcctt ccccttcaac acttctgtgg tgtacaagaa gaccctgttt gtggagttca  1320
ctgaccacct gtttaacatt gccaagccca ggcccccttg gatgggcctg ctggggccca  1380
ccatccaggc tgaggtgtat gacactgtgg tgatcaccct gaagaacatg gccagccatc  1440
ctgtgagcct gcatgctgtg ggggtgagct actggaaggc cagcgagggg gctgagtatg  1500
atgaccagac tagccagagg gagaaggagg atgacaaggt gtttcctgga ggcagccaca  1560
cctatgtgtg gcaggtgctg aaggagaatg gccccatggc ctctgacccc ctgtgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaacccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gagttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga attctagaca ccctagcacc agacagaaac  3420
agtttaatgc cactaatgtg tctaacaaca gcaacaccag caatgacagc aatgtgtcta  3480
acaagacatc taacaacagc aacgccacaa acaagaccaa caacacaaat gatagcacaa  3540
accggaccaa ccagaccaat accagccagc agaacttcgt gacccagaga agtaagagag  3600
agatcaccag gactaccctg cagtctgatc aggaggagat tgactatgat gacacaatct  3660
ctgtggagat gaagaaggag gattttgaca tctatgatga ggatgagaac cagagcccca  3720
gatcttttca gaagaagacc agacactact tcattgctgc tgtggagagg ctgtgggact  3780
atggcatgag cagcagccct catgtgctga ggaacagggc ccagtctggc tctgtgcccc  3840
agttcaagaa ggtggtgttc caggagttta ctgatggcag cttcacccag cccctgtaca  3900
gaggggagct gaatgagcac ctgggcctgc tgggccctta tatcagggct gaggtggagg  3960
ataacattat ggtgactttc aggaaccagg cctctaggcc ctacagcttc tatagcagcc  4020
tgatctctta tgaggaggat cagaggcagg gggctgagcc cagaaagaac tttgtgaagc  4080
ctaatgagac taagacctac ttctggaagg tccagcacca catggccccc accaaggatg  4140
agtttgattg caaggcctgg gcctatttct ctgatgtgga cctggagaag gatgtccatt  4200
ctggcctgat tggccctctg ctggtgtgcc acactaacac tctgaatcct gcccatggca  4260
ggcaggtgac tgtccaggag tttgccctgt tcttcactat ctttgatgag accaagagct  4320
ggtactttac tgagaacatg gagagaaact gcagggctcc ttgcaatatc cagatggagg  4380
accccacctt caaggagaac tacaggtttc atgccatcaa tgggtacatc atggacaccc  4440
tgcctggcct ggtgatggct caggaccaga gaatcagatg gtatctgctg agcatgggca  4500
gcaatgagaa tatccacagc atccacttct ctggacatgt gttcactgtg aggaagaagg  4560
aggagtacaa gatggctctg tataatctgt accctggagt gtttgaaact gtggagatgc  4620
tgccttctaa ggctggcatc tggagggtgg agtgcctgat tggggagcac ctgcatgctg  4680
gcatgagcac cctgttcctg gtgtacagca acaagtgtca gacccccctg ggcatggcct  4740
ctggacacat cagggacttc cagatcacag cctctggcca gtatggccag tgggccccca  4800
agctggccag gctgcattat tctggcagca tcaatgcctg gtctaccaag gagcccttta  4860
gctggatcaa ggtggacctg ctggccccca tgattatcca tggcatcaag acccaggggg  4920
ccaggcagaa gttctctagc ctgtacatca gccagttcat catcatgtac tctctggatg  4980
gcaagaagtg gcagacctac aggggcaaca gcactggcac actgatggtg ttctttggca  5040
```

```
atgtggacag ctctggcatc aagcacaaca tcttcaatcc ccccattatc gctaggtata  5100
ttaggctgca tcccacccac tacagcatca gatctaccct gagaatggag ctgatgggct  5160
gtgacctgaa ctcttgcagc atgcccctgg gcatggagtc taaggccatc tctgatgccc  5220
agattactgc cagcagctac ttcaccaata tgtttgccac ctggagccct tctaaggcca  5280
ggctgcatct gcaggggagg agcaatgcct ggaggcctca ggtgaacaac cctaaggagt  5340
ggctgcaggt ggatttccag aagaccatga aggtgactgg agtgaccacc cagggagtca  5400
agagcctgct gaccagcatg tatgtgaagg agtttctgat cagctctagc caggatggcc  5460
accagtggac tctgttcttt cagaatggga aggtgaaggt gtttcagggc aatcaggact  5520
ctttcacccc tgtggtgaac agcctggacc ccccccctgct gaccagatac ctgagaatcc  5580
acccccagag ctgggtgcac cagatcgccc tgaggatgga ggtgctgggc tgtgaggctc  5640
aggatctgta ctgagatatc tctagagtcg acagtactgg tgatcagcct cgactgtgcc  5700
ttctagttgc cagccatctg ttgtttgccc ctcccccgtg ccttccttga ccctggaagg  5760
tgccactccc actgtccttt cctaataaaa tgaggaaatt gcatcgcatt gtctgagtag  5820
gtgtcattct attctggggg gtggggtggg gcaggacagc aagggggagg attgggaaga  5880
caatagcagg catgctgggg atgcggtggg ctctatggaa ccagctgggg cccg        5934

SEQ ID NO: 56           moltype = DNA  length = 4491
FEATURE                 Location/Qualifiers
source                  1..4491
                        mol_type = other DNA
                        organism = synthetic construct
SEQUENCE: 56
gccaccagga ggtactacct ggggggctgtg gagctgagct gggactacat gcagtctgac  60
ctgggggagc tgcctgtgga tgctaggttc ccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag gggggctgagt atgatgacca gactagccag  360
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg ggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgttttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatagcag acaccctagc accagacaga aacagtttaa tgccactaat  2280
gtgagcaaca acagcaacac cagcaatgac agcaatgtgt ctaacaagac atctaacaac  2340
agcaatgcca caaacaagac caacaacaca aatgatagca caaacaggac caaccagacc  2400
aataccagcc cccctgtgct gaagcaccat cagagggaga tcaccaggac taccctgcag  2460
tctgatcagg aggagattga ctatgatgac acaatctctg tggagatgaa gaaggaggat  2520
tttgacatct atgatgagga tgagaaccag agccccagat cttttcagaa gaagaccaga  2580
cactacttca ttgctgctgt ggagaggctg tgggactatg gcatgagcag cagccctcat  2640
gtgctgagga acagggccca gtctggctct gtgccccagt tcaagaaggt ggtgttccag  2700
gagtttactg atggcagctt cacccagccc ctgtacagag gggagctgaa tgagcacctg  2760
ggcctgctgg gcccttatat cagggctgag gtggaggata acattatggt gactttcagg  2820
aaccaggcct ctaggcccta cagcttctat agcagcctga tctcttatga ggaggatcag  2880
aggcaggggg ctgagcccag aaagaacttt gtgaagccta atgagactaa gacctacttc  2940
tggaaggtcc agcaccacat ggcccccacc aaggatgagt ttgattgcaa ggcctgggcc  3000
tatttctctg atgtggacct ggagaaggat gtccattctg gcctgattgg ccctctgctg  3060
gtgtgccaca ctaacactct gaatcctgcc catggcaggc aggtgactgt ccaggagttt  3120
gccctgttct tcactatctt tgatgagacc aagagctggt actttactga gaacatggag  3180
agaaactgca gggctccttg caatatccag atggaggacc ccaccttcaa ggagaactac  3240
aggtttcatg ccatcaatgg gtacatcatg gacaccctgc ctggcctggt gatggctcag  3300
gaccagagaa tcagatggta tctgctgagc atgggcagca atgagaatat ccacagcatc  3360
cacttctctg gacatgtgtt cactgtgagg aagaaggagg agtacaagat ggctctgtat  3420
```

```
aatctgtacc ctggagtgtt tgaaactgtg gagatgctgc cttctaaggc tggcatctgg  3480
agggtggagt gcctgattgg ggagcacctg catgctggca tgagcaccct gttcctggtg  3540
tacagcaaca agtgtcagac cccctgggc atggcctctg gacacatcag ggacttccag  3600
atcacagcct ctggccagta tggccagtgg gcccccaagc tggccaggct gcattattct  3660
ggcagcatca atgcctggtc taccaaggag ccctttagct ggatcaaggt ggacctgctg  3720
gcccccatga ttatccatgg catcaagacc caggggcca ggcagaagtt ctctagcctg  3780
tacatcagcc agttcatcat catgtactct ctggatggca agaagtggca gacctacagg  3840
ggcaacagca ctggcacact gatggtgttc tttggcaatg tggacagctc tggcatcaag  3900
cacaacatct tcaatcccc cattatcgct aggtatatta ggctgcatcc cacccactac  3960
agcatcagat ctaccctgag aatggagctg atgggctgtg acctgaactc ttgcagcatg  4020
cccctgggca tggagtctaa ggccatctct gatgcccaga ttactgccag cagctacttc  4080
accaatatgt ttgccacctg gagcccttct aaggccaggc tgcatctgca ggggaggagc  4140
aatgcctgga ggcctcaggt gaacaaccct aaggagtggc tgcaggtgga tttccagaag  4200
accatgaagg tgactggagt gaccacccag ggagtcaaga gcctgctgac cagcatgtat  4260
gtgaaggagt ttctgatcag ctctagccag gatggccacc agtggactct gttctttcag  4320
aatgggaagg tgaaggtgtt tcagggcaat caggactctt tcacccctgt ggtgaacagc  4380
ctggaccccc ccctgctgac cagatacctg agaatccacc cccagagctg ggtgcaccag  4440
atcgccctga ggatggaggt gctgggctgt gaggctcagg atctgtactg a            4491

SEQ ID NO: 57          moltype = DNA  length = 5928
FEATURE                Location/Qualifiers
source                 1..5928
                       mol_type = other DNA
                       organism = synthetic construct
SEQUENCE: 57
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gcccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg ggggagctgc ctgtggatgc taggttcccc cctagagtgc  1260
ccaagtcctt ccccttcaac acttctgtgg tgtacaagaa gaccctgttt gtggagttca  1320
ctgaccacct gtttaacatt gccaagccca ggcccccttg gatgggcctg ctggggccca  1380
ccatccaggc tgaggtgtat gacactgtgg tgatcaccct gaagaacatg gccagccatc  1440
ctgtgagcct gcatgctgtg ggggtgagct actggaaggc cagcgagggg gctgagtatg  1500
atgaccagac tagccagagg gagaaggagg atgacaaggt gtttcctgga ggcagccaca  1560
cctatgtgtg gcaggtgctg aaggagaatg gccccatggc ctctgacccc ctgtgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaaccccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gttttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
```

```
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga atagcagaca ccctagcacc agacagaaac  3420
agtttaatgc cactaatgtg agcaacaaca gcaacaccag caatgacagc aatgtgtcta  3480
acaagacatc taacaacagc aatgccacaa acaagaccaa caacacaaat gatagcacaa  3540
acaggaccaa ccagaccaat accagccccc ctgtgctgaa gcaccatcag agggagatca  3600
ccaggactac cctgcagtct gatcaggagg agattgacta tgatgacaca atctctgtgg  3660
agatgaagaa ggaggatttt gacatctatg atgaggatga gaaccagagc cccagatctt  3720
ttcagaagaa gaccagacac tacttcattg ctgctgtgga gaggctgtgg gactatggca  3780
tgagcagcag ccctcatgtg ctgaggaaca gggcccagtc tggctctgtg ccccagttca  3840
agaaggtggt gttccaggag tttactgatg gcagcttcac ccagcccctg tacagagggg  3900
agctgaatga gcacctgggc ctgctgggcc cttatatcag ggctgaggtg gaggataaca  3960
ttatggtgac tttcaggaac caggcctcta ggccctacag cttctatagc agcctgatct  4020
cttatgagga ggatcagagg caggggggctg agcccagaaa gaactttgtg aagcctaatg  4080
agactaagac ctacttctgg aaggtccagc accacatggc cccccaccaag gatgagtttg  4140
attgcaaggc ctgggcctat ttctctgatg tggacctgga gaaggatgtc cattctggcc  4200
tgattggccc tctgctggtg tgccacacta acactctgaa tcctgcccat ggcaggcagg  4260
tgactgtcca ggagtttgcc ctgttcttca ctatctttga tgagaccaag agctggtact  4320
ttactgagaa catggagaga aactgcaggg ctccttgcaa tatccagatg gaggacccca  4380
ccttcaagga gaactacagg tttcatgcca tcaatgggta catcatggac accctgcctg  4440
gcctggtgat ggctcaggac cagagaatca gatggtatct gctgagcatg ggcagcaatg  4500
agaatatcca cagcatccac ttctctggac atgtgttcac tgtgaggaag aaggaggagt  4560
acaagatggc tctgtataat ctgtaccctg gagtgtttga aactgtggag atgctgcctt  4620
ctaaggctgg catctggagg gtggagtgcc tgattgggga gcacctgcat gctggcatga  4680
gcaccctgtt cctggtgtac agcaacaagt gtcagacccc cctgggcatg gcctctggac  4740
acatcaggga cttccagatc acagcctctg gccagtatgg ccagtgggcc cccaagctgg  4800
ccaggctgca ttattctggc agcatcaatg cctggtctac caaggagccc tttagctgga  4860
tcaaggtgga cctgctggcc cccatgatta tccatggcat caagacccag gggggccaggc  4920
agaagttctc tagcctgtac atcagccagt tcatcatcat gtactctctg gatggcaaga  4980
agtggcagac ctacaggggc aacagcactg gcacactgat ggtgttcttt ggcaatgtgg  5040
acagctctgg catcaagcac aacatcttca atcccccccat tatcgctagg tatattaggc  5100
tgcatcccac ccactacagc atcagatcta ccctgagaat ggagctgatg ggctgtgacc  5160
tgaactcttg cagcatgccc ctgggcatgg agtctaaggc catctctgat gcccagatta  5220
ctgccagcag ctacttcacc aatatgtttg ccacctggag cccttctaag gccaggctgc  5280
atctgcaggg gaggagcaat gcctggaggc ctcaggtgaa caaccctaag gagtggctgc  5340
aggtggattt ccagaagacc atgaaggtga ctggagtgac cacccaggga gtcaagagcc  5400
tgctgaccag catgtatgtg aaggagtttc tgatcagctc tagccaggat ggccaccagt  5460
ggactctgtt ctttcagaat gggaaggtga aggtgtttca gggcaatcag gactctttca  5520
cccctgtggt gaacagcctg gacccccccc tgctgaccag atacctgaga atccaccccc  5580
agagctgggt gcaccagatc gccctgagga tggaggtgct gggctgtgag gctcaggatc  5640
tgtactgaga tatctctaga gtcgacagta ctggtgatca gcctcgactg tgccttctag  5700
ttgccagcca tctgttgttt gcccctcccc cgtgccttcc ttgaccctgg aaggtgccac  5760
tcccactgtc ctttcctaat aaaatgagga aattgcatcg cattgtctga gtaggtgtca  5820
ttctattctg gggggtgggg tggggcagga cagcaagggg gaggattggg aagacaatag  5880
caggcatgct ggggatgcgg tgggctctat ggaaccagct ggggcccg              5928
```

```
SEQ ID NO: 58          moltype = DNA  length = 4491
FEATURE                Location/Qualifiers
source                 1..4491
                       mol_type = other DNA
                       organism = synthetic construct
SEQUENCE: 58
gccaccagga ggtactacct gggggctgtg gagctgagct gggactacat gcagtctgac  60
ctgggggagc tgcctgtgga tgctaggttc cccccctagag tgcccaagtc cttcccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag ggggctgagt atgatgacca gactagccag  360
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg gggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgagttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
```

```
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatagcag acaccctagc accagacaga aacagtttaa tgccactaat  2280
gtgagcaaca acagcaacac cagcaatgac agcaatgtgt ctaacaagac atctaacaac  2340
agcaatgcca caaacaagac caacaacaca aatgatagca caaacaggac caaccagacc  2400
aataccagcc cccctgtgct gaagcaccat cagagggaga tcaccaggac taccctgcag  2460
tctgatcagg aggagattga ctatgatgac acaatctctg tggagatgaa gaaggaggat  2520
tttgacatct atgatgagga tgagaaccag agccccagat cttttcagaa gaagaccaga  2580
cactacttca ttgctgctgt ggagaggctg tgggactatg gcatgagcag cagccctcat  2640
gtgctgagga acagggccca gtctggctct gtgccccagt tcaagaaggt ggtgttccag  2700
gagtttactg atggcagctt cacccagccc ctgtacagag gggagctgaa tgagcacctg  2760
ggcctgctgg gcccttatat cagggctgag gtggaggata acattatggt gactttcagg  2820
aaccaggcct ctaggcccta cagcttctat agcagcctga tctcttatga ggaggatcag  2880
aggcaggggg ctgagcccag aaagaacttt gtgaagccta atgagactaa gacctacttc  2940
tggaaggtcc agcaccacat ggcccccacc aaggatgagt ttgattgcaa ggcctgggcc  3000
tatttctctg atgtggacct ggagaaggat gtccattctg gcctgattgg ccctctgctg  3060
gtgtgccaca ctaacactct gaatcctgcc catggcaggc aggtgactgt ccaggagttt  3120
gccctgttct tcactatctt tgatgagacc aagagctggt actttactga gaacatggag  3180
agaaactgca gggctccttg caatatccag atggaggacc ccaccttcaa ggagaactac  3240
aggtttcatg ccatcaatgg gtacatcatg gacaccctgc ctggcctggt gatggctcag  3300
gaccagagaa tcagatggta tctgctgagc atgggcagca atgagaatat ccacagcatc  3360
cacttctctg gacatgtgtt cactgtgagg aagaaggagg agtacaagat ggctctgtat  3420
aatctgtacc ctggagtgtt tgaaactgtg gagatgctgc cttctaaggc tggcatctgg  3480
agggtggagt gcctgattgg ggagcacctg catgctggca tgagcaccct gttcctggtg  3540
tacagcaaca agtgtcagac ccccctgggc atggcctctg gacacatcag ggacttccag  3600
atcacagcct ctggccagta tggccagtgg gcccccaagc tggccaggct gcattattct  3660
ggcagcatca atgcctggtc taccaaggag ccctttagct ggatcaaggt ggacctgctg  3720
gcccccatga ttatccatgg catcaagacc caggggggcca ggcagaagtt ctctagcctg  3780
tacatcagcc agttcatcat catgtactct ctggatggca agaagtggca gacctacagg  3840
ggcaacagca ctggcacact gatggtgttc tttggcaatg tggacagctc tggcatcaag  3900
cacaacatct tcaatccccc cattatcgct aggtatatta ggctgcatcc cacccactac  3960
agcatcagat ctaccctgag aatggagctg atgggctgtg acctgaactc ttgcagcatg  4020
cccctgggca tggagtctaa ggccatctct gatgcccaga ttactgccag cagctacttc  4080
accaatatgt ttgccacctg gagcccttct aaggccaggc tgcatctgca ggggaggagc  4140
aatgcctgga ggcctcaggt gaacaaccct aaggagtggc tgcaggtgga tttccagaag  4200
accatgaagg tgactggagt gaccacccag ggagtcaaga gcctgctgac cagcatgtat  4260
gtgaaggagt ttctgatcag ctctagccag gatggccacc agtggactct gttctttcag  4320
aatgggaagg tgaaggtgtt tcagggcaat caggactctt tcacccctgt ggtgaacagc  4380
ctggaccccc ccctgctgac cagatacctg agaatccacc cccagagctg ggtgcaccag  4440
atcgccctga ggatggaggt gctgggctgt gaggctcagg atctgtactg a            4491
```

```
SEQ ID NO: 59           moltype = DNA  length = 5928
FEATURE                 Location/Qualifiers
source                  1..5928
                        mol_type = other DNA
                        organism = synthetic construct
SEQUENCE: 59
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg ggggagctgc ctgtggatgc taggttcccc cctagagtgc  1260
ccaagtcctt ccccttcaac acttctgtgg tgtacaagaa gaccctgttt gtggagttca  1320
ctgaccacct gtttaacatt gccaagccca ggccccccttg gatgggcctg ctggggccca  1380
ccatccaggc tgaggtgtat gacactgtgg tgatcaccct gaagaacatg gccagccatc  1440
```

```
ctgtgagcct gcatgctgtg ggggtgagct actggaaggc cagcgagggg gctgagtatg  1500
atgaccagac tagccagagg gagaaggagg atgacaaggt gtttcctgga ggcagccaca  1560
cctatgtgtg gcaggtgctg aaggagaatg gccccatggc ctctgacccc ctgtgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaacccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gagttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga atagcagaca ccctagcacc agacagaaac  3420
agtttaatgc cactaatgtg agcaacaaca gcaacaccag caatgacagc aatgtgtcta  3480
acaagacatc taacaacagc aatgccacaa acaagaccaa caacacaaat gatagcacaa  3540
acaggaccaa ccagaccaat accagccccc ctgtgctgaa gcaccatcag agggagatca  3600
ccaggactac cctgcagtct gatcaggagg agattgacta tgatgacaca atctctgtgg  3660
agatgaagaa ggaggatttt gacatctatg atgaggatga gaaccagagc cccagatctt  3720
ttcagaagaa gaccagacac tacttcattg ctgctgtgga gaggctgtgg gactatggca  3780
tgagcagcag ccctcatgtg ctgaggaaca gggcccagtc tggctctgtg ccccagttca  3840
agaaggtggt gttccaggag tttactgatg gcagcttcac ccagcccctg tacagagggg  3900
agctgaatga gcacctgggc ctgctgggcc cttatatcag ggctgaggtg gaggataaca  3960
ttatggtgac tttcaggaac caggcctcta ggccctacag cttctatagc agcctgatct  4020
cttatgagga ggatcagagg caggggctg agcccagaaa gaactttgtg aagcctaatg  4080
agactaagac ctacttctgg aaggtccagc accacatggc cccccaccaag gatgagtttg  4140
attgcaaggc ctgggcctat ttctctgatg tggacctgga gaaggatgtc cattctggcc  4200
tgattggccc tctgctggtg tgccacacta acactctgaa tcctgcccat ggcaggcagg  4260
tgactgtcca ggagtttgcc ctgttcttca ctatctttga tgagaccaag agctggtact  4320
ttactgagaa catggagaga aactgcaggg ctccttgcaa tatccagatg gaggacccca  4380
ccttcaagga gaactacagg tttcatgcca tcaatgggta catcatggac accctgcctg  4440
gcctggtgat ggctcaggac cagagaatca gatggtatct gctgagcatg ggcagcaatg  4500
agaatatcca cagcatccac ttctctggac atgtgttcac tgtgaggaag aaggaggagt  4560
acaagatggc tctgtataat ctgtaccctg gagtgtttga aactgtggag atgctgcctt  4620
ctaaggctgg catctggagg gtggagtgcc tgattgggga gcacctgcat gctggcatga  4680
gcaccctgtt cctggtgtac agcaacaagt gtcagacccc cctgggcatg gcctctggac  4740
acatcaggga cttccagatc acagcctctg gccagtatgg ccagtgggcc cccaagctgg  4800
ccaggctgca ttattctggc agcatcaatg cctggtctac caaggagccc tttagctgga  4860
tcaaggtgga cctgctggcc cccatgatta tccatggcat caagacccag gggccaggc  4920
agaagttctc tagcctgtac atcagccagt tcatcatcat gtactctctg gatggcaaga  4980
agtggcagac ctacaggggc aacagcactg gcacactgat ggtgttcttt ggcaatgtgg  5040
acagctctgg catcaagcac aacatcttca atccccccat tatcgctagg tatattaggc  5100
tgcatcccac ccactacagc atcagatcta ccctgagaat ggagctgatg ggctgtgacc  5160
tgaactcttg cagcatgccc ctgggcatgg agtctaaggc catctctgat gcccagatta  5220
ctgccagcag ctacttcacc aatatgtttg ccacctggag cccttctaag gccaggctgc  5280
atctgcaggg gaggagcaat gcctggaggc ctcaggtgaa caaccctaag gagtggctgc  5340
aggtggattt ccagaagacc atgaaggtga ctggagtgac cacccaggga gtcaagagcc  5400
tgctgaccag catgtatgtg aaggagtttc tgatcagctc tagccaggat ggccaccagt  5460
ggactctgtt ctttcagaat gggaaggtga aggtgtttca gggcaatcag gactctttca  5520
cccctgtggt gaacagcctg gacccccccc tgctgaccag atacctgaga atccaccccc  5580
agagctgggt gcaccagatc gccctgagga tggaggtgct gggctgtgag gctcaggatc  5640
tgtactgaga tatctctaga gtcgacagta ctggtgatca gcctcgactg tgccttctag  5700
ttgccagcca tctgttgttt gcccctcccc cgtgccttcc ttgaccctgg aaggtgccac  5760
tcccactgtc ctttcctaat aaaatgagga aattgcatcg cattgtctga gtaggtgtca  5820
ttctattctg gggggtgggg tggggcagga cagcaagggg gaggattggg aagacaatag  5880
caggcatgct ggggatgcgg tgggctctat ggaaccagct ggggcccg                5928
```

SEQ ID NO: 60 moltype = DNA length = 4491
FEATURE Location/Qualifiers
source 1..4491

```
                       mol_type = other DNA
                       organism = synthetic construct
SEQUENCE: 60
gccaccagga ggtactacct gggggctgtg gagctgagct gggactacat gcagtctgac  60
ctgggggagc tgcctgtgga tgctaggttc cccccctagag tgcccaagtc cttccccttc  120
aacacttctg tggtgtacaa gaagaccctg tttgtggagt tcactgacca cctgtttaac  180
attgccaagc ccaggccccc ttggatgggc ctgctggggc ccaccatcca ggctgaggtg  240
tatgacactg tggtgatcac cctgaagaac atggccagcc atcctgtgag cctgcatgct  300
gtgggggtga gctactggaa ggccagcgag gggctgagt atgatgacca gactagccag  360
agggagaagg aggatgacaa ggtgtttcct ggaggcagcc acacctatgt gtggcaggtg  420
ctgaaggaga atggccccat ggcctctgac cccctgtgcc tgacctacag ctacctgagc  480
catgtggatc tggtgaagga cctgaactct ggcctgattg ggctctgct ggtgtgtaga  540
gagggcagcc tggctaagga gaagacccag accctgcata agttcatcct gctgtttgct  600
gtgtttgatg agggcaagag ctggcactct gagaccaaga acagcctgat gcaggatagg  660
gatgctgcct ctgccagggc ttggcccaag atgcacactg tgaatggcta tgtgaatagg  720
agcctgcctg gcctgattgg ctgccacagg aagtctgtgt actggcatgt gattggaatg  780
ggcacaaccc ctgaggtcca tagcatcttc ctggagggcc acactttcct ggtgaggaac  840
cacagacagg cctctctgga gattagcccc atcaccttcc tgactgctca gactctgctg  900
atggacctgg gccagttcct gctgagttgc catattagct ctcaccagca tgatggcatg  960
gaggcctatg tgaaggtgga cagctgccct gaggagcctc agctgaggat gaagaacaat  1020
gaggaggctg aagactatga tgatgacctg actgattctg agatggatgt ggtgaggttt  1080
gatgatgaca atagccccag cttcattcag atcagatctg tggccaaaaa gcaccccaag  1140
acctgggtgc attacattgc tgctgaagag gaggactggg actatgcccc tctggtgctg  1200
gcccctgatg ataggagcta taagagccag tacctgaaca atgggcccca gaggattggc  1260
agaaagtaca agaaggtgag gttcatggct tacactgatg aaaccttcaa aaccagggag  1320
gccatccagc atgagtctgg catcctgggc cctctgctgt atggagaggt gggagacacc  1380
ctgctgatca tcttcaagaa ccaggccagc aggccctaca acatctatcc tcatggcatc  1440
actgatgtga gacctctgta cagcaggagg ctgcctaagg gggtgaaaca cctgaaggac  1500
tttcccatcc tgcctgggga gatcttcaag tataagtgga ctgtgactgt ggaggatggc  1560
cctaccaagt ctgaccccag gtgtctgaca aggtattaca gcagctttgt gaacatggag  1620
agggacctgg cctctggcct gattggccct ctgctgatct gctacaagga gtctgtggac  1680
cagaggggca accagatcat gtctgacaag aggaatgtga tcctgttctc tgtgtttgat  1740
gagaatagga gctggtatct gactgagaac atccagagat tcctgcccaa tcctgctggg  1800
gtgcagctgg aggaccctga gtttcaggcc agcaatatca tgcacagcat caatggctat  1860
gtgtttgaca gcctgcagct gtctgtgtgc ctgcatgagg tggcctactg gtacatcctg  1920
agcattggag cccagactga ttttctgtct gtgttctttt ctggctatac cttcaagcac  1980
aagatggtgt atgaggacac cctgaccctg ttccccttct ctggggagac tgtgttcatg  2040
tctatggaga atcctgggct gtggattctg ggctgccaca actctgattt caggaacagg  2100
ggcatgactg ccctgctgaa ggtgagcagc tgtgacaaga acactgggga ctactatgag  2160
gatagctatg aggacatttc tgcttatctg ctgtctaaga ataatgccat tgagcccagg  2220
agcttcagcc agaatagcag acaccctagc accagacaga aacagtttaa tgccactaat  2280
gtgagcaaca acagcaacac cagcaatgac agcaatgtgt ctaacaagac atctaacaac  2340
agcaatgcca caaacaagac caacaacaca aatgatagca caaacaggac caaccagacc  2400
aataccagcc cccctgtgct gaagagacat cagagggaga tcaccaggac taccctgcag  2460
tctgatcagg aggagattga ctatgatgac acaatctctg tggagatgaa gaaggaggat  2520
tttgacatct atgatgagga tgagaaccag agccccagat cttttcagaa gaagaccaga  2580
cactacttca ttgctgctgt ggagaggctg tgggactatg gcatgagcag cagccctcat  2640
gtgctgagga acagggccca gtctggctct gtgccccagt tcaagaaggt ggtgttccag  2700
gagtttactg atggcagctt cacccagccc ctgtacagag gggagctgaa tgagcacctg  2760
ggcctgctgg gcccttatat cagggctgag gtggaggata acattatggt gactttcagg  2820
aaccaggcct ctaggcccta cagcttctat agcagcctga tctcttatga ggaggatcag  2880
aggcaggggg ctgagcccag aaagaacttt gtgaagccta atgagactaa gacctacttc  2940
tggaaggtcc agcaccacat ggcccccacc aaggatgagt ttgattgcaa ggcctgggcc  3000
tatttctctg atgtggacct ggagaaggat gtccattctg gcctgattgg ccctctgctg  3060
gtgtgccaca ctaacactct gaatcctgcc catggcaggc aggtgactgt ccaggagttt  3120
gccctgttct tcactatctt tgatgagacc aagagctggt actttactga gaacatggag  3180
agaaactgca gggctccttg caatatccag atggaggacc ccaccttcaa ggagaactac  3240
aggtttcatg ccatcaatgg gtacatcatg gacaccctgc ctggcctggt gatggctcag  3300
gaccagagaa tcagatggta tctgctgagc atgggcagca atgagaatat ccacagcatc  3360
cacttctctg gacatgtgtt cactgtgagg aagaaggagg agtacaagat ggctctgtat  3420
aatctgtacc ctggagtgtt tgaaactgtg gagatgctgc cttctaaggc tggcatctgg  3480
agggtggagt gcctgattgg ggagcacctg catgctggca tgagcaccct gttcctggtg  3540
tacagcaaca agtgtcagac ccccctgggc atggcctctg gacacatcag ggacttccag  3600
atcacagcct ctggccagta tggccagtgg gcccccaagc tggccaggct gcattattct  3660
ggcagcatca atgcctggtc taccaaggag ccctttagct ggatcaaggt ggacctgctg  3720
gcccccatga ttatccatgg catcaagacc caggggccca ggcagaagtt ctctagcctg  3780
tacatcagcc agttcatcat catgtactct ctggatggca agaagtggca gacctacagg  3840
ggcaacagca ctggcacact gatggtgttc tttggcaatg tggacagctc tggcatcaag  3900
cacaacatct tcaatccccc cattatcgct aggtatatta ggctgcatcc cacccactac  3960
agcatcagat ctaccctgag aatggagctg atgggctgtg acctgaactc ttgcagcatg  4020
cccctgggca tggagtctaa ggccatctct gatgcccaga ttactgccag cagctacttc  4080
accaatatgt ttgccacctg gagcccttct aaggccaggc tgcatctgca ggggaggagc  4140
aatgcctgga ggcctcaggt gaacaaccct aaggagtggc tgcaggtgga tttccagaag  4200
accatgaagg tgactggagt gaccacccag ggagtcaaga gcctgctgac cagcatgtat  4260
gtgaaggagt ttctgatcag ctctagccag gatggccacc agtggactct gttctttcag  4320
aatgggaagg tgaaggtgtt tcagggcaat caggactctt tcacccctgt ggtgaacagc  4380
ctggaccccc ccctgctgac cagatacctg agaatccacc cccagagctg ggtgcaccag  4440
atcgccctga ggatggaggt gctgggctgt gaggctcagg atctgtactg a           4491
```

```
SEQ ID NO: 61          moltype = DNA  length = 5928
FEATURE                Location/Qualifiers
source                 1..5928
                       mol_type = other DNA
                       organism = synthetic construct
SEQUENCE: 61
ccccaactgg ggtaaccttt gggctccccg ggcgcgacta gtgaattcgt caatattggc  60
cattagccat attattcatt ggttatatag cataaatcaa tattggctat tggccattgc  120
atacgttgta tctatatcat aatatgtaca tttatattgg ctcatgtcca atatgaccgc  180
catgttggtg tggaaagtcc ccaggctccc cagcaggcag aagtatgcaa agcatgcatc  240
tcaattagtc agcaaccagg cattgattat tgactagtta ttaatagtaa tcaattacgg  300
ggtcattagt tcatagccca tatatggagt tccgcgttac ataacttacg gtaaatggcc  360
cgcctggctg accgcccaac gacccccgcc cattgacgtc aataatgacg tatgttccca  420
tagtaacgcc aatagggact ttccattgac gtcaatgggt ggagtattta cggtaaactg  480
cccacttggc agtacatcaa gtgtatcata tgccaagtcc gccccctatt gacgtcaatg  540
acggtaaatg gcccgcctgg cattatgccc agtacatgac cttacgggac tttcctactt  600
ggcagtacat ctacgtatta gtcatcgcta ttaccatggt gatgcggttt tggcagtaca  660
ccaatgggcg tggatagcgg tttgactcac ggggatttcc aagtctccac cccattgacg  720
tcaatgggag tttgttttgg caccaaaatc aacgggactt tccaaaatgt cgtaataacc  780
ccgccccgtt gacgcaaatg ggcggtaggc gtgtacggtg ggaggtctat ataagcagag  840
gtcgtttagt gaaccgtcag atcactagta gctttattgc ggtagtttat cacagttaaa  900
ttgctaacgc agtcagtgct cgactgatca caggtaagta tcaaggttac aagacaggtt  960
taaggaggcc aatagaaact gggcttgtcg agacagagaa gattcttgcg tttctgatag  1020
gcacctattg gtcttactga catccacttt gcctttctct ccacaggggt accgaagccg  1080
ctagcgctac cggtgccacc atgcagattg aactgagcac ctgcttcttc ctgtgtctgc  1140
tgagattctg cttctctgcc accaggaggt actacctggg ggctgtggag ctgagctggg  1200
actacatgca gtctgacctg ggggagctgc ctgtggatgc taggttcccc cctagagtgc  1260
ccaagtcctt cccctttcaac acttctgtgg tgtacaagaa gaccctgttt gtggagttca  1320
ctgaccacct gtttaacatt gccaagccca ggcccccttg gatgggcctg ctggggccca  1380
ccatccaggc tgaggtgtat gacactgtgg tgatcaccct gaagaacatg gccagccatc  1440
ctgtgagcct gcatgctgtg ggggtgagct actggaaggc cagcgagggg gctgagtatg  1500
atgaccagac tagccagagg gagaaggagg atgacaaggt gtttcctgga ggcagccaca  1560
cctatgtgtg gcaggtgctg aaggagaatg gccccatggc ctctgacccc ctgtgcctga  1620
cctacagcta cctgagccat gtggatctgg tgaaggacct gaactctggc ctgattgggg  1680
ctctgctggt gtgtagagag ggcagcctgg ctaaggagaa gacccagacc ctgcataagt  1740
tcatcctgct gtttgctgtg tttgatgagg gcaagagctg gcactctgag accaagaaca  1800
gcctgatgca ggatagggat gctgcctctg ccagggcttg gcccaagatg cacactgtga  1860
atggctatgt gaataggagc ctgcctggcc tgattggctg ccacaggaag tctgtgtact  1920
ggcatgtgat tggaatgggc acaacccctg aggtccatag catcttcctg gagggccaca  1980
ctttcctggt gaggaaccac agacaggcct ctctggagat tagccccatc accttcctga  2040
ctgctcagac tctgctgatg gacctgggcc agttcctgct gagttgccat attagctctc  2100
accagcatga tggcatggag gcctatgtga aggtggacag ctgccctgag gagcctcagc  2160
tgaggatgaa gaacaatgag gaggctgaag actatgatga tgacctgact gattctgaga  2220
tggatgtggt gaggtttgat gatgacaata gccccagctt cattcagatc agatctgtgg  2280
ccaaaaagca ccccaagacc tgggtgcatt acattgctgc tgaagaggag gactgggact  2340
atgcccctct ggtgctggcc cctgatgata ggagctataa gagccagtac ctgaacaatg  2400
ggccccagag gattggcaga aagtacaaga aggtgaggtt catggcttac actgatgaaa  2460
ccttcaaaac cagggaggcc atccagcatg agtctggcat cctgggccct ctgctgtatg  2520
gagaggtggg agacaccctg ctgatcatct tcaagaacca ggccagcagg ccctacaaca  2580
tctatcctca tggcatcact gatgtgagac ctctgtacag caggaggctg cctaaggggg  2640
tgaaacacct gaaggacttt cccatcctgc ctggggagat cttcaagtat aagtggactg  2700
tgactgtgga ggatggccct accaagtctg accccaggtg tctgacaagg tattacagca  2760
gctttgtgaa catggagagg gacctggcct ctggcctgat tggccctctg ctgatctgct  2820
acaaggagtc tgtggaccag aggggcaacc agatcatgtc tgacaagagg aatgtgatcc  2880
tgttctctgt gtttgatgag aataggagct ggtatctgac tgagaacatc cagagattcc  2940
tgcccaatcc tgctggggtg cagctggagg accctgagtt tcaggccagc aatatcatgc  3000
acagcatcaa tggctatgtg tttgacagcc tgcagctgtc tgtgtgcctg catgaggtgg  3060
cctactggta catcctgagc attggagccc agactgattt tctgtctgtg ttcttttctg  3120
gctatacctt caagcacaag atggtgtatg aggacaccct gaccctgttc cccttctctg  3180
gggagactgt gttcatgtct atggagaatc ctgggctgtg gattctgggc tgccacaact  3240
ctgatttcag gaacaggggc atgactgccc tgctgaaggt gagcagctgt gacaagaaca  3300
ctggggacta ctatgaggat agctatgagg acatttctgc ttatctgctg tctaagaata  3360
atgccattga gcccaggagc ttcagccaga atagcagaca ccctagcacc agacagaaac  3420
agtttaatgc cactaatgtg agcaacaaca gcaacaccag caatgacagc aatgtgtcta  3480
acaagacatc taacaacagc aatgccacaa acaagaccaa caacacaaat gatagcacaa  3540
acaggaccaa ccagaccaat accagccccc ctgtgctgaa gagacatcag agggagatca  3600
ccaggactac cctgcagtct gatcaggagg agattgacta tgatgacaca atctctgtgg  3660
agatgaagaa ggaggatttt gacatctatg atgaggatga gaaccagagc cccagatctt  3720
ttcagaagaa gaccagacac tacttcattg ctgctgtgga gaggctgtgg gactatggca  3780
tgagcagcag ccctcatgtg ctgaggaaca gggcccagtc tggctctgtg ccccagttca  3840
agaaggtggt gttccaggag tttactgatg gcagcttcac ccagcccctg tacagagggg  3900
agctgaatga gcacctgggc ctgctgggcc cttatatcag ggctgaggtg gaggataaca  3960
ttatggtgac tttcaggaac caggcctcta ggccctacag cttctatagc agcctgatct  4020
cttatgagga ggatcagagg caggggggctg agcccagaaa gaactttgtg aagcctaatg  4080
agactaagac ctacttctgg aaggtccagc accacatggc cccccaccaag gatgagtttg  4140
attgcaaggc ctgggcctat ttctctgatg tggacctgga gaaggatgtc cattctggcc  4200
tgattggccc tctgctggtg tgccacacta acactctgaa tcctgcccat ggcaggcagg  4260
tgactgtcca ggagtttgcc ctgttcttca ctatctttga tgagaccaag agctggtact  4320
ttactgagaa catggagaga aactgcaggg ctccttgcaa tatccagatg gaggacccca  4380
```

```
ccttcaagga gaactacagg tttcatgcca tcaatgggta catcatggac accctgcctg  4440
gcctggtgat ggctcaggac cagagaatca gatggtatct gctgagcatg ggcagcaatg  4500
agaatatcca cagcatccac ttctctggac atgtgttcac tgtgaggaag aaggaggagt  4560
acaagatggc tctgtataat ctgtaccctg gagtgtttga aactgtggag atgctgcctt  4620
ctaaggctgg catctggagg gtggagtgcc tgattgggga gcacctgcat gctggcatga  4680
gcaccctgtt cctggtgtac agcaacaagt gtcagacccc cctgggcatg gcctctggac  4740
acatcaggga cttccagatc acagcctctg gccagtatgg ccagtgggcc cccaagctgg  4800
ccaggctgca ttattctggc agcatcaatg cctggtctac caaggagccc tttagctgga  4860
tcaaggtgga cctgctggcc cccatgatta tccatggcat caagacccag gggccaggc   4920
agaagttctc tagcctgtac atcagccagt tcatcatcat gtactctctg gatggcaaga  4980
agtggcagac ctacaggggc aacagcactg gcacactgat ggtgttcttt ggcaatgtgg  5040
acagctctgg catcaagcac aacatcttca atccccccat tatcgctagg tatattaggc  5100
tgcatcccac ccactacagc atcagatcta ccctgagaat ggagctgatg ggctgtgacc  5160
tgaactcttg cagcatgccc ctgggcatgg agtctaaggc catctctgat gcccagatta  5220
ctgccagcag ctacttcacc aatatgtttg ccacctggag cccttctaag gccaggctgc  5280
atctgcaggg gaggagcaat gcctggaggc ctcaggtgaa caaccctaag gagtggctgc  5340
aggtggattt ccagaagacc atgaaggtga ctggagtgac cacccaggga gtcaagagcc  5400
tgctgaccag catgtatgtg aaggagtttc tgatcagctc tagccaggat ggccaccagt  5460
ggactctgtt ctttcagaat gggaaggtga aggtgtttca gggcaatcag gactctttca  5520
cccctgtggt gaacagcctg gaccccccc  tgctgaccag atacctgaga atccaccccc  5580
agagctgggt gcaccagatc gccctgagga tggaggtgct gggctgtgag gctcaggatc  5640
tgtactgaga tatctctaga gtcgacagta ctggtgatca gcctcgactg tgccttctag  5700
ttgccagcca tctgttgttt gcccctcccc cgtgccttcc ttgaccctgg aaggtgccac  5760
tcccactgtc ctttcctaat aaaatgagga aattgcatcg cattgtctga gtaggtgtca  5820
ttctattctg gggggtgggg tggggcagga cagcaagggg gaggattggg aagacaatag  5880
caggcatgct ggggatgcgg tgggctctat ggaaccagct ggggcccg              5928

SEQ ID NO: 62          moltype = AA  length = 14
FEATURE                Location/Qualifiers
source                 1..14
                       mol_type = protein
                       organism = synthetic construct
SEQUENCE: 62
SFSQNPPVLK RHQR                                                   14
```

LINKER PEPTIDE, FVIII PROTEIN OR VARIANT THEREOF CONTAINING LINKER PEPTIDE, AND USE THEREOF

CROSS REFERENCE TO RELATED APPLICATIONS

This is a U.S. national stage application of the International Patent Application No. PCT/CN2023/104477, filed Jun. 30, 2023, which This application claims the benefit of priority from Chinese Provisional Application No. 202210823387.5, filed Jul. 7, 2022, the entire contents of each application being all of which are incorporated by reference herein in their entirety.

SEQUENCE LISTING

The present application contains a Sequence Listing that has been submitted electronically and is hereby incorporated by reference in its entirety. The electronic Sequence Listing is named Sequence_Listing_ST26, was created on Dec. 30, 2024, and is 240,527 bytes in size.

FIELD OF THE INVENTION

The present invention relates to the field of genetic defect treatment drugs, specifically a linker peptide, an FVIII protein containing the linker peptide or a variant thereof, and the use thereof.

BACKGROUND OF THE INVENTION

Hemophilia is a group of X-chromosome-linked monogenic deficiency inherited diseases characterized by coagulation disorders due to coagulation factor deficiencies. Among them, Hemophilia A, which is caused by a lack of FVIII encoded by the F8 gene, is the most common form, affecting up to 80-85% of patients. Currently, the standard treatment for Hemophilia A is replacement therapy, which involves supplementing exogenous FVIII protein, including plasma-derived FVIII (pdFVIII) and recombinant FVIII (rFVIII). pdFVIII is extracted from normal human plasma, and its supply is limited, with risks of blood-borne virus transmission. rFVIII is produced through expression and purification in mammalian cell lines in vitro, which is not limited by blood supply and can effectively reduce the risk of blood-borne virus infection, but it requires highly sophisticated production processes.

The FVIII protein has a short half-life in vivo (average of 12 hours), necessitating lifelong administration and frequent injections (2-3, or even 4 intravenous injections per week) for patients undergoing replacement therapy, resulting in high costs and inconvenience. Conventional long-acting modifications such as Fc fusion (Drug Des Devel Ther 2014, 8:365-371) and PEG modification (Haemophilia 2019, 25:773-781) can extend its half-life to about 19 hours, but only to a limited extent (an increase of 50-60%), and do not significantly reduce the frequency of dosing. Sanofi and Sobi have jointly developed a more long-acting novel FVIII fusion protein (BIVV001; FVIIIFc-vWF-XTEN), which further extends the half-life to 38-44 hours by fusing the Fc fragment of an antibody and the D'D3 domain of the vWF factor, reducing the dosing frequency to once a week (N Engl J Med. 2020, 383:1018-1027). Although these long-acting modifications of protein molecules can extend the half-life to varying degrees and improve the patient's medication experience to some extent, they cannot fundamentally change the treatment mode of "lifelong dosing and repeated injections."

Conversely, FVIII gene therapy aims to correct the genetic defects of Hemophilia A patients at the genetic level, potentially achieving functional "cure" of the disease. Currently, AAV-hFVIII (adeno-associated virus vector for liver-targeted delivery of the normal human FVIII gene) is widely regarded as the "best" option for gene therapy for Hemophilia A. However, existing liver-targeted AAV-FVIII gene therapy has significant limitations (Hemasphere 2021, 5:e540):

i) AAV-hFVIII is only suitable for adult patients aged 18 and above. The livers of children are in rapid growth and development, with hepatocytes dividing actively, making them unsuitable for this therapy (substantially increased risk of gene integration; unintegrated target genes are easily lost during cell division).

ii) AAV is a common virus in humans with a high infection rate. Therefore, many patients have pre-existing AAV neutralizing antibodies, rendering this therapy unusable for these patient groups.

iii) Repeated dosing is not possible. AAV-hFVIII is not lifelong effective, and its expression level may fall below the therapeutic level after several years. At this point, redosing is required to restore therapeutic levels. However, the AAV capsid is highly immunogenic, and virus-specific immune responses are easily induced after the first dose, rendering subsequent injections ineffective.

iv) The hFVIII coding gene is large, exceeding the capacity limit of AAV vectors, making AAV-hFVIII packaging and production difficult. Additionally, AAV therapy has other safety concerns such as random gene integration.

The expression of hFVIII (human Factor VIII) is quite challenging, representing a common and critical technical challenge for both recombinant FVIII production (in vitro expression) and FVIII gene therapy (in vivo expression). The expression level of hFVIII is only 1% to 0.1% of that of ordinary proteins with comparable molecular weights (Hum Gene Ther 1993, 4:259-272; Blood 2004, 103:3412-3419). Therefore, modifying the hFVIII molecule to improve its expression level has become a focus of effort in related fields. FVIII consists of six domains: A1-A2-B-A3-C1-C2, with the B region being 908 aa long, accounting for about 40% of the full length (2332 aa). Deleting the B region does not affect its coagulation function (PNAS 1986, 83:5939-5942) and can significantly increase mRNA (17-fold) and protein product (30%) levels (Blood 2004, 103: 3412-3419; Blood Coagul Fibrinolysis 1997, 8 Suppl 2:S3-14). Therefore, deletion of the B region has become a widely adopted modification method; in fact, multiple B-domain-deleted FVIII drugs (BDD-FVIII) have been clinically used on a large scale for many years, such as Xyntha produced by Pfizer. The earliest BDD-FVIII almost completely deleted the B region, retaining only a linker consisting of 4 amino acids from the N-terminus and 10 amino acids from the C-terminus of the natural FVIII B region (a total of 14 aa) to connect A1-A2 with A3-C1-C2 (this linker is called the SQ linker; the sequence is SFSQNPPVLKRHQR). For convenience, BDD-FVIII containing the SQ linker is denoted as BDD-FVIII-SQ. We attempted to study the feasibility of using a mini-circle DNA vector for in vivo expression of therapeutic levels of BDD-FVIII-SQ; however, experiments found that the BDD-FVIII-SQ vector could only express very weakly in vivo (less than 1% of normal levels), failing to achieve therapeutic effects. Therapeutic levels have three tiers: i) exceeding 1% for preliminary efficacy, alleviating severe hemophilia to moderate; ii) exceeding 5% for significant efficacy, significantly alleviating moderate to severe hemophilia to mild; iii) exceeding 50% for functional "cure," fully restoring normal coagulation function.

The B-region linker connects A1-A2 with A3-C1-C2, and its sequence has an important impact on the expression level of the BDD-FVIII protein. Miao et al. (Blood 2004, 103: 3412-3419) reported that retaining the first 226 amino acids (226aa/N6) of the N-terminus of the B region results in a 4-fold higher expression level than almost completely deleting the B region (wild-type SQ linker) when detected by ELISA. McIntosh et al. (Blood 2013, 121:3335-3344; Patent: WO 2013/186563) further replaced the 226aa/N6 with a 31 aa-long v3 linker (sequence: SFSQNATNVSNNSNTSNDSNVSPPVLKRHQR) on this basis and found that it could further increase the expression level of the target protein (by about 50%). The present invention denotes BDD-FVIII containing the v3 linker as BDD-FVIII-v3. Currently, AAV gene therapy based on BDD-FVIII-v3 has initiated Phase I clinical trials (NCT03001830). Novo Nordisk (Denmark) has developed another BDD-FVIII molecule (N8) with better expression than BDD-FVIII-SQ, containing a 21 aa-long linker (sequence: SFSQNSRHPSQNPPVLKRHQR) (Haemophilia 2010, 16:349-359; Patent: WO2006103298); the present invention denotes this molecule as BDD-FVIII-N8. However, BDD-FVIII-v3 and BDD-FVIII-N8 still have issues such as low expression levels and poor therapeutic effects.

Therefore, there is still an urgent need for a drug for treating diseases related to Factor VIII deficiency that has high expression levels, allows for secondary dosing, is simple to prepare, has good therapeutic effects, and can be expressed long-term in vivo.

SUMMARY OF THE INVENTION

In order to solve the above problems, the technical solutions provided by the present disclosure are as follows.

In a first aspect, a linker peptide is provided. The recombinant FVIII protein or the variant thereof using the linker peptide provided by the present disclosure has the advantages such as high expression level, good effect in secondary administration, simple preparation, and good therapeutic effect. The minicircle DNA of the recombinant FVIII protein or the variant thereof using the linker peptide provided by the present disclosure has the advantages such as high expression level, good effect in secondary administration, simple preparation and, good therapeutic effect, and also solves the problems of difficulty in production (difficulty in packaging), limitation in application range (failure to be used in children, failure to perform secondary administration), and safety risk (carcinogenesis due to random integration) of AAV.hf8, that is, the advantages such as simple production, wide application range (capability of being used in children, good efficacy in secondary administration), good safety, and long-term expression in vivo are provided.

In a second aspect, a nucleotide sequence is provided. The nucleotide sequence can encode the linker peptide of the first aspect.

In a third aspect, the use of the linker peptide of the first aspect or the nucleotide sequence of the second aspect is provided.

In a fourth aspect, a recombinant FVIII protein or a variant thereof is provided. The recombinant FVIII protein or the variant thereof has the advantages such as high expression level, good effect in secondary administration, simple preparation, and good therapeutic effect.

In a fifth aspect, a nucleotide is provided.

In a sixth aspect, a recombinant gene vector is provided.

In a seventh aspect, a parental plasmid for use in the production of a minicircle DNA is provided.

In an eighth aspect, a method for preparing a minicircle DNA is provided.

In a ninth aspect, a minicircle DNA obtained according to the preparation method of the eighth aspect is provided. The minicircle DNA has the advantages such as high expression level, good effect in secondary administration, simple preparation, and good therapeutic effect, and solves the problems of difficulty in production (difficulty in packaging), limitation in application range (failure to be used in children, failure to perform secondary administration), and safety risk (carcinogenesis due to random integration) of AAV.hf8, that is, the advantages such as simple production, wide application range (capability of being used in children, good efficacy in secondary administration), good safety, and long-term expression in vivo are provided.

In a tenth aspect, a host cell comprising a nucleotide sequence encoding the recombinant FVIII protein or the variant thereof of the fourth aspect, the nucleotide sequence of the fifth aspect, the recombinant gene vector of the sixth aspect or the minicircle DNA of the ninth aspect is provided.

In an eleventh aspect, a pharmaceutical composition is provided.

In a twelfth aspect, the use of the recombinant FVIII protein or the variant thereof of the fourth aspect, the nucleotide sequence of the fifth aspect, the recombinant gene vector of the sixth aspect, the parental plasmid of the seventh aspect, the minicircle DNA obtained according to the preparation method of the eighth aspect, the minicircle DNA of the ninth aspect, the host cell of the tenth aspect or the pharmaceutical composition of the eleventh aspect for the preparation of a drug for treating a disease is provided.

BRIEF SUMMARY OF THE DRAWINGS

FIG. 21A and FIG. 21B are diagrams showing the pathological section results of beagle dogs after the injection with MC.BDD-FVIII-L1 minicircle DNA in Example 13.

DETAILED DESCRIPTION OF THE INVENTION

Figure 1:
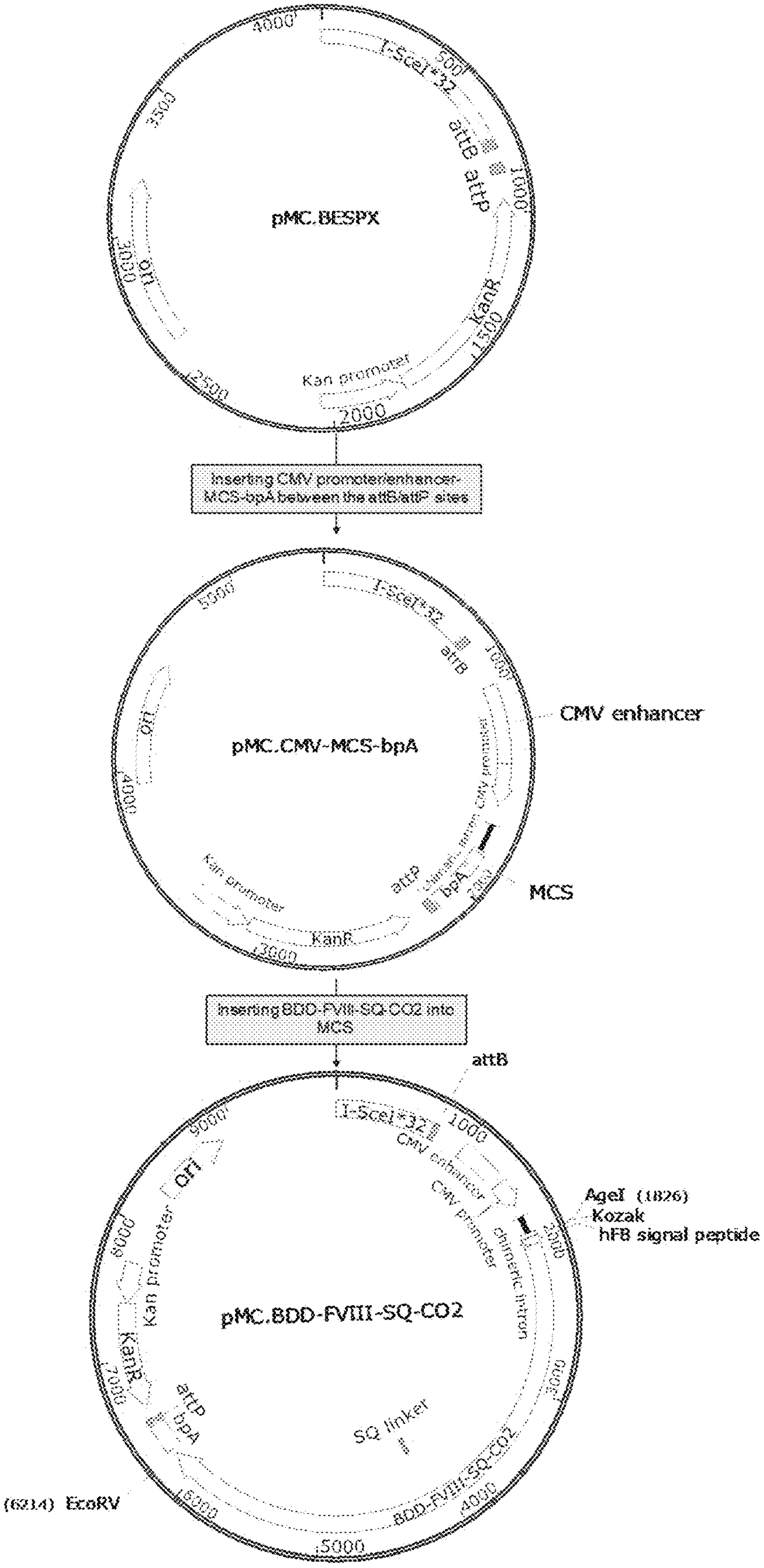
FIG. 1 is a schematic diagram of the construction process of the minicircle DNA parent plasmid pMC.BDD-FVIII-SQ-CO2 in Example 1.
Figure 2:
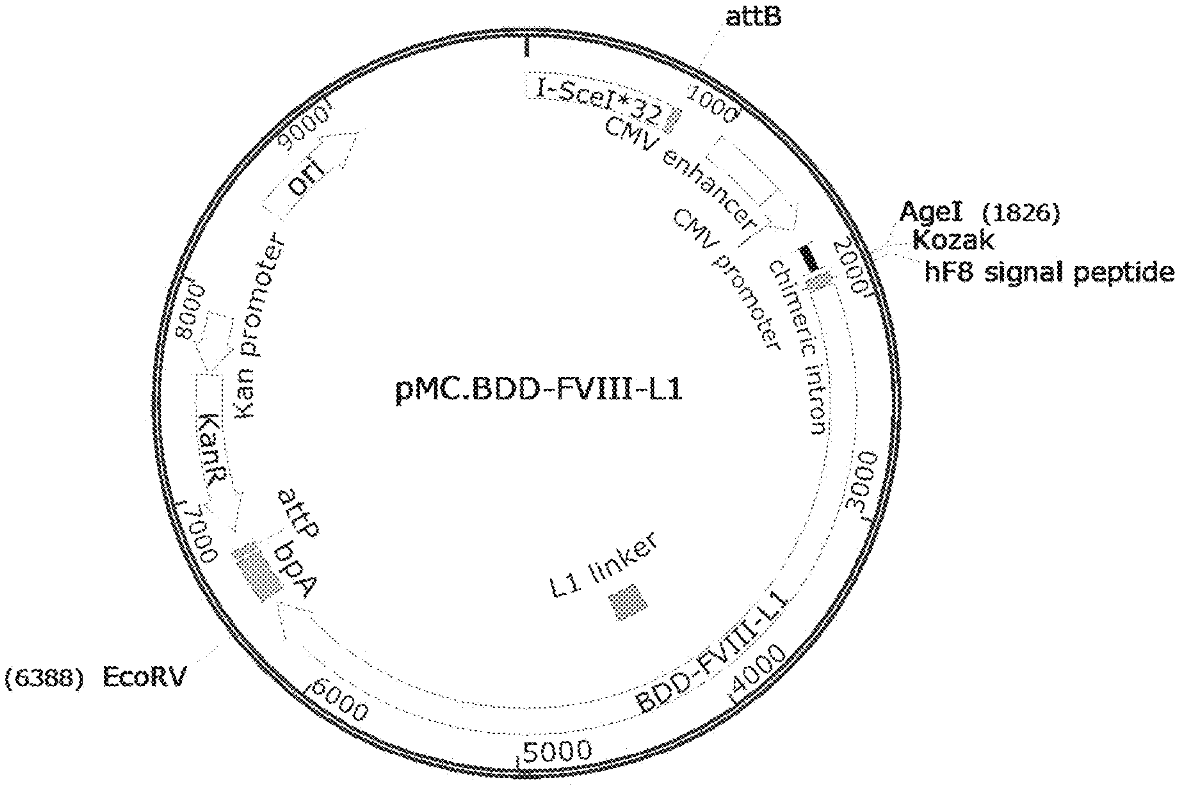
FIG. 2 is a schematic structural diagram of the minicircle DNA parent plasmid pMC.BDD-FVIII-L1 in Example 1.
Figure 3:
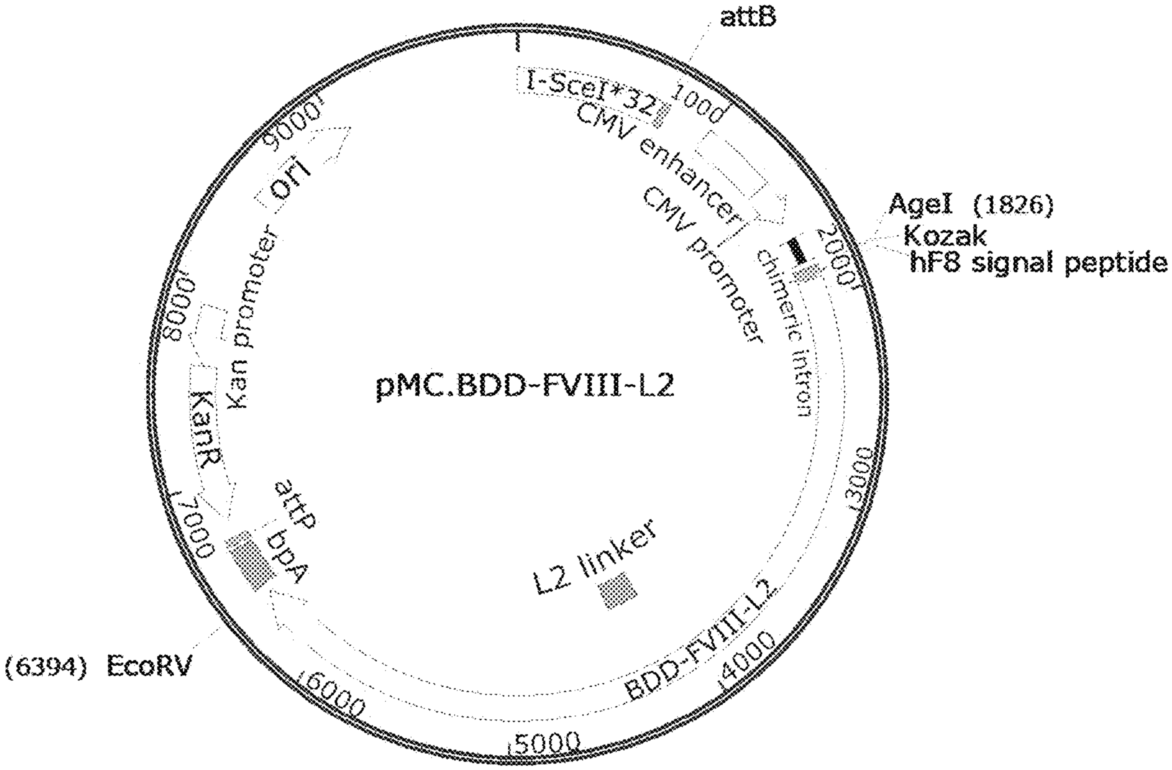
FIG. 3 is a schematic structural diagram of the minicircle DNA parent plasmid pMC.BDD-FVIII-L2 in Example 1.
Figure 4:
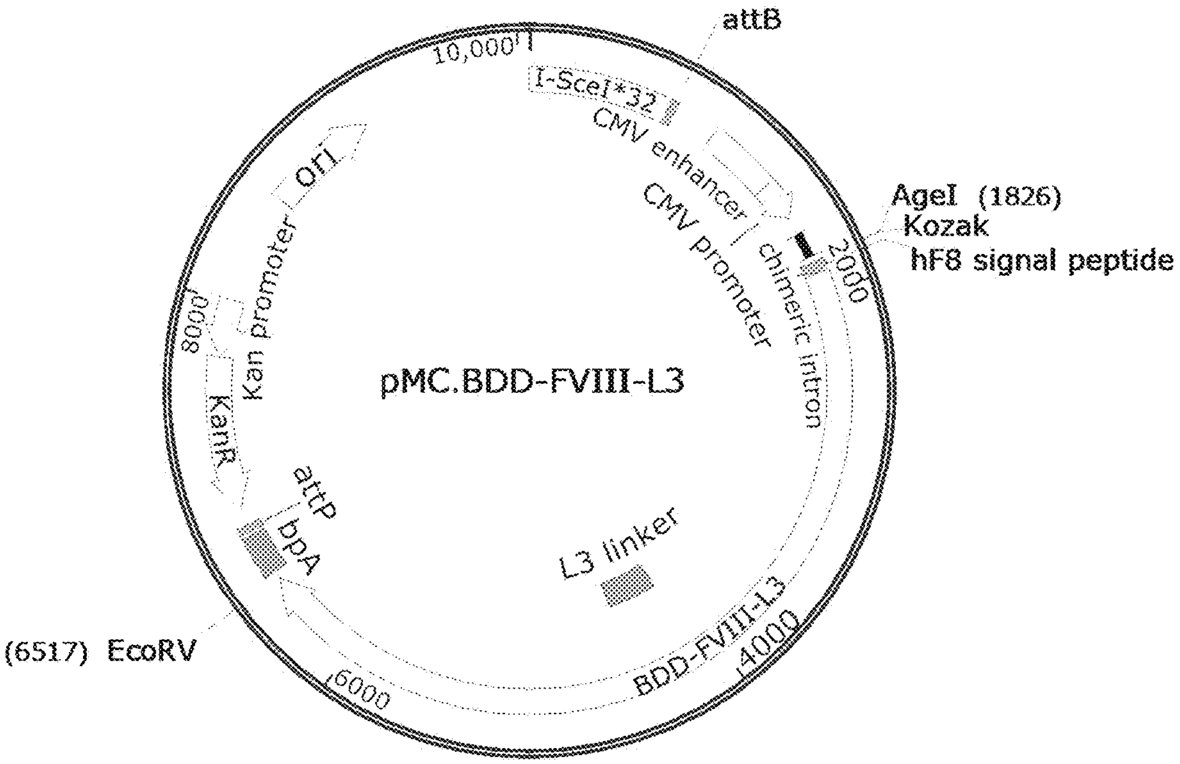
FIG. 4 is a schematic structural diagram of the minicircle DNA parent plasmid pMC.BDD-FVIII-L3 in Example 1.
Figure 5:
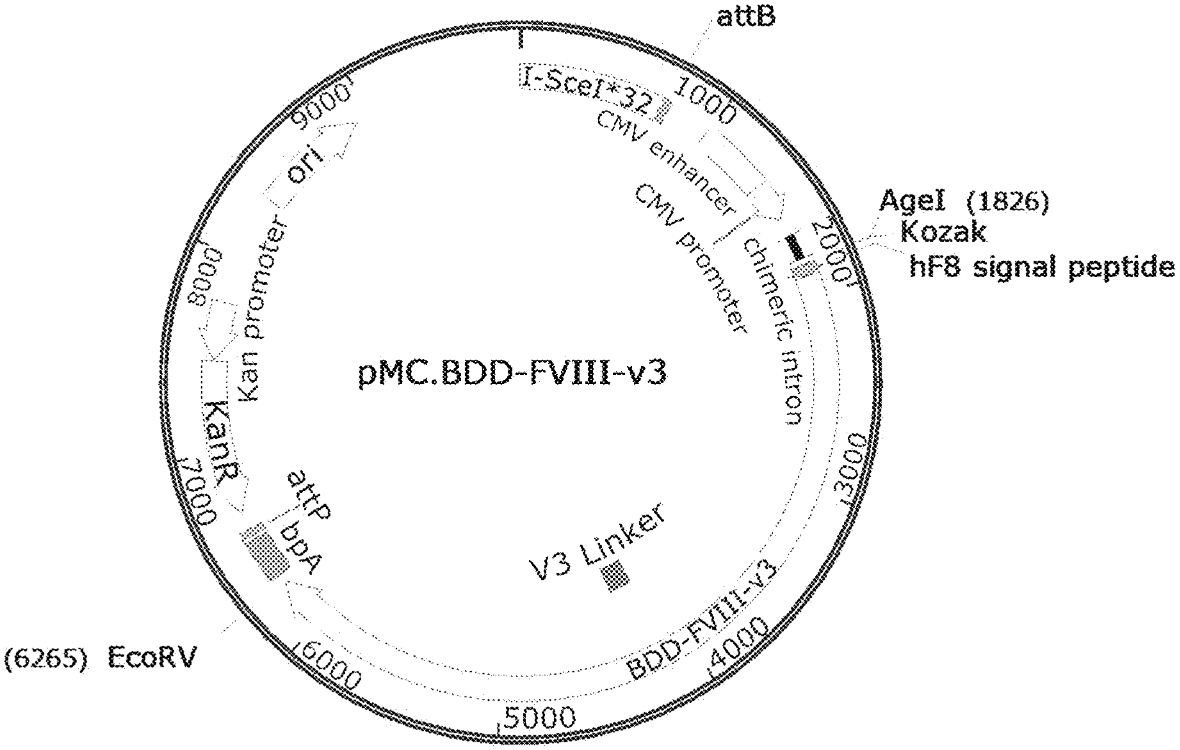
FIG. 5 is a schematic structural diagram of the minicircle DNA parent plasmid pMC.BDD-FVIII-v3 in Example 1.
Figure 6:
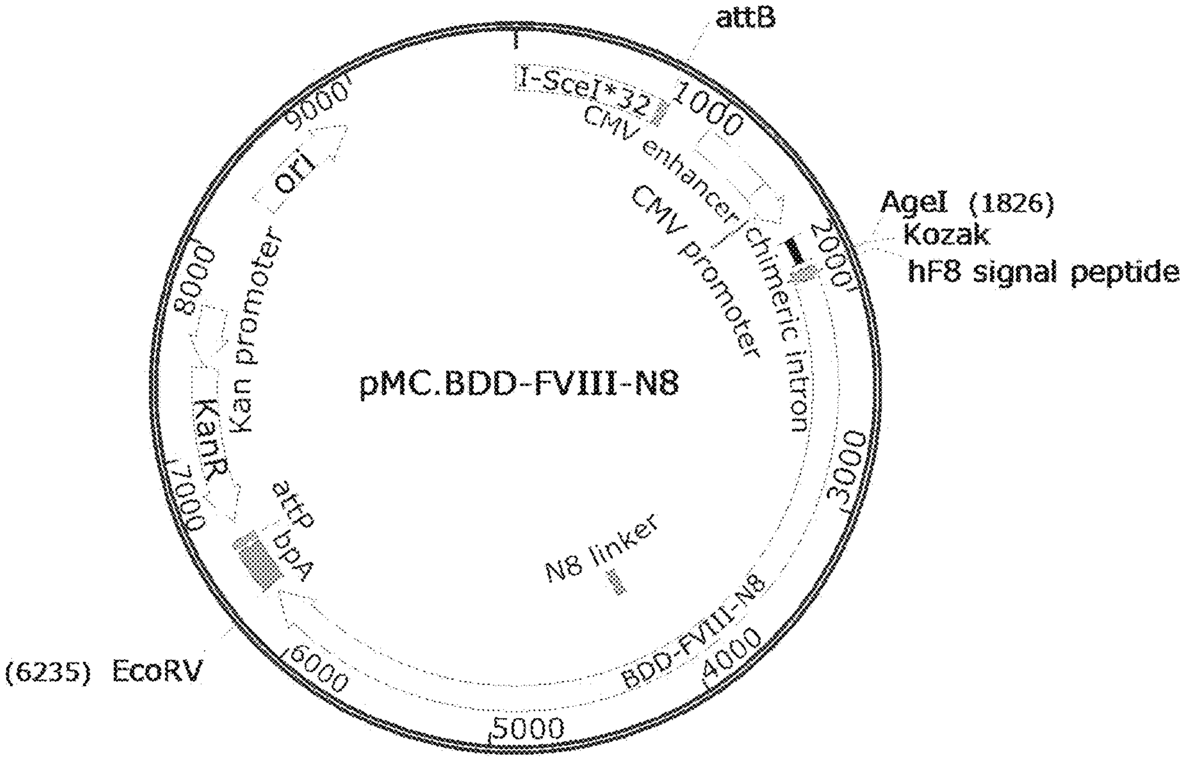
FIG. 6 is a schematic structural diagram of the minicircle DNA parent plasmid pMC.BDD-FVIII-N8 in Example 1.

In order to solve the above problems, the technical solutions provided by the present disclosure are as follows.

In a first aspect, a linker peptide is provided.

A linker peptide having an amino acid sequence of SEQ ID NO. 1 or SEQ ID NO. 2, or having an amino acid sequence having at least 80%-99% identity to any one of the nucleotide sequences or having at least a portion of either of the sequences. The recombinant FVIII protein or the variant thereof using the linker peptide provided by the first aspect of the present disclosure has the advantages such as high expression level, good effect in secondary administration, simple preparation, and good therapeutic effect. The minicircle DNA of the recombinant FVIII protein or the variant thereof using the linker peptide provided by the first aspect of the present disclosure has the advantages such as high expression level, good effect in secondary administration, simple preparation, and good therapeutic effect, and also solves the problems of difficulty in production (difficulty in packaging), limitation in application range (failure to be used in children, failure to perform secondary administration), and safety risk (carcinogenesis due to random integration) of AAV.hf8, that is, the advantages such as simple production, wide application range (capability of being used in children, good efficacy in secondary administration), good safety, and long-term expression in vivo are provided.

In some embodiments, the nucleotide sequence encoding the linker peptide having an amino acid sequence of SEQ ID NO. 1 (abbreviated as L1 linker in the present disclosure) may include SEQ ID NO. 3 or a codon-optimized sequence thereof.

In some embodiments, the nucleotide sequence encoding the linker peptide having an amino acid sequence of SEQ ID NO. 2 (abbreviated as L2 linker in the present disclosure) may include SEQ ID NO. 4 or a codon-optimized sequence thereof.

In a second aspect, a nucleotide sequence is provided.

A nucleotide sequence encoding the linker peptide of the first aspect.

In some embodiments, the nucleotide sequence includes SEQ ID NO. 3 or SEQ ID NO. 4, or a codon-optimized sequence of either of the nucleotide sequences.

In some embodiments, the nucleotide sequence of SEQ ID NO. 3 or a codon-optimized sequence thereof may be used to encode a linker peptide having an amino acid sequence of SEQ ID NO. 1.

In some embodiments, the nucleotide sequence of SEQ ID NO. 4 or a codon-optimized sequence thereof may be used to encode a linker peptide having an amino acid sequence of SEQ ID NO. 2.

In a third aspect, the use of the linker peptide of the first aspect or the nucleotide sequence of the second aspect is provided.

Use of the linker peptide of the first aspect or the nucleotide sequence of the second aspect for the construction of a recombinant FVIII protein or a variant thereof.

Use of the nucleotide sequence of the second aspect for the construction of a nucleotide sequence of a recombinant FVIII protein or a variant thereof.

In a fourth aspect, a recombinant FVIII protein or a variant thereof is provided.

An FVIII protein or a variant thereof, wherein the linker peptide of the FVIII protein or the variant thereof is selected from the linker peptide of the first aspect, or the nucleotide sequence of the linker peptide of the FVIII protein or the variant thereof is selected from the nucleotide sequence of the second aspect. The recombinant FVIII protein or the variant thereof provided by the fourth aspect of the present disclosure has the advantages such as high expression level, good effect in secondary administration, simple preparation, and good therapeutic effect.

In some embodiments, the recombinant FVIII protein or the variant thereof has an amino acid sequence of SEQ ID NO. 5, SEQ ID NO. 6, SEQ ID NO. 21, SEQ ID NO. 23, SEQ ID NO. 43, SEQ ID NO. 44, SEQ ID NO. 50, SEQ ID NO. 51, SEQ ID NO. 52 or SEQ ID NO. 53, or has an amino acid sequence having at least 80%-99% identity to any one of the amino acid sequences or has at least a portion of any one of the amino acid sequences.

In some embodiments, the nucleotide sequence encoding the recombinant FVIII protein or the variant thereof having the amino acid sequence of SEQ ID NO. 5 may include SEQ ID NO. 7 or a codon-optimized sequence thereof.

In some embodiments, the nucleotide sequence encoding the recombinant FVIII protein or the variant thereof having the amino acid sequence of SEQ ID NO. 6 may include SEQ ID NO. 8 or a codon-optimized sequence thereof.

In some embodiments, the nucleotide sequence encoding the recombinant FVIII protein or the variant thereof having the amino acid sequence of SEQ ID NO. 21 may include SEQ ID NO. 22 or a codon-optimized sequence thereof.

In some embodiments, the nucleotide sequence encoding the recombinant FVIII protein or the variant thereof having the amino acid sequence of SEQ ID NO. 23 may include SEQ ID NO. 24 or a codon-optimized sequence thereof.

In some embodiments, the nucleotide sequence encoding the recombinant FVIII protein or the variant thereof having the amino acid sequence of SEQ ID NO. 43 may include SEQ ID NO. 38 or a codon-optimized sequence thereof.

In some embodiments, the nucleotide sequence encoding the recombinant FVIII protein or the variant thereof having the amino acid sequence of SEQ ID NO. 44 may include SEQ ID NO. 39 or a codon-optimized sequence thereof.

In some embodiments, the nucleotide sequence encoding the recombinant FVIII protein or the variant thereof having the amino acid sequence of SEQ ID NO. 50 may include SEQ ID NO. 56 or a codon-optimized sequence thereof.

In some embodiments, the nucleotide sequence encoding the recombinant FVIII protein or the variant thereof having the amino acid sequence of SEQ ID NO. 51 may include SEQ ID NO. 60 or a codon-optimized sequence thereof.

In some embodiments, the nucleotide sequence encoding the recombinant FVIII protein or the variant thereof having the amino acid sequence of SEQ ID NO. 52 may include SEQ ID NO. 58 or a codon-optimized sequence thereof.

In some embodiments, the nucleotide sequence encoding the recombinant FVIII protein or the variant thereof having the amino acid sequence of SEQ ID NO. 53 may include SEQ ID NO. 54 or a codon-optimized sequence thereof.

In a fifth aspect, a nucleotide is provided.

A nucleotide sequence encoding the recombinant FVIII protein or the variant thereof of the fourth aspect.

In some embodiments, the nucleotide sequence includes SEQ ID NO. 7, SEQ ID NO. 8, SEQ ID NO. 22, SEQ ID NO. 24, SEQ ID NO. 38, SEQ ID NO. 39, SEQ ID NO. 54, SEQ ID NO. 56, SEQ ID NO. 58 or SEQ ID NO. 60, or a codon-optimized sequence of any one of the nucleotide sequences.

In some embodiments, the nucleotide sequence of SEQ ID NO. 7 may be used to encode the recombinant FVIII protein or the variant thereof having an amino acid sequence of SEQ ID NO. 5.

In some embodiments, the nucleotide sequence of SEQ ID NO. 8 may be used to encode the recombinant FVIII protein or the variant thereof having an amino acid sequence of SEQ ID NO. 6.

In some embodiments, the nucleotide sequence of SEQ ID NO. 22 may be used to encode the recombinant FVIII protein or the variant thereof having an amino acid sequence of SEQ ID NO. 21.

In some embodiments, the nucleotide sequence of SEQ ID NO. 24 may be used to encode the recombinant FVIII protein or the variant thereof having an amino acid sequence of SEQ ID NO. 23.

In some embodiments, the nucleotide sequence of SEQ ID NO. 38 may be used to encode the recombinant FVIII protein or the variant thereof having an amino acid sequence of SEQ ID NO. 43.

In some embodiments, the nucleotide sequence of SEQ ID NO. 39 may be used to encode the recombinant FVIII protein or the variant thereof having an amino acid sequence of SEQ ID NO. 44.

In some embodiments, the nucleotide sequence of SEQ ID NO. 54 may be used to encode the recombinant FVIII protein or the variant thereof having an amino acid sequence of SEQ ID NO. 53.

In some embodiments, the nucleotide sequence of SEQ ID NO. 56 may be used to encode the recombinant FVIII protein or the variant thereof having an amino acid sequence of SEQ ID NO. 50.

In some embodiments, the nucleotide sequence of SEQ ID NO. 58 may be used to encode the recombinant FVIII protein or the variant thereof having an amino acid sequence of SEQ ID NO. 52.

In some embodiments, the nucleotide sequence of SEQ ID NO. 60 may be used to encode the recombinant FVIII protein or the variant thereof having an amino acid sequence of SEQ ID NO. 51.

In a sixth aspect, a recombinant gene vector is provided.

A recombinant gene vector, comprising a nucleotide sequence encoding the recombinant FVIII protein or the variant thereof of the fourth aspect, or the nucleotide sequence of the fifth aspect.

In some embodiments, the recombinant gene vector may include a non-viral vector or a viral vector.

In some embodiments, the non-viral vector may be selected from a standard plasmid or other circular expression cassettes.

In some embodiments, the viral vector may be selected from a retroviral vector, a lentiviral vector, an adenoviral vector and an adeno-associated viral vector.

In some preferred embodiments, the non-viral vector may be selected from a minicircle DNA vector.

In a seventh aspect, a parental plasmid for use in the production of a minicircle DNA is provided.

A parental plasmid for use in the production of a minicircle DNA, comprising a plasmid vector containing the nucleotide sequence of the fifth aspect.

In some embodiments, the parental plasmid for use in the production of a minicircle DNA is formed by inserting in a plasmid vector a promoter nucleotide sequence, an enhancer nucleotide sequence, a multiple cloning site nucleotide sequence, a polyA signal nucleotide sequence, and a DNA fragment of a gene of interest, wherein the DNA fragment of the gene of interest is located between the restriction endonuclease cleavage sites of the multiple cloning site, and the DNA fragment of the gene of interest comprises the nucleotide sequence of the fifth aspect.

In some embodiments, the promoter may be a CMV promoter, and the nucleotide sequence thereof may be SEQ ID NO. 29.

In some embodiments, the enhancer nucleotide sequence may be SEQ ID NO. 30.

In some embodiments, the multiple cloning site nucleotide sequence may be SEQ ID NO. 31.

In some embodiments, the polyA signal may be selected from a bovine growth hormone polyA signal, a human growth hormone polyA signal, or an SV40 polyA signal.

In some embodiments, the bovine growth hormone polyA signal nucleotide sequence may be SEQ ID NO. 32.

In some embodiments, the DNA fragment of the gene of interest may also comprise a Kozak sequence and a sequence encoding a human FVIII gene signal peptide. The Kozak sequence is advantageous for enhancing transcription of the gene of interest.

In some embodiments, the nucleotide sequence of the Kozak sequence may be SEQ ID NO. 63 (GCCACC).

In some embodiments, the sequence encoding a human FVIII gene signal peptide may be SEQ ID NO. 33 or SEQ ID NO. 34.

In some embodiments, the plasmid vector is selected from a pMC.BESPX plasmid or a p2ΦC31 plasmid.

In some embodiments, the promoter nucleotide sequence, enhancer nucleotide sequence, multiple cloning site nucleotide sequence, and polyA signal nucleotide sequence are inserted into the plasmid at the recombination sites attB and attP of the plasmid.

In some embodiments, the DNA fragment of the gene of interest is inserted into the plasmid at the restriction endonuclease cleavage sites AgeI and EcoRV of the multiple cloning site.

In an eighth aspect, a method for preparing a minicircle DNA is provided.

A method for preparing a minicircle DNA, comprising: transforming the parental plasmid of the seventh aspect into a host cell, performing induction to allow the parental plasmid to produce a minicircle DNA and a backbone DNA by site-specific recombination at specific recombination sites, and extracting the minicircle DNA using a plasmid DNA purification kit.

In some embodiments, the backbone DNA is linearized within the host cell and subsequently degraded.

In some embodiments, the induction may include induction with L-arabinose.

In a ninth aspect, a minicircle DNA is provided.

A minicircle DNA obtained according to the preparation method of the eighth aspect. The minicircle DNA provided by the ninth aspect of the present disclosure has the advantages such as high expression level, good effect in secondary administration, simple preparation, and good therapeutic effect, and solves the problems of difficulty in production (difficulty in packaging), limitation in application range (failure to be used in children, failure to perform secondary administration), and safety risk (carcinogenesis due to random integration) of AAV.hf8, that is, the advantages such as simple production, wide application range (capability of being used in children, good efficacy in secondary administration), good safety, and long-term expression in vivo are provided.

In some embodiments, the nucleotide sequence of the minicircle DNA may be selected from SEQ ID NO. 25, SEQ ID NO. 26, SEQ ID NO. 27, SEQ ID NO. 28, SEQ ID NO. 46, SEQ ID NO. 47, SEQ ID NO. 49, SEQ ID NO. 55, SEQ ID NO. 57, SEQ ID NO. 59 or SEQ ID NO. 61.

In a tenth aspect, a host cell is provided.

A host cell, comprising a nucleotide sequence encoding the recombinant FVIII protein or the variant thereof of the fourth aspect, the nucleotide sequence of the fifth aspect, the recombinant gene vector of the sixth aspect or the minicircle DNA of the ninth aspect.

In some embodiments, the host cell may include a bacterial cell, a yeast cell, an insect cell or a mammalian cell. In some embodiments, the host cell is selected from *Escherichia coli*. In some embodiments, the host cell is selected from *Escherichia coli* ZYCY10P3S2T.

In an eleventh aspect, a pharmaceutical composition is provided.

A pharmaceutical composition, comprising the recombinant FVIII protein or the variant thereof of the fourth aspect, the recombinant FVIII protein or the variant thereof encoded by the nucleotide sequence of the fifth aspect, the recombinant gene vector of the sixth aspect or the minicircle DNA obtained according to the preparation method of the eighth aspect or the minicircle DNA of the ninth aspect, and a pharmaceutically acceptable auxiliary material or carrier. The pharmaceutical composition provided by the eleventh aspect of the present disclosure has the advantages such as high expression level, good effect in secondary administration, simple preparation, and good therapeutic effect, and solves the problems of difficulty in production (difficulty in packaging), limitation in application range (failure to be used in children, failure to perform secondary administration), and safety risk (carcinogenesis due to random integration) of AAV.hf8, that is, the advantages such as simple production, wide application range (capability of being used in children, good efficacy in secondary administration), good safety, and long-term expression in human bodies are provided.

In a twelfth aspect, use is provided.

Use of the recombinant FVIII protein or the variant thereof of the fourth aspect, the nucleotide sequence of the fifth aspect, the recombinant gene vector of the sixth aspect, the parental plasmid of the seventh aspect, the minicircle DNA obtained according to the preparation method of the eighth aspect, the minicircle DNA of the ninth aspect, the host cell of the tenth aspect or the pharmaceutical composition of the eleventh aspect for the preparation of a drug for treating a disease.

In some embodiments, the disease may be selected from a hereditary genetic defect disease.

In some embodiments, the disease may be a disease caused by coagulation factor deficiency.

In some embodiments, the disease may be a disease caused by a deficiency in FVIII.

In some embodiments, the disease may be hemophilia.

In some embodiments, the hemophilia is moderate hemophilia or severe hemophilia.

Beneficial Effects

Compared with the prior art, a certain embodiment of the present disclosure has at least one of the following beneficial technical effects:

(1) The recombinant gene vector, minicircle DNA or pharmaceutical composition provided by the present disclosure, or the recombinant FVIII protein or the variant thereof using the linker peptide provided by the present disclosure has the advantages such as high expression level, good effect in secondary administration, simple preparation, good therapeutic effect, and long-term expression in vivo.

(2) The problems of difficulty in production (difficulty in packaging), limitation in application range (failure to be used in children, failure to perform secondary administration), and safety risk (carcinogenesis due to random integration) of AAV.hf8 are solved, that is, the advantages such as simple production, wide application range (capability of being used in children, good efficacy in secondary administration), good safety, and long-term expression in vivo are provided.

Definition of Terms

The term "room temperature" means ambient temperature, which may be 20° C.-30° C.; in some embodiments, the temperature is 22° C.-28° C.; in some embodiments, the temperature is 24° C.-26° C.; in some embodiments, the temperature is 25° C.

In the description of the description of the present disclosure, the description of reference to terms such as "an embodiment", "some embodiments", "examples", "specific examples", or "some examples" means that specific features, structures, materials or characteristics described in combination with the embodiment(s) or example(s) are comprised in at least one embodiment or example of the present disclosure. In the present description, the schematic expressions of the above terms do not necessarily refer to the same embodiment or example. Moreover, the specific features, structures, materials or characteristics described can be combined in any one or more embodiments or examples in any suitable manner. In addition, without any contradiction, a person skilled in the art may incorporate and combine different embodiments or examples and features of the different embodiments or examples described in the present description.

Generally, the fusion protein of the present disclosure is prepared by a method of biosynthesis. The nucleotide sequence according to the present disclosure, a person skilled in the art can conveniently use various known methods to prepare the encoding nucleic acid of the present disclosure. These methods are for example but not limited to: PCR, artificial synthesis of DNA, etc. Specific methods can refer to J. Sambrook, "Molecular Cloning: A Laboratory Manual". As an embodiment of the present disclosure, a method comprising segmented synthesis of nucleotide sequences, followed by overlap extension PCR can be used for constructing the encoding nucleic acid sequence of the present disclosure.

The term "parental plasmid" refers to the original plasmid that contains the expression cassette of a gene of interest, and a backbone DNA, which parental plasmid can produce a minicircle DNA. The plasmid produces the minicircle DNA after site-specific DNA recombination.

The term "fusion protein" generally refers to a protein obtained by the fusion of two or more proteins or polypeptides. Gene or nucleic acid molecules encoding two or more proteins or polypeptides may be linked to each other to form a fusion gene or fusion nucleic acid molecule. The fusion gene or fusion nucleic acid molecule may encode the fusion protein. Translation of the fusion gene results in a single polypeptide having the properties of at least one, or even each, of the two or more proteins or polypeptides prior to fusion. Recombinant fusion proteins are artificially created by recombinant DNA techniques for biological research or therapy. Recombinant fusion proteins are proteins created by genetic engineering of fusion genes. The present disclosure relates to recombinant fusion proteins, and the terms "fusion proteins" and "recombinant fusion proteins" are used herein with the same meaning. The fusion protein described herein generally comprises at least two domains (A and C), and optionally a third component, a linker between the two domains. The generation of recombinant fusion proteins is known in the art, and usually involves removal of a stop codon from a cDNA sequence encoding a first protein or polypeptide, followed by attachment of a cDNA sequence encoding a second protein in an in-frame manner by ligation or overlap extension PCR. The DNA sequence will then be expressed by the cell as a single protein. The protein can be engineered to include the complete sequence of two original proteins or polypeptides, or only a portion of either.

In the present application, the "pharmaceutical composition" may conveniently be presented in unit dosage form and may be prepared by any of the methods well known in the pharmaceutical field. All methods include the step of bringing into association the active agent with the carrier which constitutes one or more accessory ingredients. In general, the compositions are prepared by uniformly and intimately bringing into association the active compound with a liquid carrier, a finely divided solid carrier, or both.

In the present application, the term "recombinant gene vector" generally refers to a nucleic acid molecule capable of self-replication in a suitable host, which transfers the inserted nucleic acid molecule into and/or between host cells. The recombinant gene vector may include a vector primarily used for inserting DNA or RNA into a cell, a recombinant gene vector primarily used for replicating DNA or RNA, and a recombinant gene vector primarily used for the transcriptional and/or translational expression of DNA or RNA. The recombinant gene vector also include a recombinant gene vector having a variety of the above-mentioned functions. The recombinant gene vector may be a polynucleotide that can be transcribed and translated into a polypeptide when introduced into a suitable host cell. Generally, the recombinant gene vector may produce a desired expression product by culturing a suitable host cell comprising the recombinant gene vector.

In the present application, the term "mutant" may refer to any naturally occurring or engineered molecule that comprises one or more nucleotide or amino acid mutations.

In the present application, the term "nucleotide" refers to a ribonucleotide, deoxynucleotide or a modified form of either type of nucleotide, and combinations thereof.

The term "host cell" used herein refers to a prokaryotic or eukaryotic cell into which a recombinant expression vector can be introduced. The term "transformed" or "transfected" used herein refers to the introduction of a nucleic acid (e.g., a vector) into a cell by various techniques known in the art. Suitable host cells can be transformed or transfected with the DNA sequence of the present disclosure, and can be used for the expression and/or secretion of the target protein.

The term "identity", when used herein to describe an amino acid sequence or nucleic acid sequence relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). The formula is incorporated into the Basic Local Alignment Search Tool (BLAST) program of Altschul et al. (J. Mol. Biol. 215: 403-410, 1990). The percent identity between sequences can be determined using the latest version of BLAST as of the filing date of the present application.

The term "at least 80%-99% sequence identity" refers to at least 80%-99%, at least 81%-99%, at least 82%-99%, at least 83%-99%, at least 84%-99%, at least 85%-99%, at least 86%-99%, at least 87%-99%, at least 88%-99%, at least 89%-99%, at least 90%-99%, at least 91%-99%, at least 92%-99%, at least 93%-99%, at least 94%-99%, at least 95%-99%, at least 96%-99%, at least 97%-99%, at least 98%-99%, or at least 99% sequence identity to the respective reference sequence.

In the present disclosure, the "MC.BDD-FVIII-L1" or "MC.BDD-FVIII-L1 minicircle DNA" represents the same meaning, and the meanings of the other terms beginning with "MC.BDD", and so on, for example, the "MC.BDD-FVIII-L2" or "MC.BDD-FVIII-L2 minicircle DNA" represents the same meaning.

DETAILED DESCRIPTION

In order to enable those skilled in the art to understand the technical solutions of the present disclosure better, some non-limiting examples are further disclosed below to further illustrate the present disclosure in detail.

All the reagents used in the present disclosure can be commercially available or prepared by the method described in the present disclosure.

The FVIII concentration in normal human plasma ranges from 100 to 200 ng/mL, and 200 ng/mL is defined as 100% of the normal level (Reference: J Biol Chem 2001, 276: 46340-46346).

In the examples, the amino acid sequences and nucleotide sequences of various connecting peptides, FVIII proteins and minicircles are as follows:

TABLE 1

| Amino acid sequences and nucleotide sequences of various connecting peptides, FVIII proteins, minicircles, etc. | |
|---|---|
| The amino acid sequence of L1 linker: SEQ ID NO. 1 | The amino acid sequence of L2 linker: SEQ ID NO. 2 |
| The nucleotide sequence of L1 linker: SEQ ID NO. 3 | The nucleotide sequence of L2 linker: SEQ ID NO. 4 |
| The amino acid sequence of BDD-FVIII-L1: SEQ ID NO. 5 | The amino acid sequence of BDD-FVIII-L2: SEQ ID NO. 6 |
| The nucleotide sequence-BDD-FVIII-L1: SEQ ID NO. 7 | The nucleotide sequence-BDD-FVIII-L2: SEQ ID NO. 8 |
| The amino acid sequence of v3 linker: SEQ ID NO. 9 | The amino acid sequence of N8 linker: SEQ ID NO. 10 |
| The amino acid sequence of BDD-FVIII-SQ-CO2: SEQ ID NO. 11 | The amino acid sequence of BDD-FVIII-v3: SEQ ID NO. 12 |
| The amino acid sequence of BDD-FVIII-N8: SEQ ID NO. 13 | The amino acid sequence of BDD-FVIII-L3: SEQ ID NO. 14 |
| The nucleotide sequence of BDD-FVIII-SQ-CO2: SEQ ID NO. 15 | The nucleotide sequence of BDD-FVIII-v3: SEQ ID NO. 16 |
| The nucleotide sequence: BDD-FVIII-N8: SEQ ID NO. 17 | The nucleotide sequence: BDD-FVIII-L3: SEQ ID NO. 18 |
| The nucleotide sequence of BDD-FVIII-CTP-Fc: SEQ ID NO. 19 | The amino acid sequence of BDD-FVIII-CTP-Fc: SEQ ID NO. 20 |
| The amino acid sequence of BDD-FVIII-L1-X5: SEQ ID NO. 21 | The nucleotide sequence of BDD-FVIII-L1-X5: SEQ ID NO. 22 |
| The amino acid sequence of BDD-FVIII-L2-X5: SEQ ID NO. 23 | The nucleotide sequence of BDD-FVIII-L2-X5: SEQ ID NO. 24 |
| The nucleotide sequence of MC.BDD-FVIII-L1: SEQ ID NO. 25 | The nucleotide sequence of MC.BDD-FVIII-L2: SEQ ID NO. 26 |
| The nucleotide sequence of MC.BDD-FVIII-L1-X5: SEQ ID NO. 27 | The nucleotide sequence of MC.BDD-FVIII-L2-X5: SEQ ID NO. 28 |
| The nucleotide sequence of CMV promoter: SEQ ID NO. 29 | The nucleotide sequence of CMV enhancer: SEQ ID NO. 30 |
| The nucleotide sequence of multiple cloning site: SEQ ID NO. 31 | The nucleotide sequence of bovine growth hormone polyA signal: SEQ ID NO. 32 |
| The nucleotide sequence of human FVIII gene signal peptide: SEQ ID NO. 33 | The nucleotide sequence of human FVIII signal peptide (unoptimized): SEQ ID NO. 34 |
| The nucleotide sequence of BDD-FVIII-SQ-WT: SEQ ID NO. 35 | The nucleotide sequence of BDD-FVIII-v3-WT: SEQ ID NO. 36 |
| The nucleotide sequence of BDD-FVIII-N8-WT: SEQ ID NO. 37 | The nucleotide sequence of BDD-FVIII-L1-WT: SEQ ID NO. 38 |
| The nucleotide sequence of BDD-FVIII-L2-WT: SEQ ID NO. 39 | The amino acid sequence of BDD-FVIII-SQ-WT: SEQ ID NO. 40 |
| The amino acid sequence of BDD-FVIII-v3-WT: SEQ ID NO. 41 | The amino acid sequence of BDD-FVIII-N8-WT: SEQ ID NO. 42 |
| The amino acid sequence of BDD-FVIII-L1-WT: SEQ ID NO. 43 | The amino acid sequence of BDD-FVIII-L2-WT: SEQ ID NO. 44 |
| The nucleotide sequence of BDD-FVIII-SQ-CO1: SEQ ID NO. 45 | MC.BDD-FVIII-L1-WT The nucleotide sequence of: SEQ ID NO. 46 |
| The nucleotide sequence of MC.BDD-FVIII-L2-WT: SEQ ID NO. 47 | The nucleotide sequence of MC.BDD-FVIII-SQ-CO1: SEQ ID NO. 48 |

TABLE 1-continued

| Amino acid sequences and nucleotide sequences of various connecting peptides, FVIII proteins, minicircles, etc. | |
|---|---|
| The nucleotide sequence of MC.BDD-FVIII-SQ-CO2: SEQ ID NO. 49 | The amino acid sequence of BDD-FVIII-L1$_{R1645H}$: SEQ ID NO. 50 |
| The amino acid sequence of BDD-FVIII$_{F309S}$-L1: SEQ ID NO. 51 | The amino acid sequence of BDD-FVIII$_{F309S}$-L1$_{R1645H}$: SEQ ID NO. 52 |
| The amino acid sequence of BDD-FVIII$_{F309S}$-L2: SEQ ID NO. 53 | The nucleotide sequence of BDD-FVIII$_{F309S}$-L2: SEQ ID NO. 54 |
| The nucleotide sequence of MC.BDD-FVIII$_{F309S}$-L2: SEQ ID NO. 55 | The nucleotide sequence of BDD-FVIII-L1$_{R1645H}$: SEQ ID NO. 56 |
| The nucleotide sequence of MC.BDD-FVIII-L1$_{R1645H}$: SEQ ID NO. 57 | The nucleotide sequence of BDD-FVIII$_{F309S}$-L1$_{R1645H}$: SEQ ID NO. 58 |
| The nucleotide sequence of MC.BDD-FVIII$_{F309S}$-L1$_{R1645H}$: SEQ ID NO. 59 | The nucleotide sequence of BDD-FVIII$_{F309S}$-L1: SEQ ID NO. 60 |
| The nucleotide sequence of MC.BDD-FVIII$_{F309S}$-L1: SEQ ID NO. 61 | The amino acid sequence of SQ linker: SEQ ID NO. 62 |
| The nucleotide sequence of Kozak sequence: SEQ ID NO. 63 | / |

The sequence with "WT" in its sequence name means that its BDD-FVIII coding sequence is a coding sequence obtained by almost completely deletion of the B region (reserving the SQ linker) from the wild-type human FVIII coding sequence (serial number: NM 000132), and the sequence with "CO1" or "CO2" means that its BDD-FVIII coding sequence is a coding sequence obtained by codon optimization of the wild-type human FVIII coding sequence (serial number: NM_000132) from which the region B is almost completely deleted (reserving the SQ linker).

```
SEQ ID NO. 63:
GCCACC
```

Example 1: Construction of Minicircle DNA Parental Plasmids (PPs)

The minicircle DNA parent plasmids were constructed by the following steps:

(1) The nucleotide sequences of CMV promoter (SEQ ID NO.29), CMV enhancer (SEQ ID NO.30), multiple cloning site (MCS) (SEQ ID NO.31), and bovine growth hormone polyadenylation signal (bpA) (SEQ ID NO.32) were inserted between the attB and attP recombination sites of the minicircle DNA cloning vector (pMC.BESPX) to construct the vector pMC.CMV-MCS-bpA.

(2) The DNA fragments of the target genes were synthesized, including the Kozak sequence (SEQ ID NO.63) that can enhance the transcription of the target gene, the human FVIII gene signal peptide coding sequence (SEQ ID NO.33), and the BDD-FVIII coding sequence containing the SQ linker (unoptimized) (SEQ ID NO.35). The synthesized DNA fragments were then cloned between the AgeI/EcoRV restriction sites of the pMC.CMV-MCS-bpA multiple cloning site to construct the minicircle DNA parent plasmid of the wild-type BDD-FVIII containing the SQ linker (pMC.BDD-FVIII-SQ-WT).

(3) Referring to the operations (1) and (2), the SQ linker-containing BDD-FVIII coding sequence (unoptimized) (SEQ ID NO.35) was replaced with the optimized SQ linker-containing BDD-FVIII coding sequence-CO1 (SEQ ID NO.45), the optimized SQ linker-containing BDD- FVIII coding sequence-C02 (SEQ ID NO.15), the optimized v3 linker-containing BDD-FVIII coding sequence (SEQ ID NO.16), the optimized N8 linker-containing BDD-FVIII coding sequence (SEQ ID NO.17), the optimized L1 linker-containing BDD-FVIII coding sequence (SEQ ID NO.7), the optimized L2 linker-containing BDD-FVIII coding sequence (SEQ ID NO.8), the optimized L3 linker-containing BDD-FVIII coding sequence (SEQ ID NO.18), the v3 linker-containing BDD-FVIII coding sequence (SEQ ID NO.36), the N8 linker-containing BDD-FVIII coding sequence (SEQ ID NO.37), the L1 linker-containing BDD-FVIII coding sequence (SEQ ID NO.38), and the L2 linker-containing BDD-FVIII coding sequence (SEQ ID NO.39), to respectively construct different minicircle DNA parent plasmids such as pMC.BDD-FVIII-SQ-CO1, pMC.BDD-FVIII-SQ-C02, pMC.BDD-FVIII-v3, pMC.BDD-FVIII-N8, pMC.BDD-FVIII-L1, pMC.BDD-FVIII-L2, pMC.BDD-FVIII-L3, pMC.BDD-FVIII-v3-WT, pMC.BDD-FVIII-N8-WT, pMC.BDD-FVIII-L1-WT, pMC.BDD-FVIII-L2-WT (the nucleotide sequences of various minicircle DNA parent plasmids refer are shown in Table 1).

Example 2: Production of Minicircle DNA

The minicircle DNA was produced by the following steps:

(1) The parent plasmids (pMC.BDD-FVIII-SQ-WT, pMC.BDD-FVIII-SQ-CO1, pMC.BDD-FVIII-SQ-CO2, pMC.BDD-FVIII-v3, pMC.BDD-FVIII-N8, pMC.BDD-FVIII-L1, pMC.BDD-FVIII-L2, pMC.BDD-FVIII-L3, pMC.BDD-FVIII-L1-WT, and pMC.BDD-FVIII-L2-WT) were respectively transformed into the genetically engineered *E. coli* ZYCY10P3S2T.

(2) The positive monoclonal colonies were picked, inoculated into an LB medium or TB medium, and cultured on a shaker at 37° C. for 12 h to 16 h.

(3) L-arabinose was added (to a final L-arabinose concentration of 0.2 wt %) to perform an induction at an induction temperature of 30° C. to 32° C. for an induction time of 6-8 hours so that parent plasmids were induced to undergo site-specific DNA recombination to form minicircle DNA and skeleton DNA, wherein the skeleton DNA was linearized in the bacterial body and then degraded.

(4) The respective minicircle DNA (wherein the nucleotide sequences of various minicircle DNAs are shown in Table 1) was extracted using a plasmid DNA purification kit (QIAGEN EndoFree Plasmid Mega Kit, Qiagen, Germany): MC.BDD-FVIII-SQ-WT, MC.BDD-FVIII-SQ-CO1, MC.BDD-FVIII-SQ-CO2, MC.BDD-FVIII-v3, MC.BDD-FVIII-N8, MC.BDD-FVIII-L1, MC.BDD-FVIII-L2, MC.BDD-FVIII-L3, MC.BDD-FVIII-L1-WT, and MC.BDD-FVIII-L2-WT.

Example 3: Cell Transfection (1) 293T cells were inoculated into a 6-well plate at a density of $1\times10^6$ cells per well;

(2) The cells were cultured in a DMEM medium containing 10% fetal bovine serum at 37° C., 5% $CO_2$ for 24 hours to obtain cells to be transfected;

(3) The serum-containing DMEM medium was discarded and replaced with a serum-free expression medium (Expi293, Thermo Fisher Scientific), and cultured in an incubator at 37° C. for additional 4 hours;

(4) The minicircle DNA was transfected into the cells to be transfected at an amount of 1.2 μg/well using a transfection reagent (X-tremeGENE HP DNA Transfection Reagent, Roche) to obtain the recombinant cells; and (5) The recombinant cells were cultured for 72 hours, and the cell culture supernatant was collected for subsequent testing.

Example 4: Western Blot Detection (1) Preparation of samples: A reducing loading buffer was respectively added into the collected cell culture supernatant, a negative control sample (transfection reagent), and a positive control sample (hFVIII plasma extract; Guizhou Taibang Biological Products Co., Ltd.);

(2) Electrophoresis: The sample prepared in step (1) was supplemented with an appropriate amount of loading buffer, and then heated in boiling water for 3-5 minutes to denature the protein, cooled, loaded into to the SDS-PAGE gel loading hole, and electrophoresed at 80-100V for 1 hour;

(3) Transfer: The sample was transferred using a wet transfer-blot (Bio-Rad) at 300 mA for 1 hour to transfer the protein from the SDS-PAGE gel to the PVDF membrane;

(4) Blocking: The PVDF membrane was rinsed, and blocked by adding a blocking solution;

(5) Antibody incubation: A diluted HRP-labeled anti-human FVIII antibody (Affinity Biologicals) was added and incubated at room temperature for 1 hour; and (6) Development: The protein was detected using an ECL chemiluminescence reagent (Cell Signaling).

Figure 7:
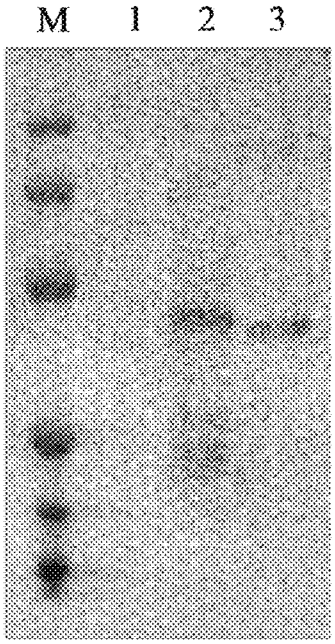
FIG. 7 is a Western blot detection diagram of MC.BDD-FVIII-SQ-CO2 in Example 4; wherein the lane M is a protein marker; the lane 1 is a negative control sample (blank control without transfection of MC vector); the lane 2 is MC.BDD-FVIII-SQ-CO2 cell culture supernatant; and the lane 3 is a positive control sample (hFVIII plasma extract, available from Guizhou Taibang Biological Products Co., Ltd.).

Results: The detection results of MC.BDD-FVIII-SQ-CO2 are shown in FIG. 7.

Example 5: Investigation of BDD-FVIII Codon-Optimized Sequence

The wild-type human FVIII coding sequence (sequence number: NM_000132) was obtained from the Genbank database, and the B region was almost completely deleted (reserving the SQ linker) to construct the wild-type BDD-FVIII-SQ-WT (SEQ ID NO.35). The wild-type BDD-FVIII was subjected to codon optimization using two optimization algorithms to give two optimized BDD-FVIII sequences BDD-FVIII-SQ-CO1 (SEQ ID NO.45) and BDD-FVIII-SQ-CO2 (SEQ ID NO.15), respectively. In accordance with the method as described in Example 1, MC.BDD-FVIII-SQ-WT, MC.BDD-FVIII-SQ-CO1, and MC.BDD-FVIII-SQ-CO2 were prepared (the nucleotide sequences of various minicircles are shown in Table 1). 293 cells were transfected with MC.BDD-FVIII-SQ-WT, MC.BDD-FVIII-SQ-CO1, and MC.BDD-FVIII-SQ-CO2, respectively. After 72 hours, the cell culture supernatant was collected and the expression level of the target protein was detected by ELISA.

Figure 8:
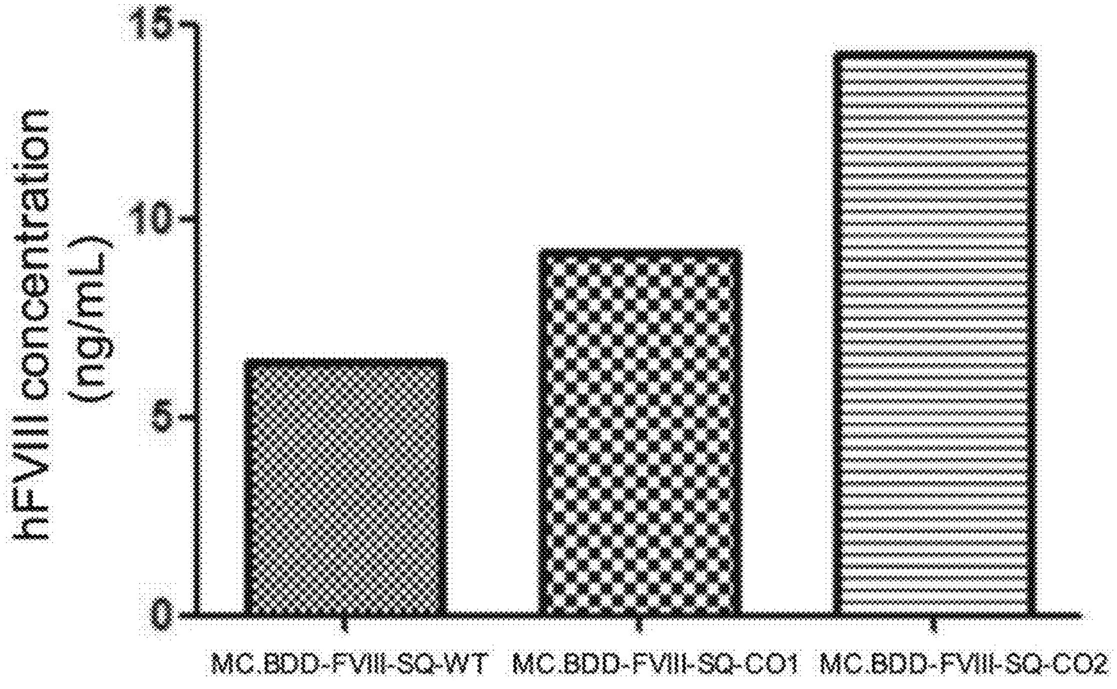
FIG. 8 is a statistical diagram of the results of measuring the in vitro cell expression levels of the target proteins of 293T cells transfected by MC.BDD-FVIII-SQ-WT, MC.BDD-FVIII-SQ-CO1 and MC.BDD-FVIII-SQ-CO2 in Example 5 using ELISA.

Results: As shown in FIG. 8.

Conclusions: The expression levels of the two optimized vectors are significantly improved, and the second optimized version (BDD-FVIII-CO2) has a greater improvement, that is, more than 1 times.

Comparative Example 1: Investigation of In Vivo Expression and Activity of MC.BDD-FVIII-SQ-CO2

Plasma Expression Level of MC.BDD-FVIII-SQ-CO2 in Wild-Type C57 Mice:

Operations: MC.BDD-FVIII-SQ-CO2 was intramuscularly injected into wild-type C57 mice at a dose of 30 μg/mouse, and the plasma expression level was measured by ELISA.

Results: The plasma expression levels were measured by ELISA, and it is found that there was only weak expression (1-2 ng/mL).

Therapeutic Effect of MC.BDD-FVIII-SQ-CO2 on Mice with Hemophilia A with F8 Gene Knockout (F8-KO Mice):

Operations: Six 12-week-old male F8-KO mice were randomly divided into two groups, with 3 in each group. Each mouse in the treatment group was intramuscularly injected with 30 μg/50 μL of the minicircle DNA (MC.BDD-FVIII-SQ-CO2) solution (30 μg minicircle DNA in 50 μl solution), and each mouse in the blank control group was intramuscularly injected with 50 μL PBS. After the intramuscular injection, a pulsed electric field was applied (TERESA in vivo gene introduction instrument; parameters: 36 V, 10 ms, 1 Hz). 1 month (m1) and 2 months (m2) after the injection, the mice were subjected to tail cutting experiments in twice at sites where the mouse tail had diameter of 2 mm and 2.5 mm, respectively, and the bleeding volume was recorded. After the tail cutting, the wound was cauterized with $AgNO_3$ to stop the bleeding.

Figure 9:
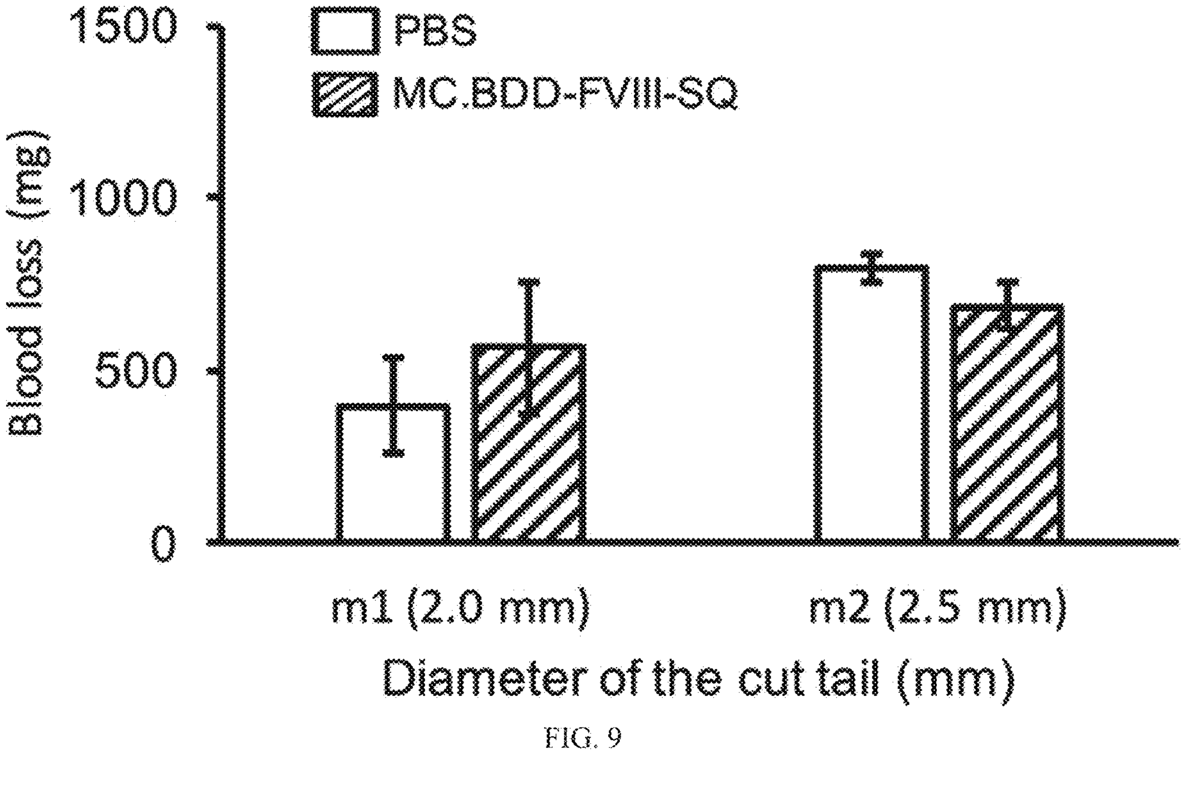
FIG. 9 is a statistical diagram of the therapeutic effect of MC.BDD-FVIII-SQ-CO2 on mice with hemophilia A and F8 gene knockout (F8-KO) in Comparative Example 1, wherein m1/2 mm means that 1 month after the injection, a tail-cutting experiment is performed at a site where the tail has a diameter of 2 mm, and m2/2.5 mm means that 2 months after the injection, a tail-cutting experiment is performed at a site where the tail has a diameter of 2.5 mm.

Results: As shown in FIG. 9, after a period of time, the mice in the minicircle DNA (MC.BDD-FVIII-SQ-CO2) injection group and the mice in the untreated control group (no minicircle DNA, only injected with equal volume of PBS buffer) were subjected to tail cutting (at the sites where the tail had a diameter of 2 mm if cut at 1 month; and a diameter of 2.5 mm if cut at 2 months) to compare the bleeding volume s therebetween. It is found that the two groups had comparable bleeding volume without statistical difference, indicating that MC.BDD-FVIII-SQ-CO2 treatment failed to improve the coagulation function of mice with hemophilia A.

Example 6: Measurement of Target Protein Expression Level by ELISA

The cell culture supernatants of MC.BDD-FVIII-L1, MC.BDD-FVIII-L2, MC.BDD-FVIII-L3, MC.BDD-FVIII-v3, and MC.BDD-FVIII-N8 obtained in Example 3 were respectively measured for their target protein expression levels by ELISA.

Figure 10:
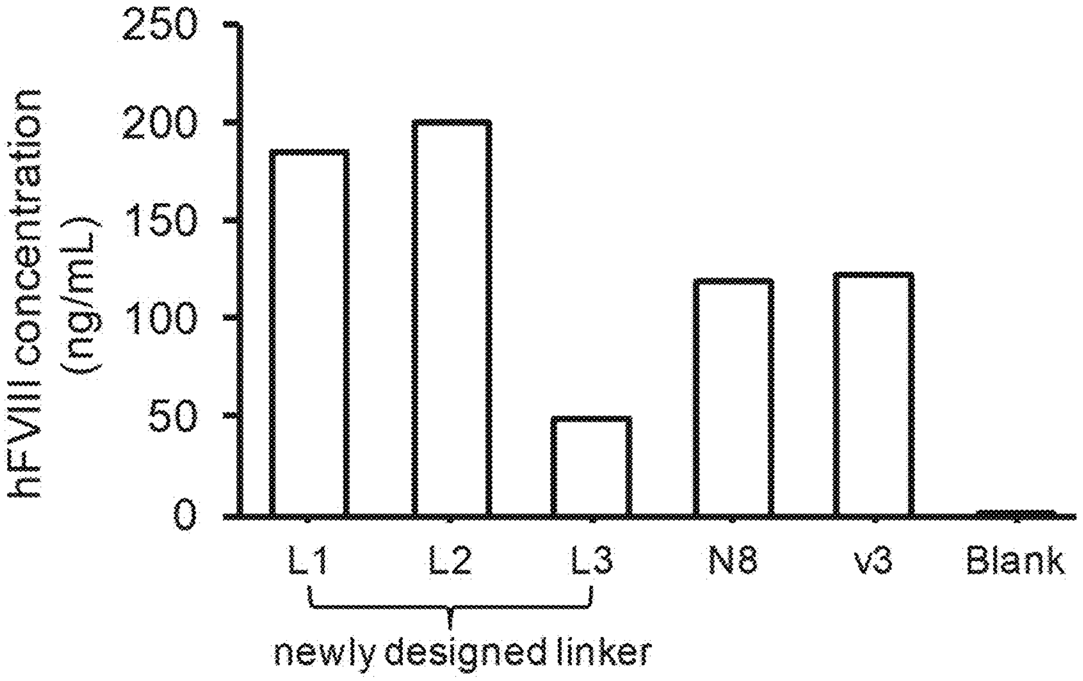
FIG. 10 is a statistical diagram of the results of measuring the in vitro cell expression levels of the target proteins of 293T cells transfected by MC.BDD-FVIII-L1, MC.BDD-FVIII-L2, and other FVIII minicircle DNA vectors in Example 6.

Results: As shown in FIG. 10, the target protein expression levels of MC.BDD-FVIII-L1 and MC.BDD-FVIII-L2 are significantly higher than those of other FVIII minicircle DNA expression vectors. The relative levels are as follows:

(1) The target protein expression level ratios of MC.BDD-FVIII-L1 to MC.BDD-FVIII-N8 and MC.BDD-FVIII-v3:

MC.BDD-FVIII-L1: MC.BDD-FVIII-N8=1.867;

MC.BDD-FVIII-L1: MC.BDD-FVIII-v3=1.849;

MC.BDD-FVIII-L1 is approximately 87% and 85% higher than MC.BDD-FVIII-N8 and MC.BDD-FVIII-v3, respectively.

(2) The target protein expression level ratios of MC.BDD-FVIII-L2 to MC.BDD-FVIII-N8 and MC.BDD-FVIII-v3:

MC.BDD-FVIII-L2: MC.BDD-FVIII-N8=1.924;

MC.BDD-FVIII-L2: MC.BDD-FVIII-v3=1.906;

MC.BDD-FVIII-L2 is approximately 92% and 91% higher than MC.BDD-FVIII-N8 and MC.BDD-FVIII-v3, respectively.

(3) The target protein expression level ratios of MC.BDD-FVIII-L3 to MC.BDD-FVIII-N8 and MC.BDD-FVIII-v3:

MC.BDD-FVIII-L3: MC.BDD-FVIII-N8=0.443;

MC.BDD-FVIII-L3: MC.BDD-FVIII-v3=0.439;

MC.BDD-FVIII-L3 is appropriately equivalent to 44% of MC.BDD-FVIII-N8 or MC.BDD-FVIII-v3.

MC.BDD-FVIII-v3: MC.BDD-FVIII-N8=1.01, and there is almost no difference between MC.BDD-FVIII-v3 and MC.BDD-FVIII-N8.

(4) The target protein expression level ratios of MC.BDD-FVIII-L1 to MC.BDD-FVIII-L2:

MC.BDD-FVIII-L1: MC.BDD-FVIII-L2=0.97, and there is almost no difference between MC.BDD-FVIII-L1 and MC.BDD-FVIII-L2.

Conclusions: The FVIII minicircle DNA vector of linker peptide containing L1-linker or L2-linker has a higher expression level of the target protein than that of the FVIII minicircle DNA vector of another type of linker peptide.

Example 7: Detection of In Vitro Coagulation Activity (One-Stage APTT Method)

Operations: The cell culture supernatants of MC.BDD-FVIII-L1 and MC.BDD-FVIII-L2 with the highest expression level of the target protein obtained in Example 3 were collected and sent to the Institute of Blood Transfusion, Chinese Academy of Medical Sciences for detection of the coagulation activity using the one-stage APTT method. The FVIII activity of normal pooled plasma (NPP) is defined as 100%.

Results: The measured activities of the expression products (the cell culture supernatant at 72 h) of MC.BDD-FVIII-L1 and MC.BDD-FVIII-L2 were respectively 118.1% and 116% (the reference activity for a person with normal coagulation function ranges from 50% to 150%), indicating that the FVIII containing a linker peptide of L1-linker or L2-linker has good coagulation activity.

Example 8: In Vivo Expression (1) Expression in Normal Mice

Operations: Ten 6-8-week-old Balb/c mice were randomly divided into two groups with 5 mice in each group so that there were 5 mice in the MC.BDD-FVIII-L1 group and 5 mice in the MC.BDD-FVIII-L2 group. Blood was collected one day before the injection of minicircle DNA, and plasma was separated and stored at −80° C., which was used as a blank control sample (W0). The mice in the two groups were intramuscularly injected with the MC.BDD-FVIII-L1 minicircle DNA and the MC.BDD-FVIII-L2 minicircle DNA at a dose of 30 μg/50 μL/mouse, and then a pulsed electric field was applied (TERESA in vivo gene introduction instrument; Parameters: 36 V, 10 ms, 1 Hz). After the injection, blood was collected periodically, and plasma was separated and stored at −80° C. The target protein expression level in the plasma sample was detected using a Human FVIII ELISA kit (VisuLize Factor VIII PLUS Antigen ELISA Kit, Affinity Biologicals Inc).

Figure 11:
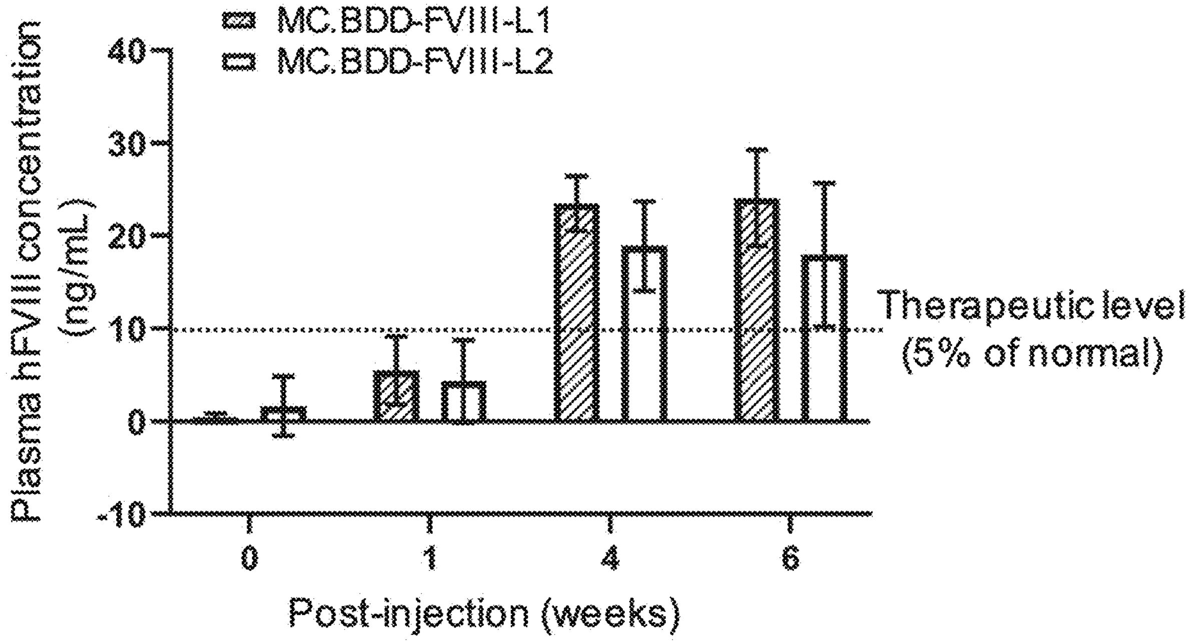
FIG. 11 is a statistical diagram of the expression levels of MC.BDD-FVIII-L1 and MC.BDD-FVIII-L2 in normal mice in Example 8.

Results: As shown in FIG. 11. There is no expression in the blank control sample. 4 weeks after the injection, the MC.BDD-FVIII-L1 group and the MC.BDD-FVIII-L2 group have similar in vivo expression levels of MC.BDD-FVIII-L1 and MC.BDD-FVIII-L2 of up to 20 ng/mL or more (equivalent to 10% or more of the normal plasma FVIII concentration level in normal person (20 ng/mL)), which exceeds the significant therapeutic level that can significantly improve moderate or severe hemophilia to mild (>5%).

(2) Expression in Beagle Dogs

Operations: 3 adult beagle dogs with weight of about 13 kg were subjected to blood collection before the injection of minicircle DNA, and plasma was separated and stored at −80° C., which was used as a blank control sample (W0). On the day of blood collection, each dog was continued to inject with 600 g of MC.BDD-FVIII-L1 minicircle DNA, and then a pulsed electric field was applied (TERESA in vivo gene introduction instrument; parameters: 36 V, 10 ms, 1 Hz). Then, blood was collected every week, and plasma was separated and stored at −80° C. The target protein expression level in the plasma sample was detected using a Human FVIII ELISA kit (VisuLize Factor VIII PLUS Antigen ELISA Kit, Affinity Biologicals Inc), and then converted to a relative FVIII level in the Normal Pooled Plasma (NPP). The FVIII concentration in the Normal Pooled Plasma is about 200 ng/mL.

Figure 12:
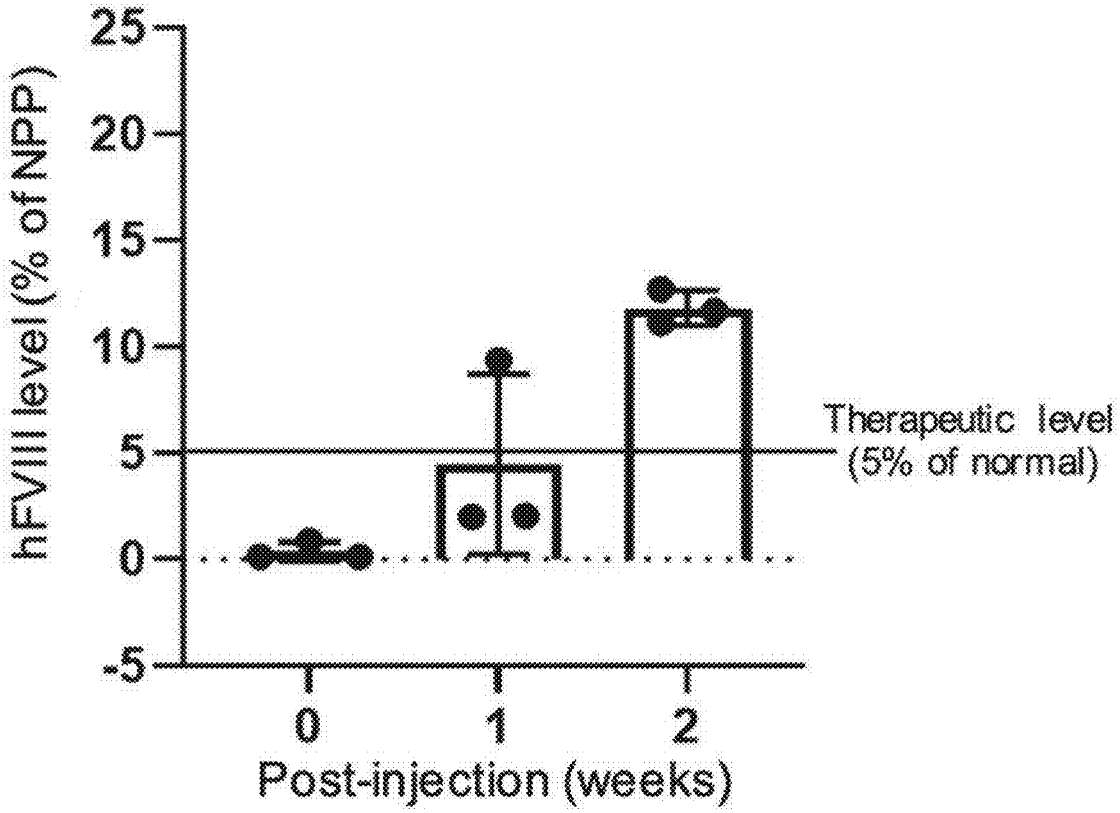
FIG. 12 is a statistical diagram of the in vivo expression level of MC.BDD-FVIII-L1 in beagle dogs in Example 8.

Results: As shown in FIG. 12. There is no expression in the blank control sample. One week after the injection of MC.BDD-FVIII-L1 minicircle DNA, the plasma hFVIII expression reached 5% (10 ng/mL) or more of the normal FVIII concentration level in the normal human plasma in one dog, but were relatively low in the other two dogs; and two weeks after the injection of MC.BDD-FVIII-L1 minicircle DNA, the expression levels gradually increased and all exceeded 10% (20 ng/mL) of the normal FVIII concentration level in normal human plasma.

Example 9: Activity in Mice with Hemophilia A (1) In Vivo Expression Level of MC.BDD-FVIII-L1 in Mice with Hemophilia A (F8-KO Mice)

Operations: One day before the injection of minicircle DNA, five 6-8-week-old male F8-KO mice were subjected to blood collection and plasma was separated and stored at −80° C., which was used as a blank control sample (W0). All the mice were intramuscularly injected with the minicircle DNA (MC.BDD-FVIII-L1 minicircle DNA) at a dose of 30 μg/50 μL/mouse (30 g minicircle DNA in 50 μL solution), and then a pulsed electric field was applied (TERESA in vivo gene introduction instrument; Parameters: 36 V, 10 ms, 1 Hz). After 6 weeks (W6), blood was collected, and plasma was separated and stored at −80° C. The target protein expression level in the plasma sample was detected using a Human FVIII ELISA kit (VisuLize Factor VIII PLUS Antigen ELISA Kit, Affinity Biologicals Inc).

Figure 13:
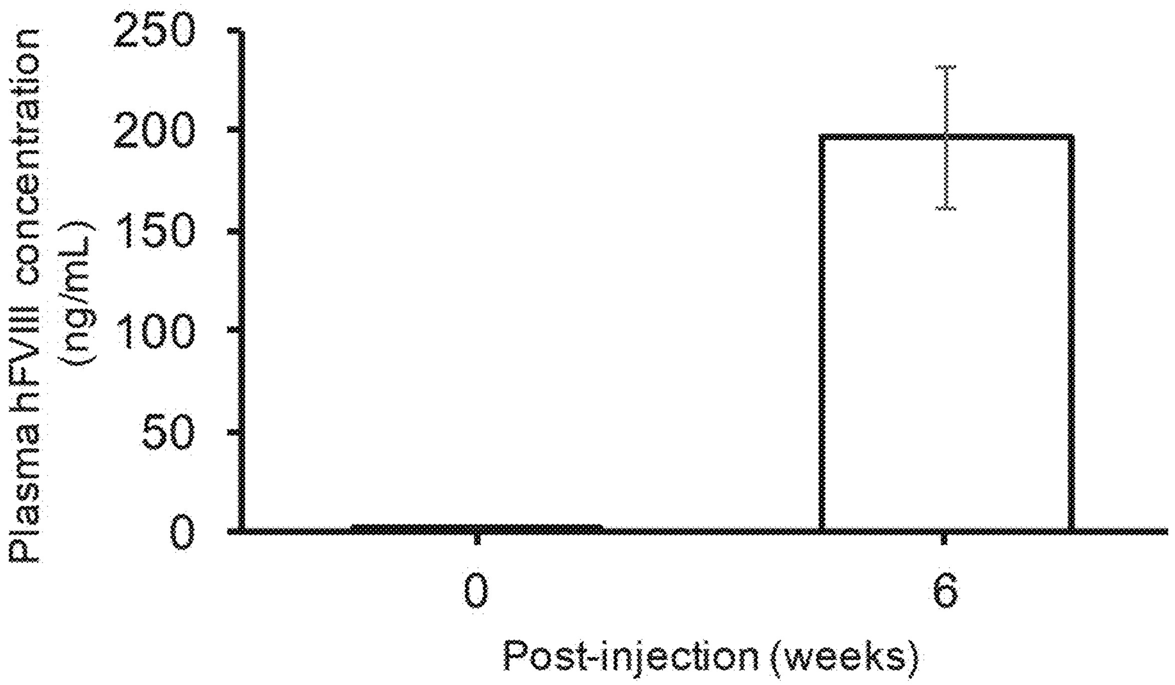
FIG. 13 is a statistical diagram of the expression level of MC.BDD-FVIII-L1 in mice with hemophilia A (F8-KO mice) in Example 9.

Results: The results are shown in FIG. 13. There is no expression in the blank control sample. 6 weeks after the injection of MC.BDD-FVIII-L1 minicircle DNA, it is measured by ELISA that the plasma target protein level is up to 100 ng/mL or more, which has exceeded 50% (100 ng/mL) of the normal FVIII concentration level in normal human plasma, indicating that it can functionally cure hemophilia and restore the normal coagulation function.

(2) Treatment of MC.BDD-FVIII-L1 on Mice with Hemophilia A (F8-KO Mice)

Operations: Ten 6-8-week-old male F8-KO mice were randomly divided into two groups including a blank control group (PBS) and a minicircle DNA treatment group (the MC treatment group, MC), with 5 mice in each group. Each mouse in the minicircle DNA treatment group was intramuscularly injected with MC.BDD-FVIII-L1 minicircle DNA solution at a dose of 30 μg/50 μL (30 μg minicircle DNA in 50 μL solution), and then a pulsed electric field was applied after the injection (TERESA in vivo Gene introduction instrument; parameters: 36 V, 10 ms, 1 Hz); and the mice in the blank control group were injected with an equal volume of PBS buffer by the same way. Additional five male C57 mice of the same age served as wild-type controls (WT) with normal coagulation function. 4 weeks after the injection, a tail-cutting experiment was performed at site where the tail had a diameter of 2 mm, and the bleeding volume within 15 minutes was recorded. After the experiment, the mice were sacrificed.

Figure 14:
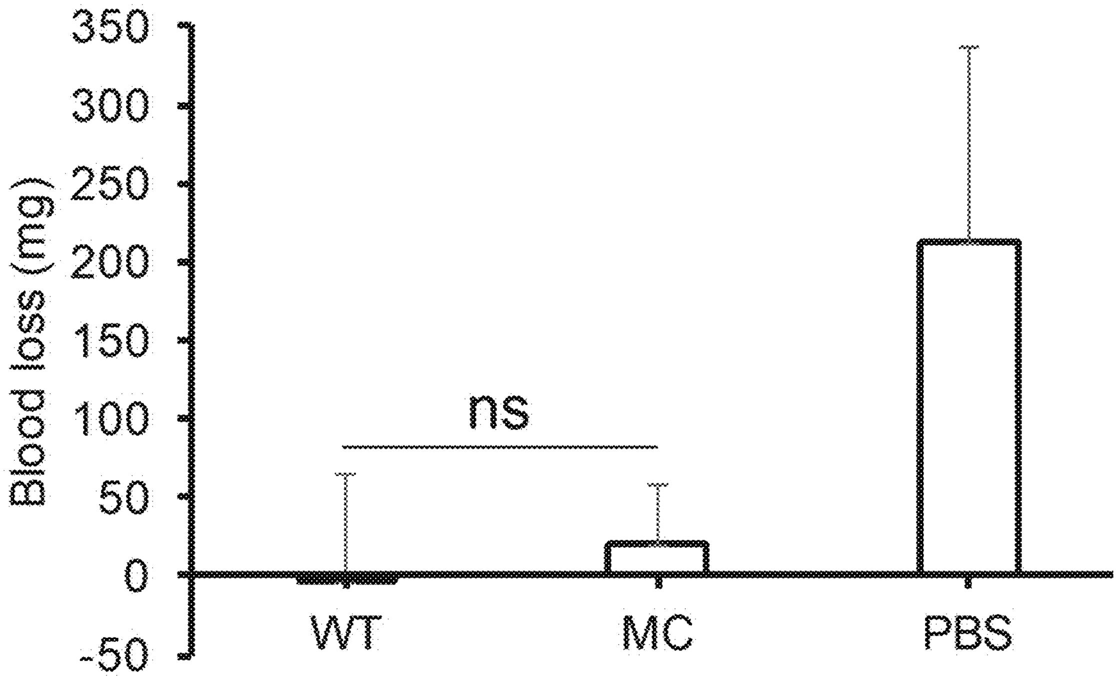
FIG. 14 is a statistical diagram of blood loss in the tail-cutting experiments of the F8-KO mice in the blank control group (PBS), the F8-KO mice in the MC.BDD-FVIII-L1 minicircle DNA treatment group (MC) and the wild-type normal mice (WT) in Example 9.

Results: As shown in FIG. 14, in comparison with the blank control group (PBS), the bleeding volume of the mice in the MC.BDD-FVIII-L1 minicircle DNA treatment group (the MC treatment group, MC) was significantly reduced, while the bleeding volume of the mice in the MC treatment group is comparable with the bleeding volume of the wild-type normal mice (WT) (no statistical difference, ns); indicating that the coagulation function of the mice with hemophilia A has returned to normal after the MC treatment.

(3) Identification of Activity of MC.BDD-FVIII-L2 in Mice with Hemophilia A (F8-KO Mice)

Operations: Twenty 9-10-week-old male F8-KO mice were randomly divided into two groups: 5 mice in the blank control group (PBS) and 15 mice in the minicircle DNA injection group (the MC treatment group, MC). The mice in the MC treatment group were injected with MC.BDD-FVIII-L2 minicircle DNA solution (3 g minicircle DNA dissolved in 1.8 mL PBS buffered solution) at a dose of 3 μg/1.8 mL/mouse (3 g minicircle DNA in 1.8 mL solution) by ways of high-pressure injection through tail vein (1.8 mL of solution is rapidly injected through the tail vein within 5-8 seconds); and the mice in the blank control group were injected with an equal volume (1.8 mL) of PBS buffered solution by the same way. Additional five male C57 mice of the same age served as wild-type controls (WT) with normal coagulation function. 24 hours after the injection, a tail-cutting experiment was performed at a point where the diameter of the mouse tail was 2 mm, and the bleeding volume within 15 minutes was recorded; the mice were sacrificed after the experiment. One mouse in the blank control group died due to abnormal high-pressure injection operation and failed to undergo tail cutting.

Figure 15:
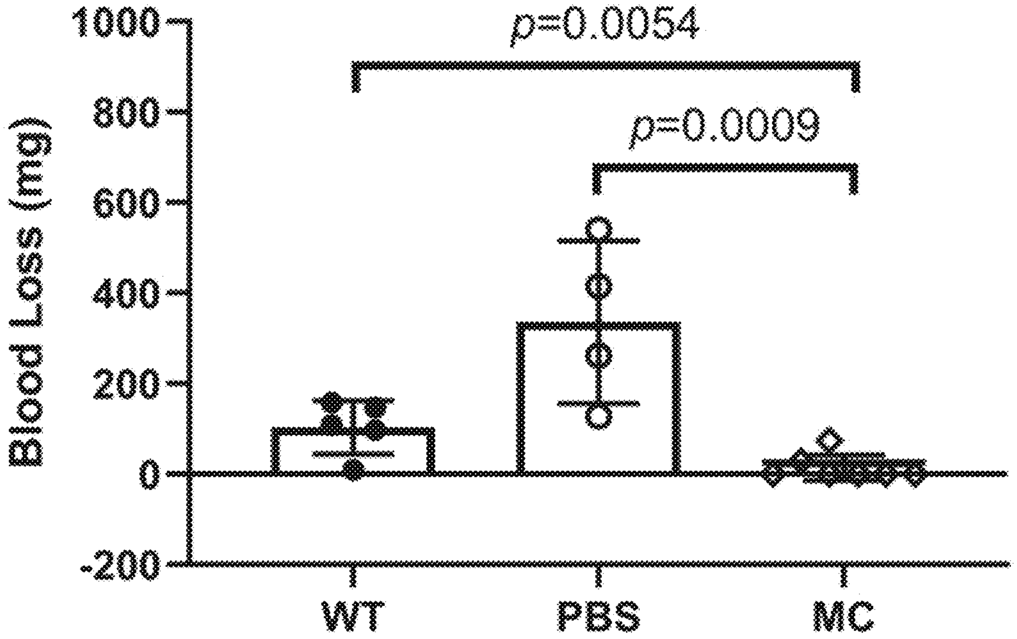
FIG. 15 is a statistical diagram of blood loss in the tail-cutting experiments of the F8-KO mice in the blank control group (PBS), the F8-KO mice in the MC.BDD-FVIII-L2 minicircle DNA treatment group (MC) and the wild-type normal mice (WT) in Example 9.

Results: As shown in FIG. 15, in comparison with the blank control group (PBS), the bleeding volume of the mice in the MC.BDD-FVIII-L2 minicircle DNA injection group (the MC treatment group, MC) was significantly reduced, even less than the untreated wild-type normal mice (WT), indicating that MC.BDD-FVIII-L2 has extremely high coagulation activity in vivo.

Example 10: Other Modifications (1) Fc Fusion

Fc fusion is important means to increase the half-life of FVIII. Molecules with longer half-lives of in vivo expression may result in more product accumulation in the body to achieve higher expression level. To verify this idea, we constructed the minicircle DNA expression vector (MC.BDD-FVIII-CTP-Fc) of the BDD-FVIII-Fc fusion protein (SEQ ID NO.19) (the nucleotide sequence of the minicircle is shown in the Table 1).

Operations: Ten 6-8-week-old Balb/c mice were randomly divided into two groups: 5 mice in the minicircle DNA (MC.BDD-FVIII-CTP-Fc) injection group and 5 mice in the PBS blank control group (control). The mice in the minicircle group were intramuscularly injected with the minicircle DNA (MC.BDD-FVIII-CTP-Fc) at dose of 45 μg/50 μL/mouse (each mouse was injected with 50 μL comprising g minicircle DNA which is equimolar to 30 μg MC.BDD-FVIII), and each mouse in the blank control group was intramuscularly injected with 50 μL PBS. After the intramuscular injection, a pulsed electric field was applied (TERESA in vivo gene introduction instrument; Parameters: 36 V, 10 ms, 1 Hz). Then, blood was collected periodically, and plasma was separated and stored at −80° C. The target protein expression level in the plasma sample was detected using a Human FVIII ELISA kit (VisuLize Factor VIII PLUS Antigen ELISA Kit, Affinity Biologicals Inc).

Figure 16:
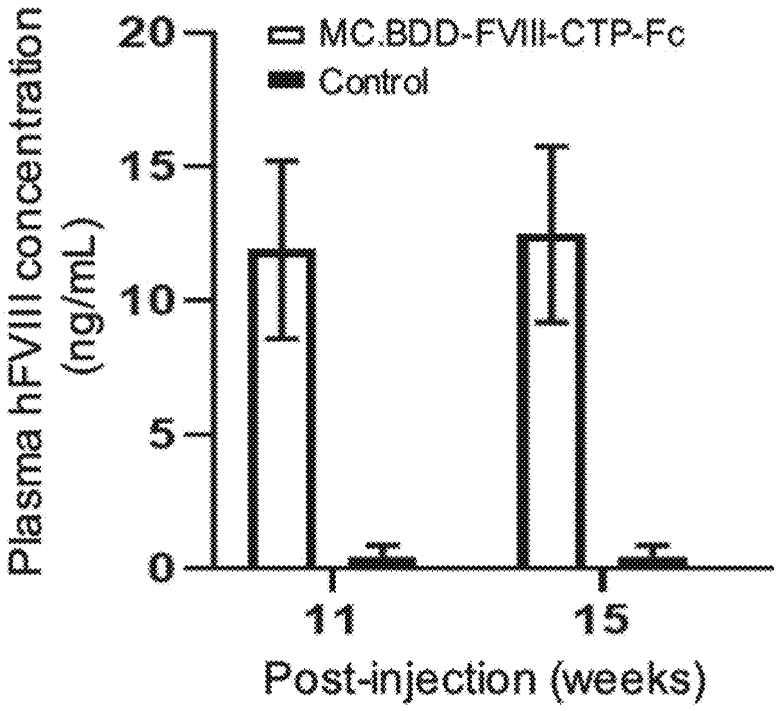
FIG. 16 is a statistical diagram of the in vivo expression level of MC.BDD-FVIII-CTP-Fc in Example 10.

Results: As shown in FIG. 16. There is no expression in the blank control sample. 11-15 weeks after the injection of MC.BDD-FVIII-CTP-Fc minicircle DNA, it was found that the minicircle DNA of the BDD-FVIII-Fc fusion protein could not further increase the in vivo expression level (only about 10 ng/mL, which is partially less than that 5% (10 ng/mL) of the normal FVIII concentration level in normal human plasma).

(2) X5 Mutation

Measurement of In Vitro Cell Expression Level of the Target Protein by ELISA:

Operations: Mutation X5 (i.e., five key amino acids in the A region of human FVIII are mutated to the amino acids at the corresponding sites of porcine FVIII; I86V/A108S/G132K/M147T/L152P) was introduced into the BDD-FVIII-L1 to give the BDD-FVIII-L1-X5 nucleotide sequence (SEQ ID NO.22) so as to construct the corresponding MC expression vector (the nucleotide sequences of various minicircles are shown in Table 1): MC.BDD-FVIII-L1-X5 minicircle DNA. MC.BDD-FVIII-L1 minicircle DNA and MC.BDD-FVIII-L1-X5 minicircle DNA were transfected into 293T cells, respectively. After 72 hours, the cell culture supernatant was collected, and the target protein level was measured by ELISA.

Figure 17:
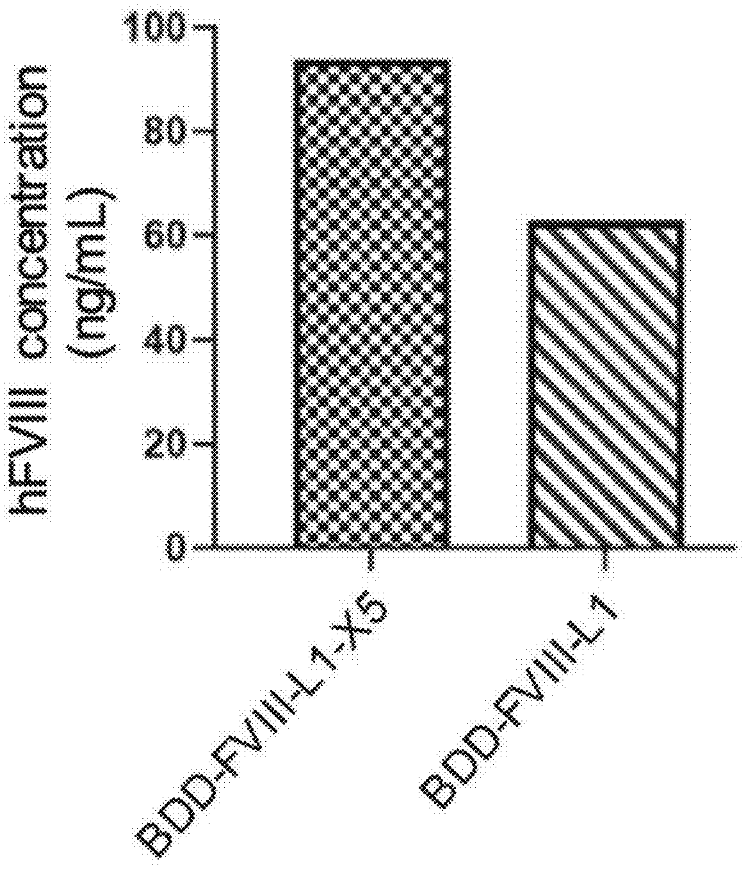
FIG. 17 is a statistical diagram of the results of measuring the in vitro cell expression levels of the target proteins of 293T cells transfected by MC.BDD-FVIII-L1-X5 and MC.BDD-FVIII-L1 in Example 10 using ELISA.

Results: As shown in FIG. 17, in comparison with the MC.BDD-FVIII-L1 minicircle DNA, the target protein level was improved after the introduction of the X5 mutation.

Experiments in Mice:

Operations: Ten 6-8-week-old Balb/c mice were randomly divided into two groups with 5 mice in each group. The mice in each group were intramuscularly injected with the minicircle DNA (MC.BDD-FVIII-L1 minicircle DNA or MC.BDD-FVIII-L1-X5 minicircle DNA) at a dose of 30 μg/50 μL/mouse (each mouse was injected with 50 μL containing 30 g minicircle DNA). After the intramuscular injection, a pulsed electric field was applied (TERESA in vivo gene introduction instrument; parameters: 36 V, 10 ms, 1 Hz). 4 weeks after the injection, blood was collected and the plasma was separated. The target protein expression level in the plasma sample was detected using a Human FVIII ELISA kit (VisuLize Factor VIII PLUS Antigen ELISA Kit, Affinity Biologicals Inc).

Figure 18:
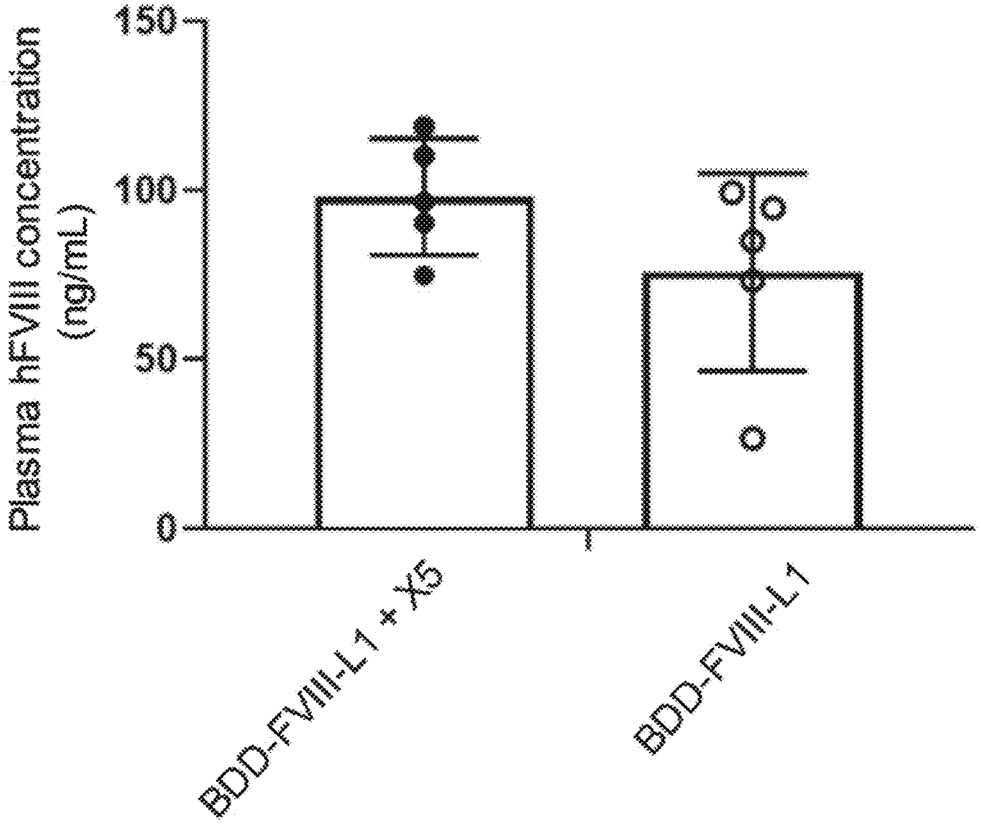
FIG. 18 is a statistical diagram of the results of target protein expression level of MC.BDD-FVIII-L1-X5 and MC.BDD-FVIII-L1 in the plasma samples in the in vivo experiments in mice in Example 10.

Results: As shown in FIG. 18, in comparison with MC.BDD-FVIII-L1 minicircle DNA, the target protein level was slightly improved after the introduction of the X5 mutation.

(3) R1645H Mutation

Siner et al. (Blood 2013, 121:4396-4403) reported that mutating the furin site at the C terminus of the SQ linker in the B region of BDD-FVIII was mutated ($R_{1645}$-$H_{1646}$-$Q_{1647}$-$R_{1648}$) results in that the BDD-FVIII is unable to be recognized and cleaved by the Furin protease so that the expression increases. Since the recognition pattern of the furin site is R-X-X-R (that is, the first and last amino acids are arginine, and the middle two amino acids are arbitrary), by mutating the arginine at position 1645 or 1648 to any other amino acid except arginine, it can theoretically achieve the purpose of failing to be recognized and cleaved by the Furin proteas. This purpose can also be achieved by deleting the furin site (including deleting all 4 amino acids of RHQR, or any 1, 2 or 3 amino acids therein).

In the present disclosure, the furin site of RHQR is retained at the C-terminal of the L1 linker. Accordingly, we mutate the arginine (Arg, R) at the $4^{th}$ position from the C-terminal of the L1 linker to histidine (His, H), that is, a R1645H mutation, to give a coding sequence BDD-FVIII-$L1_{R1645H}$ of the BDD-FVIII-L1 (the nucleotide sequence is shown in Table 1), which was construct into a corresponding MC expression vector MC.BDD-FVIII-$L1_{R1645H}$ (the nucleotide sequence of the minicircle is shown in Table 1).

(4) F309S Mutation

Swaroop et al (J Biol Chem 1997, 272:24121-24124) reported that the F309S mutation (the phenylalanine at position 309 of FVIII is mutated to serine) can promote FVIII secretion. Accordingly, we mutated the phenylalanine at position 309 of BDD-FVIII-L1, BDD-FVIII-$L1_{R1645H}$ and BDD-FVIII-L2 to serine (Ser, S) to respectively give the coding sequences of BDD-$FVIII_{F309S}$-L1, BDD-$FVIII_{F309S}$-$L1_{R1645H}$ and BDD-$FVIII_{F309S}$-L2 (various nucleotide sequences ae shown in Table 1), which were constructed into the corresponding MC expression vectors MC.BDD-$FVIII_{F309S}$-L1, MC.BDD-$FVIII_{F309S}$-$L1_{R1645H}$ and MC.BDD-$FVIII_{F309S}$-L2 (the nucleotide sequences of various minicircles are shown in Table 1).

Example 11: Therapeutic Effect of Secondary Administration

Operations: Ten 6-8-week-old Balb/c mice were randomly divided into two groups: 5 in the MC.BDD-FVIII-F1 group and 5 in the MC.BDD-FVIII-L2 group. Each mouse in the two groups was intramuscularly injected with the MC.BDD-FVIII-L1 minicircle DNA and the MC.BDD-FVIII-L2 minicircle DNA at a dose of 30 μg/50 μL/mouse (each mouse was injected with 50 μL containing 30 g minicircle DNA), and then a pulsed electric field was applied (TERESA in vivo gene introduction instrument; parameters: 36 V, 10 ms, 1 Hz). On the $22^{nd}$ week (W22) after the injection, the mice were dosed by the same way. After the first and second injections, blood was collected periodically, and plasma was separated and stored at −80° C. The target protein expression level in the plasma sample was detected using a Human FVIII ELISA kit (VisuLize Factor VIII PLUS Antigen ELISA Kit, Affinity Biologicals Inc). And it was converted into the relative level of FVIII in normal pooled plasma (NPP). The FVIII concentration in the Normal Pooled Plasma is about 200 ng/mL.

Figure 19:
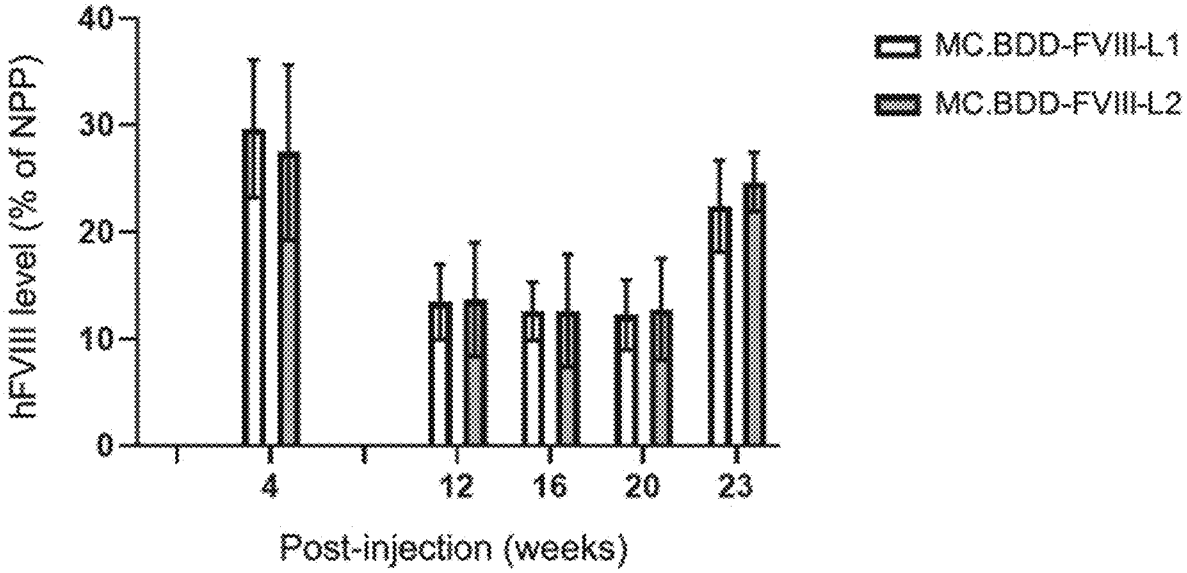
FIG. 19 is a statistical diagram of the therapeutic effects of secondary administration of MC.BDD-FVIII-L1 and MC.BDD-FVIII-L2 in Example 11.

Results: As shown in FIG. 19. After the injection of minicircle DNA, the expression levels in mice of both groups were above 20% (40 ng/mL) of the normal FVIII concentration level in normal human plasma on the $4^{th}$ week (W4). The expression levels were somewhat decreased on the $12^{th}$ week (W12), but could still be maintained at above 10% (20 ng/mL) of the normal level of normal human plasma FVIII concentration for a long time (on the $12^{th}$ to $20^{th}$ weeks, W12-W20). After the boosting administration on the $22^{nd}$ week (W22), the expression level rapidly returned to the level close to that before the decrease on W23 (the $23^{rd}$ week after the first injection, that is, the week immediately after the second injection). It shows that the second injection of the minicircle DNA provided in the present disclosure is still effective and will not produce a virus-specific immune response. It can be injected twice and restore or enhance the therapeutic effect by repeated administration as needed.

Example 12: Long-Term Expression In Vivo

Operations: Ten 6-8-week-old Balb/c mice were randomly divided into two groups: 5 in the MC.BDD-FVIII-F1 group and 5 in the MC.BDD-FVIII-L2 group. Blood was collected before the injection of minicircle DNA, and plasma was separated and stored at −80° C., which was used as a blank control sample (W0). Each mouse in the two groups was intramuscularly injected with the MC.BDD-FVIII-L1 minicircle DNA and the MC.BDD-FVIII-L2 minicircle DNA at a dose of 30 μg/50 μL/mouse (each mouse was injected with 50 μL containing 30 μg minicircle DNA), and then a pulsed electric field was applied (TERESA in vivo gene introduction instrument; parameters: 36 V, 10 ms, 1 Hz). On the 22$^{nd}$ week after the injection, the mice were dosed by the same way. After the injection, blood was collected periodically, and plasma was separated and stored at −80° C. The target protein expression level in the plasma sample was detected using a Human FVIII ELISA kit (VisuLize Factor VIII PLUS Antigen ELISA Kit, Affinity Biologicals Inc).

Figure 20:
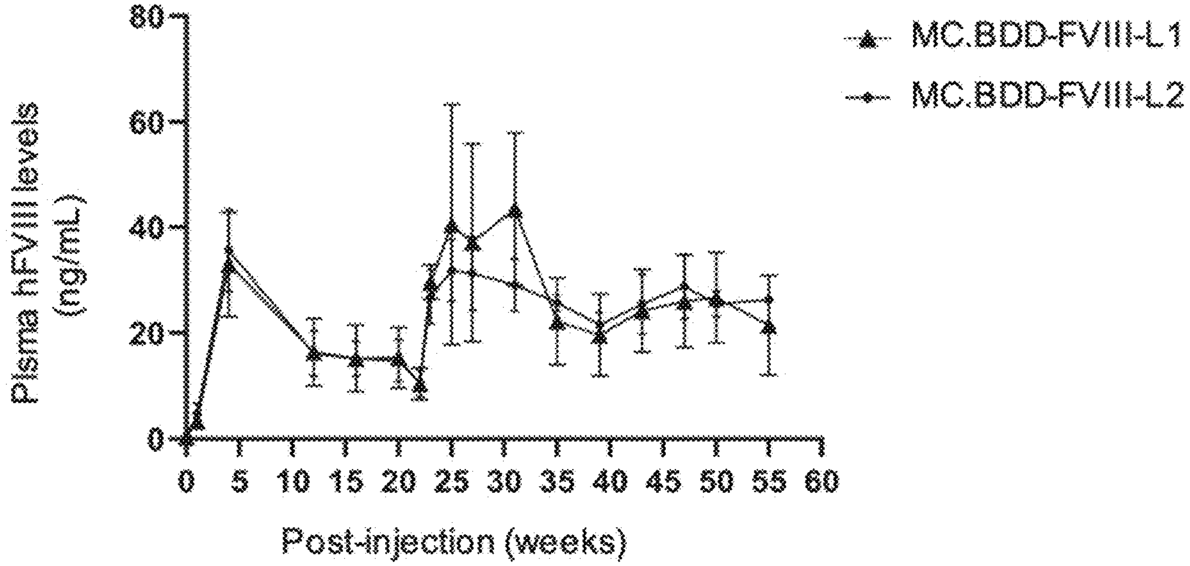
FIG. 20 is a graph showing the long-term expression of MC.BDD-FVIII-L1 minicircle DNA and MC.BDD-FVIII-L2 minicircle DNA in mice in Example 12, respectively.

Results: As shown in FIG. 20, both MC.BDD-FVIII-L1 and MC.BDD-FVIII-L2 can be expressed in mice for a long time of 1 year or more, and the secondary injection of the minicircle DNA provided in the present disclosure is still effective for a long time, which will not produce a virus-specific immune response.

Example 13: Safety Study

Operation: An adult female beagle dog with weight of 10-12 kg (No. D0016) and an adult male beagle dog with weight of 10-12 kg (No. C957) were injected with 1.2 mg of MC.BDD-FVIII-L1 minicircle DNA, respectively, and a pulsed electric field (36 V, 10 ms, 1 Hz) was applied. At the 6$^{th}$ week after injection, samples were collected from lung, liver, spleen, kidney, heart, brain, ovary or testicle, muscle and thymus tissues, and subjected to sectioning, HE staining, and pathological examination. The results are shown in FIGS. 21A and 21B.

Results: 6 weeks after the injection of MC.BDD-FVIII-L1 minicircle DNA, the pathological examination performed on the lungs, liver, spleen, kidney, heart, brain, ovary (female dog D0016) or testis (male dog C957), muscle and thymus tissues of beagle dogs were all normal (FIGS. 21A and 21B). It shows that no obvious toxicity was found, and MC.BDD-FVIII-L1 has good safety.

The method of the present disclosure has been described through preferred embodiments. Relevant persons can obviously make modifications or appropriate changes and combinations to the methods and applications described herein within the content, spirit and scope of the present disclosure to implement and apply the technology of the present disclosure. Those skilled in the art can learn from the contents herein and appropriately improve the implementation of process parameters. It should be noted that all similar substitutions and modifications are obvious to those skilled in the art, and they are deemed to be included in the present disclosure.

The invention claimed is:

1. A coagulation factor VIII (FVIII) protein comprising a linker peptide connecting A1-A2 domains with A3-C1-C2 domains; wherein the linker peptide of the FVIII protein comprising the amino acid sequence as shown in SEQ ID NO. 1 or SEQ ID NO. 2.

2. The FVIII protein according to claim 1, wherein the FVIII protein further comprising the amino acid sequence of SEQ ID NO. 5, SEQ ID NO. 6, SEQ ID NO. 21, SEQ ID NO. 23, SEQ ID NO. 43, SEQ ID NO. 44, SEQ ID NO. 50, SEQ ID NO. 51, SEQ ID NO. 52 or SEQ ID NO. 53.

3. The FVIII protein according to claim 1, wherein a nucleotide sequence encoding the linker peptide comprises SEQ ID NO. 3 or SEQ ID NO. 4.

* * * * *